United States Patent [19]
Potempa et al.

[11] Patent Number: 6,129,917
[45] Date of Patent: *Oct. 10, 2000

[54] IMMUNOGENIC COMPOSITIONS COMPRISING PORPHYROMONAS GINGIVALIS PROTEINS AND/OR PEPTIDES AND METHODS

[75] Inventors: Jan Potempa; James Travis, both of Athens; Caroline Attardo Genco, Atlanta, all of Ga.

[73] Assignees: The University of Georgia Research Foundation, Inc., Athens; Morehouse School of Medicine, Atlanta, both of Ga.

[*] Notice: This patent issued on a continued prosecution application filed under 37 CFR 1.53(d), and is subject to the twenty year patent term provisions of 35 U.S.C. 154(a)(2).

[21] Appl. No.: 08/822,324

[22] Filed: Mar. 21, 1997

Related U.S. Application Data

[60] Provisional application No. 60/013,945, Mar. 22, 1996.
[51] Int. Cl.$^7$ .......................... A61K 39/00; A61K 39/38; A61K 38/00; C07K 17/00
[52] U.S. Cl. .................................... 424/184.1; 424/242.1; 424/234.1; 424/190.1; 424/682; 530/300; 530/350; 530/326; 530/325; 514/2; 514/12
[58] Field of Search ............................. 424/184.1, 242.1; 514/2, 12; 530/300, 350

[56] References Cited

U.S. PATENT DOCUMENTS

| | | |
|---|---|---|
| 3,817,837 | 6/1974 | Rubenstein et al. . |
| 3,850,752 | 11/1974 | Schuurs et al. . |
| 3,939,350 | 2/1976 | Kronick et al. . |
| 3,996,345 | 12/1976 | Ullman et al. . |
| 4,275,149 | 6/1981 | Litman et al. . |
| 4,277,437 | 7/1981 | Maggio . |
| 4,366,241 | 12/1982 | Tom et al. . |
| 4,816,567 | 3/1989 | Cabilly et al. . |
| 5,462,734 | 10/1995 | Letchworth, III et al. . |
| 5,475,097 | 12/1995 | Travis et al. . |
| 5,523,390 | 6/1996 | Travis et al. ........................... 536/23.2 |
| 5,536,497 | 7/1996 | Evans et al. . |
| 5,571,531 | 11/1996 | McDermott et al. . |
| 5,824,791 | 10/1998 | Progulske-Fox et al. . |
| 5,830,710 | 11/1998 | Progulske-Fox et al. . |

FOREIGN PATENT DOCUMENTS

| | | |
|---|---|---|
| 95/07286 | 3/1995 | WIPO . |
| 95/11298 | 4/1995 | WIPO . |
| 96/17936 | 6/1996 | WIPO . |

OTHER PUBLICATIONS

Imamura et al, JBC, 272(25):16062–67, Jun., 1997.
Chen et al, Inf. & Imm, 59(8):2846–2850, Aug., 1991.
Pike et al, J. Bacterial, 178(10):2876–2882, May, 1996.
Jagels et al, Adv. Exp. Med. Biol. 389(Intracellular Protein Catabolism) 155–164, 1996.
Imamura et al. Inf. & Imm. 63(12): 4877–4882, Dec. 1995.
Jagels et al, Inf. & Imm. 64(6): 1984–1991, Jun. 1996.
Okamoto et al, Archives Biochem & Biophys. 316(2):917–925, Feb. 1995.
Imamura et al, Inf. & Imm, 63(5): 1999–2003, May 1995.
Agawa, J. Med. Microbiol, 41: 349–358, 1994.
Aduse–Opoku, J. et al. (1995), "Characterization, Genetic Analysis, and Expression of a Protease Antigen (PrpRI) of *Porphyromonas gingivalis* W50," Infect. Immun. 63(12):4744–4754.
Barkocy–Gallagher et al. (1996), "Analysis of the prtP Gene Encoding Porphypain, a Cysteine Proteinase of *Porphyromonas gingivalis*," J. Bacteriol. 178:2734–2741.
Chen et al. (1992), "Purification and Characterization of a 50–dKa Cysteine Proteinase (Gingipain) from *Porphyromonas gingivalis*," J. Biol. Chem. 267:18896–18901.
Curtiss et al. (1996), "Characterization of an Adherence and Antigenic Determinant of the ArgI Protease of *Porphyromonas gingivalis* Which is Present on Multiple Gene Products," Infect. Immun. 64:2532–2539.
Ebersole et al. (1984), "Serological Identification of Oral Bacteroides spp. by Enzyme–Linked Immunosorbent Assay," J. Clin. Microbiol. 19:639–644.
Ebersole et al. (1989), "Murine Model for Virulence Characteristics of Periodontopathogens," J. Dent. Res. 68:286, Abstract 837.
Genco et al. (1991), "A Novel Mouse Model to Study the Virulence of and Host Response to *Porphyromonas* (Bacteroids) *gingivalis,*" Infect. Immun. 59:1255–1263.
Genco et al. (1992), "Influence of Immunization on *Porphyromonas gingivalis* Colonization and Invasion in the Mouse Chamber Model," Infect. Immun. 60:1447–1454.
Genco et al. (1995), "Resistance of a Tn4351–Generated Polysaccharide Mutant of *Porphyromonas gingivalis* to Polymorphonuclear Leukocyte Killing," Infect. Immun. 63(2):393–401.
Goulbourne and Ellen (1991), "Evidence that *Porphyromonas* (Bacteriodes) *gingivalis* Fimbriae Function in Adhesion to *Actinomyces viscosus,*" J. Bacteriol. 173:5266–5274.
Gunsolley et al. (1990), "Serum Antibodies to Periodontal Bacteria," J. Periodontol. 61:412–419.
Hamada et al. (1994), "Construction and Characterization of a fimA Mutant of *Porphyromonas gingivalis,*" Infect. Immun. 62:1696–1704.
Han, N. and Progulski–Fox, A. (1996), "The *P. gingivalis* 381 HagA Gene Contains 4 Contiguous Direct Repeats Each 1.35 kb in Length," J. Dent. Res. 75 (IADR Abstracts) #3225.

(List continued on next page.)

*Primary Examiner*—Nita Minnifield
*Attorney, Agent, or Firm*—Mueting, Raasch & Gebhardt, P.A.

[57] ABSTRACT

Provided herein are methods and immunogenic compositions useful for protecting mammals from infection and pathology of *P. gingivalis*. Specifically, arginine–specific proteases of *Porphyromonas gingivalis* and peptides derived therefrom offer protection against infection. Immunogenic compositions comprising a 50 kDa arginine–specific protease, the high molecular weight complex or peptides from one of the foregoing proteins are capable of protecting against *P. gingivalis* infection and/or gingivitis and/or periodontitis caused thereby in mammals, including humans.

7 Claims, 6 Drawing Sheets

OTHER PUBLICATIONS

Lamont et al. (1992), "Characterization of the adherence of *Porphyromonas gingivalis* to oral streptococci," Oral Microbiol. Immunol. 7:193–197.

Lamont et al. (1993), "Involvement of *Porphyromonas gingivalis* fimbriae in adherence to *Streptococcus gordonii*," Oral Microbiol. Immunol. 8:272–276.

Malek et al. (1994), "Inactivation of the *Porphyromonas gingivalis* fimA Gene Blocks Periodontal Damage in Bnotobiotic Rats," J. Bacteriol. 176:1052–1059.

McArthur and Clark (1993), "Specific Antibodies and Their Potential Role in Periodontal Diseases," J. Periodontol. 64:807–818.

Naito et al. (1987), "Detection of Specific Antibody in Adult Human periodontitis Sera to Surface Antigens of *Bacteriodes gingivalis*," Infect. Immun. 55:832–834.

Okamoto et al. (1996), "Cloning and Sequencing of the Gene Encoding a Novel Lysie–Specific Cysteine Proteinase (Lys–Gingipain) in *Porphyromonas gingivalis*: Structural Relationship with the Arginine–Specific Cysteine Proteinase (Arg–Gingipain)," J. Biochem. 120:398–406.

Pavloff et al. (1995), "Molecular Cloning and Structural Characterization of the Arg–gingipain Proteinase of *Porphyromonas gingivalis*," J. Biol. Chem. 270:1007–1010.

Pike et al. (1994), "Lysine– and Arginine–specific Proteinases from *Porphyromonas gingivalis*," J. Biol. Chem. 269:406–411.

Potempa, J. et al. (1995), "The Multiple Forms of Trypsin––like Activity Present in Various Strains of *Porphyromonas gingivalis* are due to the Presence of Either Arg–Gingipain or Lys–Ginigpain," Infect. Immun. 63(4):1176–1182.

Potempa, J. et al. (1995), "Host and *Porphyromonas gingivalis* proteinases in periodontitis: A biochemical model of infection and tissue destruction," Perspectives in Drug Discovery and Design 2:445–458.

Potempa, J. et al. (1995), "*Porphyromonas gingivalis*: a proteinase/gene accounting audit," Trends Microbiol. 3(11):430–434.

Tokuda et al. (1996), "Role of *Porphyromonas gingivalis* Protease Activity in Colonization of Oral Surfaces," Infect. Immun. 64:4067–4073.

Turner et al. (1989), "Serum and gingival tissue antibody levels to oral microbial antigens in human chronic adult periodontitis," Microbios 60:133–140.

Wingrove et al. (1992), "Activation of Complement Components C3 and C5 by a Cysteine Proteinase (Gingipain–1) from *Porphyromonas* (Bacteroides) *gingivalis*," J. Biol. chem. 267:18902–18907.

Yoshimura et al. (1987), Detection of Specific Antibodies Against Fimbriae and Membrane Proteins from the Oral Anaerobe *Bacteroides gingivalis* in Patients with Periodontal Diseases, Microbiol. Immunol. 31:935–941.

Arnott et al., "Cloning and Expression of *Porphyromonas* (Bacteroides) *gingivalis* Protease Gene in *Escherichia Coli*," Archs. Oral Biol., 35(7) Suppl., 97S–99S, (1990).

Barrett et al. "Cathepsin B, Cathepsin H, and Cathepsin L," *Methods in Enzymology, vol. 80, Proteolytic Enzymes*, Part C, Lorand, ed., Academic Press, New York, NY, pp. 535–561 (1981).

Birkedal–Hansen et al., "Characterization of Collagenolytic Activity from Strains of *Bacteroides gingivalis*," J. Periodont. Res., 23(4), 258–264 (1988).

Bourgeau et al., "Cloning, Expression, and Sequencing of a Protease Gene (tpr) from *Porphyromonas gingivalis* W83 in *Escherichia coli*," Infect. Immun., 60(8), 3186–3192 (1992).

Carlsson et al., "Degradation of the Human Proteinase Inhibitors Alpha–1–Antitrypsin and Alpha–2–Macroglobulin by *Bacteroides gingivalis*," Infect. Immun., 43(2), 644–648 (1984).

Carlsson et al., "Degradation of Albumin, Haemopexin, Haptoglobin and Transferrin, by Black–Pigmented Bacteroides Species," J. Med. Microbiol., 18, 39–46 (1984).

Chua et al., "Sequence Analysis of cDNA Coding for a Major House Dust Mite Allergen, Der p 1, Homology with Cysteine Proteases," J. Exp. Med., 167, 175–182 (1988).

Dayhoff et al,. "A Model of Evolutionary Change in Proteins," *Atlas of Protein Sequence and Structure*, National Biomedical Research Foundation, Washington, D.C., vol. 5, Suppl. 3, pp. 345–352 (1978).

Deutscher, ed., *Methods of Enzymology: vol. 182, Guide to Protein Purification*, Academic Press, Inc., San Diego, cover page and table of contents (1990).

Discipio et al., "Cleavage of Human Complement Component C5 by Cysteine Proteinases from *Porphyromonas* (Bacteroides) *gingivalis*. Prior Oxidation of C5 Augments Proteinase Digestion of C5," Immunology, 87(4), 660–667 (1996).

Fujimura et al., "Isolation and Characterization of a Protease from *Bacteroides gingivalis*," Infect. Immun., 55(3), 716–720 (1987).

Glover, ed., *DNA Cloning*, vol. I and II, IRL Press, Oxford, England, cover pages and tables of contents (1985).

Goding, *Monoclonal Antibodies: Principles and Practice*, 2d Ed., Academic Press, London (1986).

Grenier et al., "Isolation of a Membrane–Associated *Bacteroides gingivalis* Glycylprolyl Protease," Infect. Immun., 55(12), 3131–3136 (1987).

Grenier et al., "Selected Characteristics of Pathogenic and Nonpathogenic Strains of *Bacteroides gingivalis*," J. Clin. Microbiol., 25(4), 738–740 (1987).

Grenier et al., "Characterization of Sodium Dodecyl Sulfate–Stable *Bacteroides gingivalis* Proteases by Polyacrylamide Gel Electrophoresis," Infect. Immun., 57(1), 95–99 (1989).

Grøn et al., "The Potential Role of $\alpha_2$–Macroglobulin in the Control of Cysteine Proteinases (gingipains) from *Porphyromonas gingivalis*," J. Periodont. Res., 32(1), 61–68 (1997).

Grossman et al., ed., *Methods in Enzymology, vol. 65, Nucleic Acids*, Part I, Academic Press, New York, NY, cover page and table of contents (1980).

Hames et al., eds. *Nucleic Acid Hybridisation—A Practical Approach*, IRL Press, Oxford, England, cover page and table of contents (1985).

Harlow et al., *Antibodies: A Laboratory Manual*, Cold Spring Harbor Laboratories, Cold Spring Harbor, NY, cover page and table of contents (1988).

Herrmann et al., "Inactivation of Guinea–Pig Serum Proteinase Inhibitors by *Bacteroides gingivalis*," Scand. J. Dent. Res., 93(2), 153–157 (1985).

Holdeman et al., "Anaerobic Gram–Negative Straight, Curved and Helical Rods," *Bergey's Manual of Systematic Bacteriology*, vol. 1, Krieg et al., eds., The Williams & Wilkins Co., Baltimore, MD, pp. 602–631 (1984).

Hugli et al., "A Role for Complement in Gingivitis: Activation by a Cysteine Protease from *Porphyromonas gingivalis,*" *Clin. Exp. Immunol.*, 86, Suppl. 1, p. 20, Abstract 56 (1991).

Imamura et al., "Pathogenesis of Periodontitis: A Major Arginine–specific Cysteine Proteinase from *Porphyromonas gingivalis* Induces Vascular Permeability Enhancement Through Activation of the Kallikrein/Kinin Pathway," *J. Clin. Invest.*, 94, 361–367 (1994).

Kato et al., "Sequence Analysis and Characterization of the *Porphyromonas gingivalis* prtC Gene, Which Expresses a Novel Collagenase Activity," *J. Bacteriol.*, 174(12), 3889–3895 (1992).

Kilian, "Degradation of Immunoglobulins A1, A2, and G by Suspected Principal Periodontal Pathogens," *Infect. Immun.*, 34(3), 757–765 (1981).

Lantz et al., "Interactions of *Bacteroides gingivalis* with Fibrinogen," *Infect. Immun.*, 54(3), 654–658 (1986).

Lee et al., "Generation of cDNA Probes Directed by Amino Acid Sequence: Cloning of Urate Oxidase," *Science*, 239, 1288–1291 (1988).

Maniatis et al., *Molecular Cloning: A Laboratory Manual*, Cold Spring Harbor Laboratory, Cold Spring Harbor, NY, cover page and table of contents (1982).

Marsh et al., "Ultrastructure and Enzyme Activities of a Virulent and an Avirulent Variant of *Bacteroides gingivalie* W50," *FEMS Microbiol. Lett.*, 59, 181–186 (1989).

Merrifield, "Solid Phase Peptide Synthesis. I. The Synthesis of a Tetrapeptide," *J. Amer. Chem. Soc.*, 85, 2149–2154 (1963).

Merril et al., "Trace Polypeptides in Cellular Extracts and Human Body Fluids Detected by Two–dimensional Electrphoresis and a Highly Sensitive Silver Stain," *Proc. Natl. Acad. Sci. USA*, 76(9), 4335–4339 (1979).

Miller, ed., *Experiments in Molecular Genetics*, Cold Spring Harbor Laboratory, Cold Spring Harbor, NY, cover page and table of contents (1972).

Mikolajczyk–Pawlinska et al., "Molecular Cloning and Sequence Analysis of Arginine–Specific Cysteine Proteinase (gingipain R2, RGP–2) from *Porphyromonas gingivalis,*" Accession No. U85038 (1997).

Nakayama et al., "Construction and Characterization of Arginine–specific Cysteine Proteinase (Arg–gingipain)–deficient Mutants of *Porphyromonas gingivalis,*" *J. Biol. Chem.*, 270(40), 23619–23626 (1995).

Nakayama, "Domain–Specific Rearrangement Between the Two Arg–Gingipain–Encoding Genes in *Porphyromonas gingivalis*: Possible Involvement of Nonreciprocal Recombination," *Microbiol. Immunol.* 41(3), 185–196 (1997).

Nilsson et al., "Inactivation of Key Factors of the Plasma Proteinase Cascade Systems by *Bacteroides gingivalis,*" *Infect. Immun.*, 50(2), 467–471 (1985).

Nishikata et al., "Characterization of *Porphyromonas* (Bacteroides) *gingivalis* Hemagglutinin as a Protease," *Biochem. Biophys. Res. Comm.*, 178 (1), 336–342 (1991).

Nishikata et al., "Active Site Structure of a Hemagglutinating Protease From *Prophyromonas Gingivalis*:Similarity to Clostripain," *Biochem. Mole. Biol. Intl.*, 37(3), 547–553 (1995).

Old et al., *Prinicples of Gene Manipulation*, University of California Press, Berkeley, CA, cover page and table of contents (1981).

Ono et al., "Purification and Characterization of a Thiol–protease from *Bacteroides gingivalis* strain 381," *Oral Microbiol. Immunol.*, 2, 77–81 (187).

Otogoto et al. "Isolation and Characterization of the *Porphyromonas gingivalis* prT Gene, Coding for Protease Activity," *Infect. Immun.*, 61 (1), 117–123 (1993).

Otsuka et al., "Isolation and Characterization of Protease From Culture Supernatant of *Bacteroides gingivalis,*" *J. Periodont. Res.*, 22, 491–498 (1987).

Park et al., "Cloning of a *Porphyromonas* (Bacteroides) *gingivalis* Protease Gene and Characterization of its Product," *FEMS Microb. Lett.*, 92, 273–278 (1992).

Pavloff et al., "Molecular Cloning and Characteriation of *Porphyromonas gingivalis* Lysine–specific Gingipain," *J. Biol. Chem.*, 272(3), 1595–1600 (1997).

Posnett et al., "A Novel Method for Producing Anti–peptide Antibodies," *J. Biol. Chem.*, 263(4), 1719–1725 (1988).

Potempa et al., "Purification and Characterization of a 50 kD Cysteine Proteinase of *Porphyromonas gingivalis,*" *FASEB J.*, 54(4), A829, Abstract 2667 (1991).

Potempa et al., "*Porphyromonas gingivalis* Proteinases in Periodontitis, a Review," *Acta Biochimica Polonica* 43(3), 455–466 (1996).

Pratt et al., "Identification of Gene Products Programmed by Restriction Endonuclease DNA Fragments Using an *E. coli* in vitro System," *Nucleic Acids Res.*, 9(18), 4459–4474 (1981).

Rangarajan et al., "Biochemical Characterization of the Arginine–Specific Proteases of *Porphyromonas gingivalis* W50 Suggests a Common Precursor," *Biochem. J. 323*, 701–709 (1997).

Roberts et al., "Purfification of the Secreted Thiol–activated Protease of *Porphyromonas* (Bacteroides) *gingivalis* and the cloning and Expression of the Gene in *Escherichia coli,*" *Clinical & Molecular Aspects of Anaerobes*, S.P. Borriello, ed., Wrightson Biomedical Publishing Ltd., Petersfield, U.K., pp. 227–233 (1990).

Saglie et al., "Intragingival Occurrence of *Actinobacillus actinomycetemcomitans* and *Bacteroides gingivalis* in Active Destructive Periodontal Lesions," *J. Periodont*, 59(4), 259–265 (1988).

Sambrook et al., *Molecular Cloning—A Laboratory Manual, 2nd Ed.*, Cold Spring Harbor Laboratory Press, Cold Spring Harbor, NY, cover page and table of contents (1989).

Sato et al., "Degradation of Human Secretory Immunoglobulin A By Protease Isolated From the Anaerobic Periodontopathogenic Bacterium, *Bacteroides gingivalis,*" *Arch. Oral Biol.*, 32(4), 235–238 (1987).

Schägger et al., "Tricine–Sodium Dodecyl Sulfate–Polyacrylamide Gel Electrophoresis for the Separation of Proteins in the Range from 1 to 100kDa," *Analyt. Biochem.*, 166, 368–379 (1987).

Schenkien, "The Effect of Periodontal Proteolytic Bacteroides Species on Proteins of the Human Complement System," *J. Periodont. Res.*, 23(3), 187–192 (1988).

Schleif et al., *Practical Methods in Molecular Biology*, Springer–Verlag New York Inc., New York, NY, cover page and table of contents (1981).

Scopes, *Protein Purification: Principles and Practice*, Springer–Verlag New York, Inc., New York, NY, cover pages and table of content (1982).

Setlow et al., *Genetic Engineering: Principles and Methods*, Vols. 1–4, Plenum Press, New York, NY, cover pages and table of content (1979).

Shah et al., "Evidence for Independent Molecular Identity and Functional Interaction of the Haemagglutinin and Cysteine Proteinase (gingivain) of *Porphyromonas gingivalis*," *J. Med. Microbiol.*, 36(1), 239–244 (1992).

Slakeski et al., "Characterization of a *Porphyromonas gingivalis* Gene prtR That Encodes an Arginine–Specific Thiol Proteinase and Multiple Adhesins," *Biochem. Biophysical Res. Comm.*, 224, 605–610 (1996).

Smalley et al., "The Distribution of Trypsin–like Enzyme Activity in Cultures of a Virulent and an Avirulent Strain of *Bacteroides gingivalis* W50," *Oral Microbiol. Immun.*, 4(3), 178–181 (1989).

Sorsa et al., "A Trypsin–like Protease from *Bacteroides gingivalis*: Partial Purfication and Characterization," *J. Periodont. Res.*, 22(5), 375–380 (1987).

Suido et al., "Characterization of N–CBz–glycyl–glycyl–arginyl peptidase and glycyl–prolyl peptidase of *Bacteroides gingivalis*," *J. Periodont. Res.*, 22(5), 412–418 (1987).

Sundqvist et al., "Degradation of Human Immunoglobulins G and M and Complement Factors C3 and C5 by Black–Pigmented Bacteroides," *J. Med. Microbiol.*, 19, 85–94 (1985).

Sundqvist et al., "Collagenolytic Activity of Black–Pigmented Bacteroides Species," *J. Periodont. Res.*, 22(4), 300–306 (1987).

Takahashi et al., "Isolation and Preliminary Characterization of the *Porphyromonas gingivalis* prtC Gene Expressing Collagenase Activity," *FEMS Microbiol. Lett.*, 84, 135–138 (1991).

Tam, "Synthetic Peptide Vaccine Design: Synthesis and Properties of a High–density Multiple Antigenic Peptide System," *Proc. Natl. Acad. Sci. USA*, 85, 5409–5413 (1988).

Travis et al., "Bacterial Proteinases in Periodontal Disease," *J. Cell Biochem.*, Suppl. 15G, 117, Abstract CH 027 (1991).

Travis et al., "Are Bacterial Proteinase Pathogenic Factors?" *Trends in Microbiology*, 3(10) 405–407 (1995).

Travis et al., "*Porphyromonas gingivalis* Proteinases as Virulence Factors in the Development of Periodontitis," *J. Periodont. Res.*, 32, 120–125 (1997).

Tsutsui et al., "Purification and Characterization of a Protease from *Bacteroides gingivalis* 381," *Infect. Immun.*, 55(2), 420–427 (1987).

Uitto et al., "A Protease of *Bacteroides gingivalis* Degrades Cell Surface and Matrix Glycoproteins of Cultured Gingival Fibroblasts and Induces Secretion of Collagenase and Plasminogen Activator," *Infect. Immun.*, 57(1), 213–218 (1989).

Uitto, "Human Gingival Proteases. I: Extraction and Preliminary Characterization of Trypsin–like and Elastase–like Enzymes," *J. Periodont. Res.*, 22(1), 58–63 (1987).

Wikstrom et al., "Ability of Oral Bacteria to Degrade Fibronectin," *Infect. Immun.*, 51(2), 707–711 (1986).

Wikstrom et al., "Fibrinogenolytic and Fibrinolytic Activity in Oral Microorganisms," *J. Clin. Microbiol.*, 17(5), 759–767 (1983).

Wikstrom et al., "Detection of *Porphyromonas gingivalis* in Gingival Exudate by a Dipeptide–Enhanced Trypsin–Like Activity," *J. Periodont.*, 65, 47–55 (1994).

Wu, ed., *Methods in Enzymology, vol. 68, Recombinant DNA*, Academic Press, Inc., New York, NY, cover page and table of contents (1979).

Wu et al., ed. *Methods in Enzymology, vol. 100, Recombinant DNA*, Part B, Academic Press, Inc., New York, NY, cover page and table of contents (1983).

Wu et al., ed. *Methods in Enzymology, vol. 101, Recombinant DNA*, Part C, Academic Press, Inc., New York, NY, cover page and table of contents (1983).

Wu et al., ed. *Methods in Enzymology, vol. 218, Recombinant DNA*, Part I, Academic Press, Inc., San Diego, CA, cover page and table of contents (1983).

Yoshimura et al., "Characterization of a Trypsin–Like Protease From the Bacterium *Bacteroides gingivalis* Isolated from Human Dental Plaque," *Archs. Oral Biol.*, 29(7), 559–564 (1984).

Alignment of the amino acid sequence of catalytic domains

```
RGP  ----YTPVEEKGNG-IRMIVIAKKYEGDIKDFVDWKNQRGLRTEVKVAEDI    46
KGP  DVYTDHGDLYNTPVRMLVVAGAKFKEALKPWLTWKAQKGFYLDVHYTDEA    50

RGP  ASPVTANAIQQFVKQEYEKEGNDLTYVILVLVGDIPAKITPGIKSDQVV    95
KGP  EVGTTNASIKAFIHKKYNDGLAATAAPVFLALVGDTDVISGEKGKKTKKVV   105

RGP  ---YGQIVGNDHYFPEMYTGRFSCESKEDLKTQIDRTIHYERNITTEDRW   141
KGP  TDLYYTAVDGDYFPEMYTGRFMSASSPEELTNIIDKVLMYEKATMPDKSY   143

RGP  LGQALCIASAEGGPSADNGESDIQHENVIANLTQYGYTKIIKCYDPGVT    191
KGP  LEKALLIAGADSYWNPKIGQGTI-KYAVQYYYNQADHGYTDVYTYPKAPYT  198

RGP  PKCYSHL--IDAFNGTGIVGLVNYTVHGSETAWGTSHFGTTHVKQLPFLAIG  241
KGP  GCYNIDI--NTNGGVGLFANYTVHGSETSWADPSVTATQVKALTNKNKYFLAIG  246

RGP  VACVNGDFLFSMPCFAEALMRAQKDGKPTGTVAILASTINGSWASPMRGGQ   291
KGP  NCCVTAQFDYPQCFGEVMTRVKEKGAYAYLGSSPNSYWGEDYYWSVGAN    296

RGP  DEMNEILCEKHPNNIKRTFGGVTMNGMFAMVEKYKKDI-IHAENLGNVT    320
KGP  AVFGVQPTFEGTSMGSYDATFLEDSYNTAPAQINLTDASVNLAATHAEGNLAIG   346

RGP  --GEKMLDTWTHVFGDPSLLVRTLVPTKMQVTAPAQINLTPAS        375
KGP  HIGAHYYWEAYHVLGDADGSVMPYRAMPKTNTYTLPASLPQNQASYSIQASA  396

RGP  NGAIATISANGKMFGSAVVE-NGTATINLTGLTNESTLTVVGY-NKET   423
KGP  GSYVA--IISKDGVLYGTGVANASGVATVNMTKQITENGNYDVVITRSNYLP  445

RGP  VIKTINTNGEPNPYQPVSNLTATTQGQKVTLKWDAPSTK-TNATTNTARS    472
KGP  VIKEIQA-GEPSPYQPVSNLTATTQGQKVTLKWDAPSAKKAEGSREVKRI   494

RGP  VDGIRELVLSVSDAPELLR                                  493
KGP  GDGLFVTIEPANDVR                                      510
```

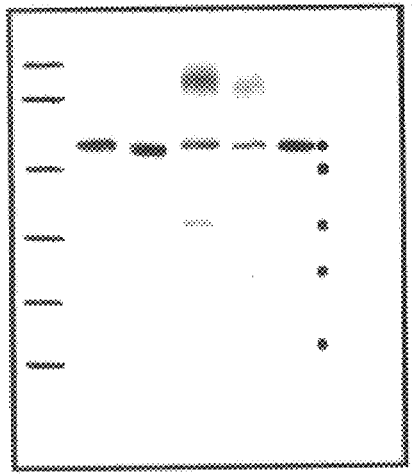
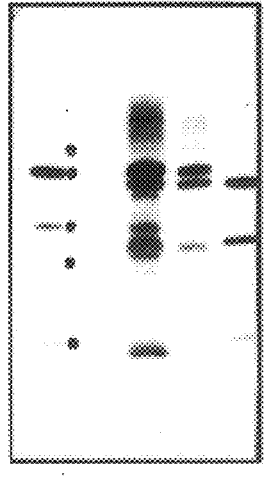
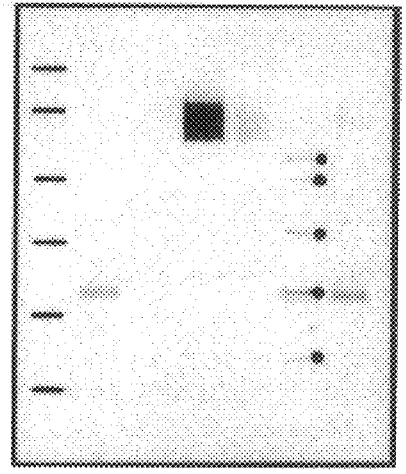
FIG. 6A  FIG. 6B  FIG. 6C
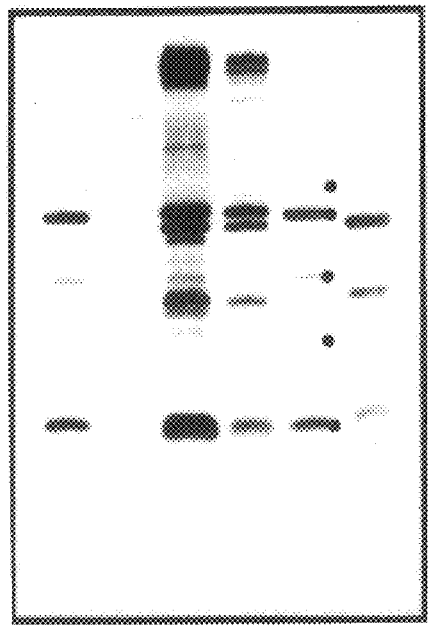
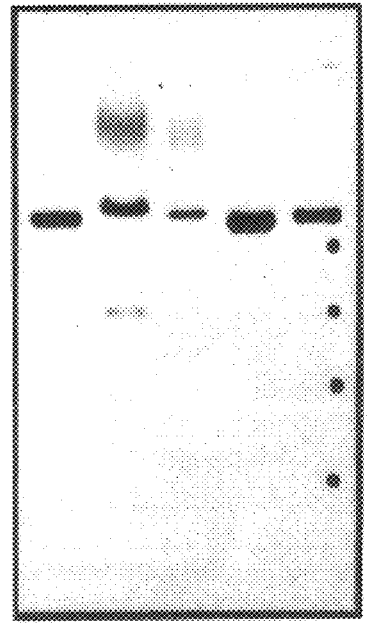
FIG. 6D  FIG. 6E 6,129,917

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
      (A) LENGTH: 34 amino acids
      (B) TYPE: amino acid
      (C) STRANDEDNESS: Not Relevant
      (D) TOPOLOGY: unknown (ii) MOLECULE TYPE: protein (iii) HYPOTHETICAL: NO (v) FRAGMENT TYPE: N-terminal (ix) FEATURE:
      (A) NAME/KEY: Region
      (B) LOCATION: 38..43
      (D) OTHER INFORMATION: /product= "Xaa"
          /label= Xaa
          /note= "Xaa is used to denote an amino acid which could
          not be identified with certainty."

(xi) SEQUENCE DESCRIPTION: SEQ ID NO:1:

```
Tyr Thr Pro Val Glu Glu Lys Gln Asn Gly Arg Met Ile Val Ile Val
 1               5                  10                  15

Ala Lys Lys Tyr Glu Gly Asp Ile Lys Asp Phe Val Asp Trp Lys Asn
                20                  25                  30

Gln Arg
```

(2) INFORMATION FOR SEQ ID NO:2:

-continued

```
    (i) SEQUENCE CHARACTERISTICS:
        (A) LENGTH: 4 amino acids
        (B) TYPE: amino acid
        (C) STRANDEDNESS: Not Relevant
        (D) TOPOLOGY: unknown (ii) MOLECULE TYPE: protein (iii) HYPOTHETICAL: NO (v) FRAGMENT TYPE: C-terminal (xi) SEQUENCE DESCRIPTION: SEQ ID NO:2:

Glu Leu Leu Arg
1

(2) INFORMATION FOR SEQ ID NO:3:

(i) SEQUENCE CHARACTERISTICS:
        (A) LENGTH: 3159 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Porphryomonas gingivalis (ix) FEATURE:
        (A) NAME/KEY: CDS
        (B) LOCATION: 949..3159

(xi) SEQUENCE DESCRIPTION: SEQ ID NO:3:
```

| | | |
|---|---|---|
| CTGCAGAGGG CTGGTAAAGA CCGCCTCGGG ATCGAGGCCT TTGAGACGGG CACAAGCCGC | 60 |
| CGCAGCCTCC TCTTCGAAGG TGTCTCGAAC GTCCACATCG GTGAATCCGT AGCAGTGCTC | 120 |
| ATTGCCATTG AGCAGCACCG AGGTGTGGCG CATCAGATAT ATTTTCATCA GTGGATTATT | 180 |
| AGGGTATCGG TCAGAAAAAG CCTTCCGAAT CCGACAAAGA TAGTAGAAAG AGAGTGCATC | 240 |
| TGAAAACAGA TCATTCGAGG ATTATCGATC AACTGAAAAG GCAGGAGTTG TTTTGCGTTT | 300 |
| TGGTTCGGAA AATTACCTGA TCAGCATTCG TAAAAACGTG GCGCGAGAAT TTTTTCGTTT | 360 |
| TGGCGCGAGA ATTAAAAATT TTTGGAACCA CAGCGAAAAA AATCTCGCGC CGTTTTCTCA | 420 |
| GGATTTACAG ACCACAATCC GAGCATTTTC GGTTCGTAAT TCATCGAAGA GACAGGTTTT | 480 |
| ACCGCATTGA AATCAGAGAG AGAATATCCG TAGTCCAACG GTTCATCCTT ATATCAGAGG | 540 |
| TTAAAAGATA TGGTACGCTC ATCGAGGAGC TGATTGGCTT AGTAGGTGAG ACTTTCTTAA | 600 |
| GAGACTATCG GCACCTACAG GAAGTTCATG GCACACAAGG CAAAGGAGGC AATCTTCGCA | 660 |
| GACCGGACTC ATATCAAAAG GATGAAACGA CTTTTCCATA CGACAACCAA ATAGCCGTCT | 720 |
| ACGGTAGACG AATGCAAACC CAATATGAGG CCATCAATCA ATCCGAATGA CAGCTTTTGG | 780 |
| GCAATATATT ATGCATATTT TGATTCGCGT TTAAAGGAAA AGTGCATATA TTTGCGATTG | 840 |
| TGGTATTTCT TTCGGTTTCT ATGTGAATTT TGTCTCCCAA GAAGACTTTA TAATGCATAA | 900 |
| ATACAGAAGG GGTACTACAC AGTAAAATCA TATTCTAATT TCATCAAA ATG AAA AAC | 957 |
|                                                                                                                                Met Lys Asn<br>                                                                                                                                   1 | |
| TTG AAC AAG TTT GTT TCG ATT GCT CTT TGC TCT TCC TTA TTA GGA GGA<br>Leu Asn Lys Phe Val Ser Ile Ala Leu Cys Ser Ser Leu Leu Gly Gly<br>    5                    10                  15 | 1005 |

-continued

```
ATG GCA TTT GCG CAG CAG ACA GAG TTG GGA CGC AAT CCG AAT GTC AGA      1053
Met Ala Phe Ala Gln Gln Thr Glu Leu Gly Arg Asn Pro Asn Val Arg
 20              25                  30                  35

TTG CTC GAA TCC ACT CAG CAA TCG GTG ACA AAG GTT CAG TTC CGT ATG      1101
Leu Leu Glu Ser Thr Gln Gln Ser Val Thr Lys Val Gln Phe Arg Met
                 40                  45                  50

GAC AAC CTC AAG TTC ACC GAA GTT CAA ACC CCT AAG GGA ATC GGA CAA      1149
Asp Asn Leu Lys Phe Thr Glu Val Gln Thr Pro Lys Gly Ile Gly Gln
             55                  60                  65

GTG CCG ACC TAT ACA GAA GGG GTT AAT CTT TCC GAA AAA GGG ATG CCT      1197
Val Pro Thr Tyr Thr Glu Gly Val Asn Leu Ser Glu Lys Gly Met Pro
         70                  75                  80

ACG CTT CCC ATT CTA TCA CGC TCT TTG GCG GTT TCA GAC ACT CGT GAG      1245
Thr Leu Pro Ile Leu Ser Arg Ser Leu Ala Val Ser Asp Thr Arg Glu
     85                  90                  95

ATG AAG GTA GAG GTT GTT TCC TCA AAG TTC ATC GAA AAG AAA AAT GTC      1293
Met Lys Val Glu Val Val Ser Ser Lys Phe Ile Glu Lys Lys Asn Val
100                 105                 110                 115

CTG ATT GCA CCC TCC AAG GGC ATG ATT ATG CGT AAC GAA GAT CCG AAA      1341
Leu Ile Ala Pro Ser Lys Gly Met Ile Met Arg Asn Glu Asp Pro Lys
                120                 125                 130

AAG ATC CCT TAC GTT TAT GGA AAG AGC TAC TCG CAA AAC AAA TTC TTC      1389
Lys Ile Pro Tyr Val Tyr Gly Lys Ser Tyr Ser Gln Asn Lys Phe Phe
            135                 140                 145

CCG GGA GAG ATC GCC ACG CTT GAT GAT CCT TTT ATC CTT CGT GAT GTG      1437
Pro Gly Glu Ile Ala Thr Leu Asp Asp Pro Phe Ile Leu Arg Asp Val
        150                 155                 160

CGT GGA CAG GTT GTA AAC TTT GCG CCT TTG CAG TAT AAC CCT GTG ACA      1485
Arg Gly Gln Val Val Asn Phe Ala Pro Leu Gln Tyr Asn Pro Val Thr
    165                 170                 175

AAG ACG TTG CGC ATC TAT ACG GAA ATC ACT GTG GCA GTG AGC GAA ACT      1533
Lys Thr Leu Arg Ile Tyr Thr Glu Ile Thr Val Ala Val Ser Glu Thr
180                 185                 190                 195

TCG GAA CAA GGC AAA AAT ATT CTG AAC AAG AAA GGT ACA TTT GCC GGC      1581
Ser Glu Gln Gly Lys Asn Ile Leu Asn Lys Lys Gly Thr Phe Ala Gly
                200                 205                 210

TTT GAA GAC ACA TAC AAG CGC ATG TTC ATG AAC TAC GAG CCG GGG CGT      1629
Phe Glu Asp Thr Tyr Lys Arg Met Phe Met Asn Tyr Glu Pro Gly Arg
            215                 220                 225

TAC ACA CCG GTA GAG GAA AAA CAA AAT GGT CGT ATG ATC GTC ATC GTA      1677
Tyr Thr Pro Val Glu Glu Lys Gln Asn Gly Arg Met Ile Val Ile Val
        230                 235                 240

GCC AAA AAG TAT GAG GGA GAT ATT AAA GAT TTC GTT GAT TGG AAA AAC      1725
Ala Lys Lys Tyr Glu Gly Asp Ile Lys Asp Phe Val Asp Trp Lys Asn
    245                 250                 255

CAA CGC GGT CTC CGT ACC GAG GTG AAA GTG GCA GAA GAT ATT GCT TCT      1773
Gln Arg Gly Leu Arg Thr Glu Val Lys Val Ala Glu Asp Ile Ala Ser
260                 265                 270                 275

CCC GTT ACA GCT AAT GCT ATT CAG CAG TTC GTT AAG CAA GAA TAC GAG      1821
Pro Val Thr Ala Asn Ala Ile Gln Gln Phe Val Lys Gln Glu Tyr Glu
                280                 285                 290

AAA GAA GGT AAT GAT TTG ACC TAT GTT CTT TTG GTT GGC GAT CAC AAA      1869
Lys Glu Gly Asn Asp Leu Thr Tyr Val Leu Leu Val Gly Asp His Lys
            295                 300                 305

GAT ATT CCT GCC AAA ATT ACT CCG GGG ATC AAA TCC GAC CAG GTA TAT      1917
Asp Ile Pro Ala Lys Ile Thr Pro Gly Ile Lys Ser Asp Gln Val Tyr
        310                 315                 320

GGA CAA ATA GTA GGT AAT GAC CAC TAC AAC GAA GTC TTC ATC GGT CGT      1965
Gly Gln Ile Val Gly Asn Asp His Tyr Asn Glu Val Phe Ile Gly Arg
```

```
                    325                 330                 335
TTC TCA TGT GAG AGC AAA GAG GAT CTG AAG ACA CAA ATC GAT CGG ACT    2013
Phe Ser Cys Glu Ser Lys Glu Asp Leu Lys Thr Gln Ile Asp Arg Thr
340                 345                 350                 355

ATT CAC TAT GAG CGC AAT ATA ACC ACG GAA GAC AAA TGG CTC GGT CAG    2061
Ile His Tyr Glu Arg Asn Ile Thr Thr Glu Asp Lys Trp Leu Gly Gln
                    360                 365                 370

GCT CTT TGT ATT GCT TCG GCT GAA GGA GGC CCA TCC GCA GAC AAT GGT    2109
Ala Leu Cys Ile Ala Ser Ala Glu Gly Gly Pro Ser Ala Asp Asn Gly
                375                 380                 385

GAA AGT GAT ATC CAG CAT GAG AAT GTA ATC GCC AAT CTG CTT ACC CAG    2157
Glu Ser Asp Ile Gln His Glu Asn Val Ile Ala Asn Leu Leu Thr Gln
            390                 395                 400

TAT GGC TAT ACC AAG ATT ATC AAA TGT TAT GAT CCG GGA GTA ACT CCT    2205
Tyr Gly Tyr Thr Lys Ile Ile Lys Cys Tyr Asp Pro Gly Val Thr Pro
        405                 410                 415

AAA AAC ATT ATT GAT GCT TTC AAC GGA GGA ATC TCG TTG GTC AAC TAT    2253
Lys Asn Ile Ile Asp Ala Phe Asn Gly Gly Ile Ser Leu Val Asn Tyr
420                 425                 430                 435

ACG GGC CAC GGT AGC GAA ACA GCT TGG GGT ACG TCT CAC TTC GGC ACC    2301
Thr Gly His Gly Ser Glu Thr Ala Trp Gly Thr Ser His Phe Gly Thr
                    440                 445                 450

ACT CAT GTG AAG CAG CTT ACC AAC AGC AAC CAG CTA CCG TTT ATT TTC    2349
Thr His Val Lys Gln Leu Thr Asn Ser Asn Gln Leu Pro Phe Ile Phe
                455                 460                 465

GAC GTA GCT TGT GTG AAT GGC GAT TTC CTA TTC AGC ATG CCT TGC TTC    2397
Asp Val Ala Cys Val Asn Gly Asp Phe Leu Phe Ser Met Pro Cys Phe
            470                 475                 480

GCA GAA GCC CTG ATG CGT GCA CAA AAA GAT GGT AAG CCG ACA GGT ACT    2445
Ala Glu Ala Leu Met Arg Ala Gln Lys Asp Gly Lys Pro Thr Gly Thr
485                 490                 495

GTT GCT ATC ATA GCG TCT ACG ATC AAC CAG TCT TGG GCT TCT CCT ATG    2493
Val Ala Ile Ile Ala Ser Thr Ile Asn Gln Ser Trp Ala Ser Pro Met
500                 505                 510                 515

CGC GGG CAG GAT GAG ATG AAC GAA ATT CTG TGC GAA AAA CAC CCG AAC    2541
Arg Gly Gln Asp Glu Met Asn Glu Ile Leu Cys Glu Lys His Pro Asn
                    520                 525                 530

AAC ATC AAG CGT ACT TTC GGT GGT GTC ACC ATG AAC GGT ATG TTT GCT    2589
Asn Ile Lys Arg Thr Phe Gly Gly Val Thr Met Asn Gly Met Phe Ala
                535                 540                 545

ATG GTG GAA AAG TAT AAA AAG GAT GGT GAG AAG ATG CTC GAC ACA TGG    2637
Met Val Glu Lys Tyr Lys Lys Asp Gly Glu Lys Met Leu Asp Thr Trp
            550                 555                 560

ACT GTT TTC GGC GAC CCC TCG CTG CTC GTT CGT ACA CTT GTC CCG ACC    2685
Thr Val Phe Gly Asp Pro Ser Leu Leu Val Arg Thr Leu Val Pro Thr
        565                 570                 575

AAA ATG CAG GTT ACG GCT CCG GCT CAG ATT AAT TTG ACG GAT GCT TCA    2733
Lys Met Gln Val Thr Ala Pro Ala Gln Ile Asn Leu Thr Asp Ala Ser
580                 585                 590                 595

GTC AAC GTA TCT TGC GAT TAT AAT GGT GCT ATT GCT ACC ATT TCA GCC    2781
Val Asn Val Ser Cys Asp Tyr Asn Gly Ala Ile Ala Thr Ile Ser Ala
                    600                 605                 610

AAT GGA AAG ATG TTC GGT TCT GCA GTT GTC GAA AAT GGA ACA GCT ACA    2829
Asn Gly Lys Met Phe Gly Ser Ala Val Val Glu Asn Gly Thr Ala Thr
                615                 620                 625

ATC AAT CTG ACA GGT CTG ACA AAT GAA AGC ACG CTT ACC CTT ACA GTA    2877
Ile Asn Leu Thr Gly Leu Thr Asn Glu Ser Thr Leu Thr Leu Thr Val
            630                 635                 640

GTT GGT TAC AAC AAA GAG ACG GTT ATT AAG ACC ATC AAC ACT AAT GGT    2925
```

```
Val Gly Tyr Asn Lys Glu Thr Val Ile Lys Thr Ile Asn Thr Asn Gly
    645                 650                 655

GAG CCT AAC CCC TAC CAG CCC GTT TCC AAC TTG ACA GCT ACA ACG CAG           2973
Glu Pro Asn Pro Tyr Gln Pro Val Ser Asn Leu Thr Ala Thr Thr Gln
660                 665                 670                 675

GGT CAG AAA GTA ACG CTC AAG TGG GAT GCA CCG AGC ACG AAA ACC AAT           3021
Gly Gln Lys Val Thr Leu Lys Trp Asp Ala Pro Ser Thr Lys Thr Asn
                680                 685                 690

GCA ACC ACT AAT ACC GCT CGC AGC GTG GAT GGC ATA CGA GAA TTG GTT           3069
Ala Thr Thr Asn Thr Ala Arg Ser Val Asp Gly Ile Arg Glu Leu Val
                695                 700                 705

CTT CTG TCA GTC AGC GAT GCC CCC GAA CTT CTT CGC AGC GGT CAG GCC           3117
Leu Leu Ser Val Ser Asp Ala Pro Glu Leu Leu Arg Ser Gly Gln Ala
                710                 715                 720

GAG ATT GTT CTT GAA GCT CAC GAT GTT TGG AAT GAT GGA TCC                   3159
Glu Ile Val Leu Glu Ala His Asp Val Trp Asn Asp Gly Ser
725                 730                 735
```

(2) INFORMATION FOR SEQ ID NO:4:

(i) SEQUENCE CHARACTERISTICS:
        (A) LENGTH: 737 amino acids
        (B) TYPE: amino acid
        (D) TOPOLOGY: linear (ii) MOLECULE TYPE: protein (xi) SEQUENCE DESCRIPTION: SEQ ID NO:4:

```
Met Lys Asn Leu Asn Lys Phe Val Ser Ile Ala Leu Cys Ser Ser Leu
  1               5                  10                  15

Leu Gly Gly Met Ala Phe Ala Gln Gln Thr Glu Leu Gly Arg Asn Pro
                20                  25                  30

Asn Val Arg Leu Leu Glu Ser Thr Gln Gln Ser Val Thr Lys Val Gln
            35                  40                  45

Phe Arg Met Asp Asn Leu Lys Phe Thr Glu Val Gln Thr Pro Lys Gly
 50                  55                  60

Ile Gly Gln Val Pro Thr Tyr Thr Glu Gly Val Asn Leu Ser Glu Lys
 65                  70                  75                  80

Gly Met Pro Thr Leu Pro Ile Leu Ser Arg Ser Leu Ala Val Ser Asp
                 85                  90                  95

Thr Arg Glu Met Lys Val Glu Val Ser Ser Lys Phe Ile Glu Lys
                100                 105                 110

Lys Asn Val Leu Ile Ala Pro Ser Lys Gly Met Ile Met Arg Asn Glu
            115                 120                 125

Asp Pro Lys Lys Ile Pro Tyr Val Tyr Gly Lys Ser Tyr Ser Gln Asn
130                 135                 140

Lys Phe Phe Pro Gly Glu Ile Ala Thr Leu Asp Asp Pro Phe Ile Leu
145                 150                 155                 160

Arg Asp Val Arg Gly Gln Val Val Asn Phe Ala Pro Leu Gln Tyr Asn
                165                 170                 175

Pro Val Thr Lys Thr Leu Arg Ile Tyr Thr Glu Ile Thr Val Ala Val
                180                 185                 190

Ser Glu Thr Ser Glu Gln Gly Lys Asn Ile Leu Asn Lys Lys Gly Thr
            195                 200                 205

Phe Ala Gly Phe Glu Asp Thr Tyr Lys Arg Met Phe Met Asn Tyr Glu
210                 215                 220

Pro Gly Arg Tyr Thr Pro Val Glu Glu Lys Gln Asn Gly Arg Met Ile
225                 230                 235                 240
```

-continued

```
Val Ile Val Ala Lys Lys Tyr Glu Gly Asp Ile Lys Asp Phe Val Asp
            245                 250                 255

Trp Lys Asn Gln Arg Gly Leu Arg Thr Glu Val Lys Val Ala Glu Asp
            260                 265                 270

Ile Ala Ser Pro Val Thr Ala Asn Ala Ile Gln Gln Phe Val Lys Gln
            275                 280                 285

Glu Tyr Glu Lys Glu Gly Asn Asp Leu Thr Tyr Val Leu Leu Val Gly
            290                 295                 300

Asp His Lys Asp Ile Pro Ala Lys Ile Thr Pro Gly Ile Lys Ser Asp
305                 310                 315                 320

Gln Val Tyr Gly Gln Ile Val Gly Asn Asp His Tyr Asn Glu Val Phe
            325                 330                 335

Ile Gly Arg Phe Ser Cys Glu Ser Lys Glu Asp Leu Lys Thr Gln Ile
            340                 345                 350

Asp Arg Thr Ile His Tyr Glu Arg Asn Ile Thr Thr Glu Asp Lys Trp
            355                 360                 365

Leu Gly Gln Ala Leu Cys Ile Ala Ser Ala Glu Gly Gly Pro Ser Ala
            370                 375                 380

Asp Asn Gly Glu Ser Asp Ile Gln His Glu Asn Val Ile Ala Asn Leu
385                 390                 395                 400

Leu Thr Gln Tyr Gly Tyr Thr Lys Ile Ile Lys Cys Tyr Asp Pro Gly
            405                 410                 415

Val Thr Pro Lys Asn Ile Ile Asp Ala Phe Asn Gly Gly Ile Ser Leu
            420                 425                 430

Val Asn Tyr Thr Gly His Gly Ser Glu Thr Ala Trp Gly Thr Ser His
            435                 440                 445

Phe Gly Thr Thr His Val Lys Gln Leu Thr Asn Ser Asn Gln Leu Pro
            450                 455                 460

Phe Ile Phe Asp Val Ala Cys Val Asn Gly Asp Phe Leu Phe Ser Met
465                 470                 475                 480

Pro Cys Phe Ala Glu Ala Leu Met Arg Ala Gln Lys Asp Gly Lys Pro
            485                 490                 495

Thr Gly Thr Val Ala Ile Ile Ala Ser Thr Ile Asn Gln Ser Trp Ala
            500                 505                 510

Ser Pro Met Arg Gly Gln Asp Glu Met Asn Glu Ile Leu Cys Glu Lys
            515                 520                 525

His Pro Asn Asn Ile Lys Arg Thr Phe Gly Gly Val Thr Met Asn Gly
            530                 535                 540

Met Phe Ala Met Val Glu Lys Tyr Lys Lys Asp Gly Glu Lys Met Leu
545                 550                 555                 560

Asp Thr Trp Thr Val Phe Gly Asp Pro Ser Leu Leu Val Arg Thr Leu
            565                 570                 575

Val Pro Thr Lys Met Gln Val Thr Ala Pro Ala Gln Ile Asn Leu Thr
            580                 585                 590

Asp Ala Ser Val Asn Val Ser Cys Asp Tyr Asn Gly Ala Ile Ala Thr
            595                 600                 605

Ile Ser Ala Asn Gly Lys Met Phe Gly Ser Ala Val Val Glu Asn Gly
            610                 615                 620

Thr Ala Thr Ile Asn Leu Thr Gly Leu Thr Asn Glu Ser Thr Leu Thr
625                 630                 635                 640

Leu Thr Val Val Gly Tyr Asn Lys Glu Thr Val Ile Lys Thr Ile Asn
            645                 650                 655
```

```
Thr Asn Gly Glu Pro Asn Pro Tyr Gln Pro Val Ser Asn Leu Thr Ala
            660                 665                 670

Thr Thr Gln Gly Gln Lys Val Thr Leu Lys Trp Asp Ala Pro Ser Thr
        675                 680                 685

Lys Thr Asn Ala Thr Thr Asn Thr Ala Arg Ser Val Asp Gly Ile Arg
    690                 695                 700

Glu Leu Val Leu Leu Ser Val Ser Asp Ala Pro Glu Leu Leu Arg Ser
705                 710                 715                 720

Gly Gln Ala Glu Ile Val Leu Glu Ala His Asp Val Trp Asn Asp Gly
                725                 730                 735

Ser
```

(2) INFORMATION FOR SEQ ID NO:5:

(i) SEQUENCE CHARACTERISTICS:
        (A) LENGTH: 7266 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (A) ORGANISM: Porphyromonas gingivalis (ix) FEATURE:
        (A) NAME/KEY: CDS
        (B) LOCATION: 949..6063

(xi) SEQUENCE DESCRIPTION: SEQ ID NO:5:

```
CTGCAGAGGG CTGGTAAAGA CCGCCTCGGG ATCGAGGCCT TTGAGACGGG CACAAGCCGC      60

CGCAGCCTCC TCTTCGAAGG TGTCTCGAAC GTCCACATCG GTGAATCCGT AGCAGTGCTC     120

ATTGCCATTG AGCAGCACCG AGGTGTGGCG CATCAGATAT ATTTTCATCA GTGGATTATT     180

AGGGTATCGG TCAGAAAAAG CCTTCCGAAT CCGACAAAGA TAGTAGAAAG AGAGTGCATC     240

TGAAAACAGA TCATTCGAGG ATTATCGATC AACTGAAAAG GCAGGAGTTG TTTTGCGTTT     300

TGGTTCGGAA AATTACCTGA TCAGCATTCG TAAAAACGTG GCGCGAGAAT TTTTTCGTTT     360

TGGCGCGAGA ATTAAAAATT TTTGGAACCA CAGCGAAAAA AATCTCGCGC CGTTTTCTCA     420

GGATTTACAG ACCACAATCC GAGCATTTTC GGTTCGTAAT TCATCGAAGA GACAGGTTTT     480

ACCGCATTGA AATCAGAGAG AGAATATCCG TAGTCCAACG GTTCATCCTT ATATCAGAGG     540

TTAAAGATA TGGTACGCTC ATCGAGGAGC TGATTGGCTT AGTAGGTGAG ACTTTCTTAA      600

GAGACTATCG GCACCTACAG GAAGTTCATG GCACACAAGG CAAAGGAGGC AATCTTCGCA     660

GACCGGACTC ATATCAAAAG GATGAAACGA CTTTTCCATA CGACAACCAA ATAGCCGTCT     720

ACGGTAGACG AATGCAAACC CAATATGAGG CCATCAATCA ATCCGAATGA CAGCTTTTGG     780

GCAATATATT ATGCATATTT TGATTCGCGT TTAAAGGAAA AGTGCATATA TTTGCGATTG     840

TGGTATTTCT TTCGGTTTCT ATGTGAATTT TGTCTCCCAA GAAGACTTTA TAATGCATAA     900

ATACAGAAGG GGTACTACAC AGTAAAATCA TATTCTAATT TCATCAAA ATG AAA AAC     957
                                                  Met Lys Asn
                                                    1

TTG AAC AAG TTT GTT TCG ATT GCT CTT TGC TCT TCC TTA TTA GGA GGA     1005
Leu Asn Lys Phe Val Ser Ile Ala Leu Cys Ser Ser Leu Leu Gly Gly
        5                  10                  15

ATG GCA TTT GCG CAG CAG ACA GAG TTG GGA CGC AAT CCG AAT GTC AGA     1053
Met Ala Phe Ala Gln Gln Thr Glu Leu Gly Arg Asn Pro Asn Val Arg
```

```
                20                      25                      30                      35
TTG CTC GAA TCC ACT CAG CAA TCG GTG ACA AAG GTT CAG TTC CGT ATG     1101
Leu Leu Glu Ser Thr Gln Gln Ser Val Thr Lys Val Gln Phe Arg Met
                        40                      45                      50

GAC AAC CTC AAG TTC ACC GAA GTT CAA ACC CCT AAG GGA ATC GGA CAA     1149
Asp Asn Leu Lys Phe Thr Glu Val Gln Thr Pro Lys Gly Ile Gly Gln
                55                      60                      65

GTG CCG ACC TAT ACA GAA GGG GTT AAT CTT TCC GAA AAA GGG ATG CCT     1197
Val Pro Thr Tyr Thr Glu Gly Val Asn Leu Ser Glu Lys Gly Met Pro
        70                      75                      80

ACG CTT CCC ATT CTA TCA CGC TCT TTG GCG GTT TCA GAC ACT CGT GAG     1245
Thr Leu Pro Ile Leu Ser Arg Ser Leu Ala Val Ser Asp Thr Arg Glu
    85                      90                      95

ATG AAG GTA GAG GTT GTT TCC TCA AAG TTC ATC GAA AAG AAA AAT GTC     1293
Met Lys Val Glu Val Val Ser Ser Lys Phe Ile Glu Lys Lys Asn Val
100                     105                     110                     115

CTG ATT GCA CCC TCC AAG GGC ATG ATT ATG CGT AAC GAA GAT CCG AAA     1341
Leu Ile Ala Pro Ser Lys Gly Met Ile Met Arg Asn Glu Asp Pro Lys
                        120                     125                     130

AAG ATC CCT TAC GTT TAT GGA AAG AGC TAC TCG CAA AAC AAA TTC TTC     1389
Lys Ile Pro Tyr Val Tyr Gly Lys Ser Tyr Ser Gln Asn Lys Phe Phe
                135                     140                     145

CCG GGA GAG ATC GCC ACG CTT GAT GAT CCT TTT ATC CTT CGT GAT GTG     1437
Pro Gly Glu Ile Ala Thr Leu Asp Asp Pro Phe Ile Leu Arg Asp Val
        150                     155                     160

CGT GGA CAG GTT GTA AAC TTT GCG CCT TTG CAG TAT AAC CCT GTG ACA     1485
Arg Gly Gln Val Val Asn Phe Ala Pro Leu Gln Tyr Asn Pro Val Thr
    165                     170                     175

AAG ACG TTG CGC ATC TAT ACG GAA ATC ACT GTG GCA GTG AGC GAA ACT     1533
Lys Thr Leu Arg Ile Tyr Thr Glu Ile Thr Val Ala Val Ser Glu Thr
180                     185                     190                     195

TCG GAA CAA GGC AAA AAT ATT CTG AAC AAG AAA GGT ACA TTT GCC GGC     1581
Ser Glu Gln Gly Lys Asn Ile Leu Asn Lys Lys Gly Thr Phe Ala Gly
                        200                     205                     210

TTT GAA GAC ACA TAC AAG CGC ATG TTC ATG AAC TAC GAG CCG GGG CGT     1629
Phe Glu Asp Thr Tyr Lys Arg Met Phe Met Asn Tyr Glu Pro Gly Arg
                215                     220                     225

TAC ACA CCG GTA GAG GAA AAA CAA AAT GGT CGT ATG ATC GTC ATC GTA     1677
Tyr Thr Pro Val Glu Glu Lys Gln Asn Gly Arg Met Ile Val Ile Val
        230                     235                     240

GCC AAA AAG TAT GAG GGA GAT ATT AAA GAT TTC GTT GAT TGG AAA AAC     1725
Ala Lys Lys Tyr Glu Gly Asp Ile Lys Asp Phe Val Asp Trp Lys Asn
    245                     250                     255

CAA CGC GGT CTC CGT ACC GAG GTG AAA GTG GCA GAA GAT ATT GCT TCT     1773
Gln Arg Gly Leu Arg Thr Glu Val Lys Val Ala Glu Asp Ile Ala Ser
260                     265                     270                     275

CCC GTT ACA GCT AAT GCT ATT CAG CAG TTC GTT AAG CAA GAA TAC GAG     1821
Pro Val Thr Ala Asn Ala Ile Gln Gln Phe Val Lys Gln Glu Tyr Glu
                        280                     285                     290

AAA GAA GGT AAT GAT TTG ACC TAT GTT CTT TTG GTT GGC GAT CAC AAA     1869
Lys Glu Gly Asn Asp Leu Thr Tyr Val Leu Leu Val Gly Asp His Lys
                295                     300                     305

GAT ATT CCT GCC AAA ATT ACT CCG GGG ATC AAA TCC GAC CAG GTA TAT     1917
Asp Ile Pro Ala Lys Ile Thr Pro Gly Ile Lys Ser Asp Gln Val Tyr
        310                     315                     320

GGA CAA ATA GTA GGT AAT GAC CAC TAC AAC GAA GTC TTC ATC GGT CGT     1965
Gly Gln Ile Val Gly Asn Asp His Tyr Asn Glu Val Phe Ile Gly Arg
    325                     330                     335

TTC TCA TGT GAG AGC AAA GAG GAT CTG AAG ACA CAA ATC GAT CGG ACT     2013
```

-continued

```
Phe Ser Cys Glu Ser Lys Glu Asp Leu Lys Thr Gln Ile Asp Arg Thr
340                 345                 350                 355

ATT CAC TAT GAG CGC AAT ATA ACC ACG GAA GAC AAA TGG CTC GGT CAG    2061
Ile His Tyr Glu Arg Asn Ile Thr Thr Glu Asp Lys Trp Leu Gly Gln
                        360                 365                 370

GCT CTT TGT ATT GCT TCG GCT GAA GGA GGC CCA TCC GCA GAC AAT GGT    2109
Ala Leu Cys Ile Ala Ser Ala Glu Gly Gly Pro Ser Ala Asp Asn Gly
                375                 380                 385

GAA AGT GAT ATC CAG CAT GAG AAT GTA ATC GCC AAT CTG CTT ACC CAG    2157
Glu Ser Asp Ile Gln His Glu Asn Val Ile Ala Asn Leu Leu Thr Gln
        390                 395                 400

TAT GGC TAT ACC AAG ATT ATC AAA TGT TAT GAT CCG GGA GTA ACT CCT    2205
Tyr Gly Tyr Thr Lys Ile Ile Lys Cys Tyr Asp Pro Gly Val Thr Pro
405                 410                 415

AAA AAC ATT ATT GAT GCT TTC AAC GGA GGA ATC TCG TTG GTC AAC TAT    2253
Lys Asn Ile Ile Asp Ala Phe Asn Gly Gly Ile Ser Leu Val Asn Tyr
420                 425                 430                 435

ACG GGC CAC GGT AGC GAA ACA GCT TGG GGT ACG TCT CAC TTC GGC ACC    2301
Thr Gly His Gly Ser Glu Thr Ala Trp Gly Thr Ser His Phe Gly Thr
                440                 445                 450

ACT CAT GTG AAG CAG CTT ACC AAC AGC AAC CAG CTA CCG TTT ATT TTC    2349
Thr His Val Lys Gln Leu Thr Asn Ser Asn Gln Leu Pro Phe Ile Phe
                455                 460                 465

GAC GTA GCT TGT GTG AAT GGC GAT TTC CTA TTC AGC ATG CCT TGC TTC    2397
Asp Val Ala Cys Val Asn Gly Asp Phe Leu Phe Ser Met Pro Cys Phe
            470                 475                 480

GCA GAA GCC CTG ATG CGT GCA CAA AAA GAT GGT AAG CCG ACA GGT ACT    2445
Ala Glu Ala Leu Met Arg Ala Gln Lys Asp Gly Lys Pro Thr Gly Thr
            485                 490                 495

GTT GCT ATC ATA GCG TCT ACG ATC AAC CAG TCT TGG GCT TCT CCT ATG    2493
Val Ala Ile Ile Ala Ser Thr Ile Asn Gln Ser Trp Ala Ser Pro Met
500                 505                 510                 515

CGC GGG CAG GAT GAG ATG AAC GAA ATT CTG TGC GAA AAA CAC CCG AAC    2541
Arg Gly Gln Asp Glu Met Asn Glu Ile Leu Cys Glu Lys His Pro Asn
                520                 525                 530

AAC ATC AAG CGT ACT TTC GGT GGT GTC ACC ATG AAC GGT ATG TTT GCT    2589
Asn Ile Lys Arg Thr Phe Gly Gly Val Thr Met Asn Gly Met Phe Ala
                535                 540                 545

ATG GTG GAA AAG TAT AAA AAG GAT GGT GAG AAG ATG CTC GAC ACA TGG    2637
Met Val Glu Lys Tyr Lys Lys Asp Gly Glu Lys Met Leu Asp Thr Trp
            550                 555                 560

ACT GTT TTC GGC GAC CCC TCG CTG CTC GTT CGT ACA CTT GTC CCG ACC    2685
Thr Val Phe Gly Asp Pro Ser Leu Leu Val Arg Thr Leu Val Pro Thr
            565                 570                 575

AAA ATG CAG GTT ACG GCT CCG GCT CAG ATT AAT TTG ACG GAT GCT TCA    2733
Lys Met Gln Val Thr Ala Pro Ala Gln Ile Asn Leu Thr Asp Ala Ser
580                 585                 590                 595

GTC AAC GTA TCT TGC GAT TAT AAT GGT GCT ATT GCT ACC ATT TCA GCC    2781
Val Asn Val Ser Cys Asp Tyr Asn Gly Ala Ile Ala Thr Ile Ser Ala
                600                 605                 610

AAT GGA AAG ATG TTC GGT TCT GCA GTT GTC GAA AAT GGA ACA GCT ACA    2829
Asn Gly Lys Met Phe Gly Ser Ala Val Val Glu Asn Gly Thr Ala Thr
                615                 620                 625

ATC AAT CTG ACA GGT CTG ACA AAT GAA AGC ACG CTT ACC CTT ACA GTA    2877
Ile Asn Leu Thr Gly Leu Thr Asn Glu Ser Thr Leu Thr Leu Thr Val
            630                 635                 640

GTT GGT TAC AAC AAA GAG ACG GTT ATT AAG ACC ATC AAC ACT AAT GGT    2925
Val Gly Tyr Asn Lys Glu Thr Val Ile Lys Thr Ile Asn Thr Asn Gly
645                 650                 655
```

```
GAG CCT AAC CCC TAC CAG CCC GTT TCC AAC TTG ACA GCT ACA ACG CAG    2973
Glu Pro Asn Pro Tyr Gln Pro Val Ser Asn Leu Thr Ala Thr Thr Gln
660                 665                 670                 675

GGT CAG AAA GTA ACG CTC AAG TGG GAT GCA CCG AGC ACG AAA ACC AAT    3021
Gly Gln Lys Val Thr Leu Lys Trp Asp Ala Pro Ser Thr Lys Thr Asn
            680                 685                 690

GCA ACC ACT AAT ACC GCT CGC AGC GTG GAT GGC ATA CGA GAA TTG GTT    3069
Ala Thr Thr Asn Thr Ala Arg Ser Val Asp Gly Ile Arg Glu Leu Val
                695                 700                 705

CTT CTG TCA GTC AGC GAT GCC CCC GAA CTT CTT CGC AGC GGT CAG GCC    3117
Leu Leu Ser Val Ser Asp Ala Pro Glu Leu Leu Arg Ser Gly Gln Ala
        710                 715                 720

GAG ATT GTT CTT GAA GCT CAC GAT GTT TGG AAT GAT GGA TCC GGT TAT    3165
Glu Ile Val Leu Glu Ala His Asp Val Trp Asn Asp Gly Ser Gly Tyr
725                 730                 735

CAG ATT CTT TTG GAT GCA GAC CAT GAT CAA TAT GGA CAG GTT ATA CCC    3213
Gln Ile Leu Leu Asp Ala Asp His Asp Gln Tyr Gly Gln Val Ile Pro
740                 745                 750                 755

AGT GAT ACC CAT ACT CTT TGG CCG AAC TGT AGT GTC CCG GCC AAT CTG    3261
Ser Asp Thr His Thr Leu Trp Pro Asn Cys Ser Val Pro Ala Asn Leu
            760                 765                 770

TTC GCT CCG TTC GAA TAT ACT GTT CCG GAA AAT GCA GAT CCT TCT TGT    3309
Phe Ala Pro Phe Glu Tyr Thr Val Pro Glu Asn Ala Asp Pro Ser Cys
                775                 780                 785

TCC CCT ACC AAT ATG ATA ATG GAT GGT ACT GCA TCC GTT AAT ATA CCG    3357
Ser Pro Thr Asn Met Ile Met Asp Gly Thr Ala Ser Val Asn Ile Pro
        790                 795                 800

GCC GGA ACT TAT GAC TTT GCA ATT GCT GCT CCT CAA GCA AAT GCA AAG    3405
Ala Gly Thr Tyr Asp Phe Ala Ile Ala Ala Pro Gln Ala Asn Ala Lys
805                 810                 815

ATT TGG ATT GCC GGA CAA GGA CCG ACG AAA GAA GAT GAT TAT GTA TTT    3453
Ile Trp Ile Ala Gly Gln Gly Pro Thr Lys Glu Asp Asp Tyr Val Phe
820                 825                 830                 835

GAA GCC GGT AAA AAA TAC CAT TTC CTT ATG AAG AAG ATG GGT AGC GGT    3501
Glu Ala Gly Lys Lys Tyr His Phe Leu Met Lys Lys Met Gly Ser Gly
            840                 845                 850

GAT GGA ACT GAA TTG ACT ATA AGC GAA GGT GGT GGA AGC GAT TAC ACC    3549
Asp Gly Thr Glu Leu Thr Ile Ser Glu Gly Gly Gly Ser Asp Tyr Thr
                855                 860                 865

TAT ACT GTC TAT CGT GAC GGC ACG AAG ATC AAG GAA GGT CTG ACG GCT    3597
Tyr Thr Val Tyr Arg Asp Gly Thr Lys Ile Lys Glu Gly Leu Thr Ala
        870                 875                 880

ACG ACA TTC GAA GAA GAC GGT GTA GCT ACG GGC AAT CAT GAG TAT TGC    3645
Thr Thr Phe Glu Glu Asp Gly Val Ala Thr Gly Asn His Glu Tyr Cys
885                 890                 895

GTG GAA GTT AAG TAC ACA GCC GGC GTA TCT CCG AAG GTA TGT AAA GAC    3693
Val Glu Val Lys Tyr Thr Ala Gly Val Ser Pro Lys Val Cys Lys Asp
900                 905                 910                 915

GTT ACG GTA GAA GGA TCC AAT GAA TTT GCT CCT GTA CAG AAC CTG ACC    3741
Val Thr Val Glu Gly Ser Asn Glu Phe Ala Pro Val Gln Asn Leu Thr
            920                 925                 930

GGT AGT GCA GTC GGC CAG AAA GTA ACG CTC AAG TGG GAT GCA CCT AAT    3789
Gly Ser Ala Val Gly Gln Lys Val Thr Leu Lys Trp Asp Ala Pro Asn
                935                 940                 945

GGT ACC CCG AAT CCA AAT CCG AAT CCG AAT CCG AAT CCC GGA ACA ACA    3837
Gly Thr Pro Asn Pro Asn Pro Asn Pro Asn Pro Asn Pro Gly Thr Thr
        950                 955                 960

ACA CTT TCC GAA TCA TTC GAA AAT GGT ATT CCT GCC TCA TGG AAG ACG    3885
Thr Leu Ser Glu Ser Phe Glu Asn Gly Ile Pro Ala Ser Trp Lys Thr
965                 970                 975
```

```
ATC GAT GCA GAC GGT GAC GGG CAT GGC TGG AAG CCT GGA AAT GCT CCC      3933
Ile Asp Ala Asp Gly Asp Gly His Gly Trp Lys Pro Gly Asn Ala Pro
980             985                 990                 995

GGA ATC GCT GGC TAC AAT AGC AAT GGT TGT GTA TAT TCA GAG TCA TTC      3981
Gly Ile Ala Gly Tyr Asn Ser Asn Gly Cys Val Tyr Ser Glu Ser Phe
                1000                1005                1010

GGT CTT GGT GGT ATA GGA GTT CTT ACC CCT GAC AAC TAT CTG ATA ACA      4029
Gly Leu Gly Gly Ile Gly Val Leu Thr Pro Asp Asn Tyr Leu Ile Thr
            1015                1020                1025

CCG GCA TTG GAT TTG CCT AAC GGA GGT AAG TTG ACT TTC TGG GTA TGC      4077
Pro Ala Leu Asp Leu Pro Asn Gly Gly Lys Leu Thr Phe Trp Val Cys
        1030                1035                1040

GCA CAG GAT GCT AAT TAT GCA TCC GAG CAC TAT GCG GTG TAT GCA TCT      4125
Ala Gln Asp Ala Asn Tyr Ala Ser Glu His Tyr Ala Val Tyr Ala Ser
    1045                1050                1055

TCG ACC GGT AAC GAT GCA TCC AAC TTC ACG AAT GCT TTG TTG GAA GAG      4173
Ser Thr Gly Asn Asp Ala Ser Asn Phe Thr Asn Ala Leu Leu Glu Glu
1060                1065                1070                1075

ACG ATT ACG GCA AAA GGT GTT CGC TCG CCG GAA GCT ATT CGT GGT CGT      4221
Thr Ile Thr Ala Lys Gly Val Arg Ser Pro Glu Ala Ile Arg Gly Arg
                1080                1085                1090

ATA CAG GGT ACT TGG CGC CAG AAG ACG GTA GAC CTT CCC GCA GGT ACG      4269
Ile Gln Gly Thr Trp Arg Gln Lys Thr Val Asp Leu Pro Ala Gly Thr
                1095                1100                1105

AAA TAT GTT GCT TTC CGT CAC TTC CAA AGC ACG GAT ATG TTC TAC ATC      4317
Lys Tyr Val Ala Phe Arg His Phe Gln Ser Thr Asp Met Phe Tyr Ile
            1110                1115                1120

GAC CTT GAT GAG GTT GAG ATC AAG GCC AAC GGC AAG CGC GCA GAC TTC      4365
Asp Leu Asp Glu Val Glu Ile Lys Ala Asn Gly Lys Arg Ala Asp Phe
        1125                1130                1135

ACG GAA ACG TTC GAG TCT TCT ACT CAT GGA GAG GCA CCG GCG GAA TGG      4413
Thr Glu Thr Phe Glu Ser Ser Thr His Gly Glu Ala Pro Ala Glu Trp
1140                1145                1150                1155

ACT ACT ATC GAT GCC GAT GGC GAT GGT CAG GGT TGG CTC TGT CTG TCT      4461
Thr Thr Ile Asp Ala Asp Gly Asp Gly Gln Gly Trp Leu Cys Leu Ser
                1160                1165                1170

TCC GGA CAA TTG GAC TGG CTG ACA GCT CAT GGC GGC ACC AAC GTA GTA      4509
Ser Gly Gln Leu Asp Trp Leu Thr Ala His Gly Gly Thr Asn Val Val
            1175                1180                1185

GCC TCT TTC TCA TGG AAT GGA ATG GCT TTG AAT CCT GAT AAC TAT CTC      4557
Ala Ser Phe Ser Trp Asn Gly Met Ala Leu Asn Pro Asp Asn Tyr Leu
        1190                1195                1200

ATC TCA AAG GAT GTT ACA GGC GCA ACG AAG GTA AAG TAC TAC TAT GCA      4605
Ile Ser Lys Asp Val Thr Gly Ala Thr Lys Val Lys Tyr Tyr Tyr Ala
1205                1210                1215

GTC AAC GAC GGT TTT CCC GGG GAT CAC TAT GCG GTG ATG ATC TCC AAG      4653
Val Asn Asp Gly Phe Pro Gly Asp His Tyr Ala Val Met Ile Ser Lys
1220                1225                1230                1235

ACG GGC ACG AAC GCC GGA GAC TTC ACG GTT GTT TTC GAA GAA ACG CCT      4701
Thr Gly Thr Asn Ala Gly Asp Phe Thr Val Val Phe Glu Glu Thr Pro
                1240                1245                1250

AAC GGA ATA AAT AAG GGC GGA GCA AGA TTC GGT CTT TCC ACG GAA GCC      4749
Asn Gly Ile Asn Lys Gly Gly Ala Arg Phe Gly Leu Ser Thr Glu Ala
            1255                1260                1265

AAT GGC GCC AAA CCT CAA AGT GTA TGG ATC GAG CGT ACG GTA GAT TTG      4797
Asn Gly Ala Lys Pro Gln Ser Val Trp Ile Glu Arg Thr Val Asp Leu
        1270                1275                1280

CCT GCG GGC ACG AAG TAT GTT GCT TTC CGT CAC TAC AAT TGC TCG GAT      4845
Pro Ala Gly Thr Lys Tyr Val Ala Phe Arg His Tyr Asn Cys Ser Asp
```

```
            1285                 1290                 1295
    TTG AAC TAC ATT CTT TTG GAT GAT ATT CAG TTC ACC ATG GGT GGC AGC       4893
    Leu Asn Tyr Ile Leu Leu Asp Asp Ile Gln Phe Thr Met Gly Gly Ser
    1300                1305                1310                1315

CCC ACC CCG ACC GAT TAT ACC TAC ACG GTG TAT CGT GAC GGT ACG AAG       4941
    Pro Thr Pro Thr Asp Tyr Thr Tyr Thr Val Tyr Arg Asp Gly Thr Lys
                    1320                1325                1330

ATC AAG GAA GGT CTG ACC GAA ACG ACC TTC GAA GAA GAC GGC GTA GCT       4989
    Ile Lys Glu Gly Leu Thr Glu Thr Thr Phe Glu Glu Asp Gly Val Ala
                1335                1340                1345

ACA GGC AAT CAT GAG TAT TGC GTG GAA GTG AAG TAC ACA GCC GGC GTA       5037
    Thr Gly Asn His Glu Tyr Cys Val Glu Val Lys Tyr Thr Ala Gly Val
                1350                1355                1360

TCT CCG AAA GAG TGC GTA AAC GTA ACT ATT AAT CCG ACT CAG TTC AAT       5085
    Ser Pro Lys Glu Cys Val Asn Val Thr Ile Asn Pro Thr Gln Phe Asn
            1365                1370                1375

CCT GTA AAG AAC CTG AAG GCA CAA CCG GAT GGC GGC GAC GTG GTT CTC       5133
    Pro Val Lys Asn Leu Lys Ala Gln Pro Asp Gly Gly Asp Val Val Leu
    1380                1385                1390                1395

AAG TGG GAA GCC CCG AGC GCA AAA AAG ACA GAA GGT TCT CGT GAA GTA       5181
    Lys Trp Glu Ala Pro Ser Ala Lys Lys Thr Glu Gly Ser Arg Glu Val
                    1400                1405                1410

AAA CGG ATC GGA GAC GGT CTT TTC GTT ACG ATC GAA CCT GCA AAC GAT       5229
    Lys Arg Ile Gly Asp Gly Leu Phe Val Thr Ile Glu Pro Ala Asn Asp
                1415                1420                1425

GTA CGT GCC AAC GAA GCC AAG GTT GTG CTC GCA GCA GAC AAC GTA TGG       5277
    Val Arg Ala Asn Glu Ala Lys Val Val Leu Ala Ala Asp Asn Val Trp
            1430                1435                1440

GGA GAC AAT ACG GGT TAC CAG TTC TTG TTG GAT GCC GAT CAC AAT ACA       5325
    Gly Asp Asn Thr Gly Tyr Gln Phe Leu Leu Asp Ala Asp His Asn Thr
    1445                1450                1455

TTC GGA AGT GTC ATT CCG GCA ACC GGT CCT CTC TTT ACC GGA ACA GCT       5373
    Phe Gly Ser Val Ile Pro Ala Thr Gly Pro Leu Phe Thr Gly Thr Ala
    1460                1465                1470                1475

TCT TCC AAT CTT TAC AGT GCG AAC TTC GAG TAT TTG ATC CCG GCC AAT       5421
    Ser Ser Asn Leu Tyr Ser Ala Asn Phe Glu Tyr Leu Ile Pro Ala Asn
                    1480                1485                1490

GCC GAT CCT GTT GTT ACT ACA CAG AAT ATT ATC GTT ACA GGA CAG GGT       5469
    Ala Asp Pro Val Val Thr Thr Gln Asn Ile Ile Val Thr Gly Gln Gly
                1495                1500                1505

GAA GTT GTA ATC CCC GGT GGT GTT TAC GAC TAT TGC ATT ACG AAC CCG       5517
    Glu Val Val Ile Pro Gly Gly Val Tyr Asp Tyr Cys Ile Thr Asn Pro
            1510                1515                1520

GAA CCT GCA TCC GGA AAG ATG TGG ATC GCA GGA GAT GGA GGC AAC CAG       5565
    Glu Pro Ala Ser Gly Lys Met Trp Ile Ala Gly Asp Gly Gly Asn Gln
    1525                1530                1535

CCT GCA CGT TAT GAC GAT TTC ACA TTC GAA GCA GGC AAG AAG TAC ACC       5613
    Pro Ala Arg Tyr Asp Asp Phe Thr Phe Glu Ala Gly Lys Lys Tyr Thr
    1540                1545                1550                1555

TTC ACG ATG CGT CGC GCC GGA ATG GGA GAT GGA ACT GAT ATG GAA GTC       5661
    Phe Thr Met Arg Arg Ala Gly Met Gly Asp Gly Thr Asp Met Glu Val
                    1560                1565                1570

GAA GAC GAT TCA CCT GCA AGC TAT ACC TAT ACA GTC TAT CGT GAC GGC       5709
    Glu Asp Asp Ser Pro Ala Ser Tyr Thr Tyr Thr Val Tyr Arg Asp Gly
                1575                1580                1585

ACG AAG ATC AAG GAA GGT CTG ACC GAA ACG ACC TAC CGC GAT GCA GGA       5757
    Thr Lys Ile Lys Glu Gly Leu Thr Glu Thr Thr Tyr Arg Asp Ala Gly
            1590                1595                1600

ATG AGT GCA CAA TCT CAT GAG TAT TGC GTA GAG GTT AAG TAC GCA GCC       5805
```

```
Met Ser Ala Gln Ser His Glu Tyr Cys Val Glu Val Lys Tyr Ala Ala
        1605                1610                1615

GGC GTA TCT CCG AAG GTT TGT GTG GAT TAT ATT CCT GAC GGA GTG GCA        5853
Gly Val Ser Pro Lys Val Cys Val Asp Tyr Ile Pro Asp Gly Val Ala
1620            1625                1630                    1635

GAC GTA ACG GCT CAG AAG CCT TAC ACG CTG ACA GTT GTT GGA AAG ACG        5901
Asp Val Thr Ala Gln Lys Pro Tyr Thr Leu Thr Val Val Gly Lys Thr
                1640                1645                1650

ATC ACG GTA ACT TGC CAA GGC GAA GCT ATG ATC TAC GAC ATG AAC GGT        5949
Ile Thr Val Thr Cys Gln Gly Glu Ala Met Ile Tyr Asp Met Asn Gly
            1655                1660                1665

CGT CGT CTG GCA GCC GGT CGC AAC ACA GTT GTT TAC ACG GCT CAG GGC        5997
Arg Arg Leu Ala Ala Gly Arg Asn Thr Val Val Tyr Thr Ala Gln Gly
        1670                1675                1680

GGC TAC TAT GCA GTC ATG GTT GTC GTT GAC GGC AAG TCT TAC GTA GAG        6045
Gly Tyr Tyr Ala Val Met Val Val Val Asp Gly Lys Ser Tyr Val Glu
    1685                1690                1695

AAA CTC GCT GTA AAG TAA TTCTGTCTTG GACTCGGAGA CTTTGTGCAG               6093
Lys Leu Ala Val Lys *
1700            1705

ACACTTTTAA TATAGGTCTG TAATTGTCTC AGAGTATGAA TCGATCGCCC GACCTCCTTT      6153

TAAGGAAGTC TGGGCGACTT CGTTTTTATG CCTATTATTC TAATATACTT CTGAAACAAT      6213

TTGTTCCAAA AAGTTGCATG AAAAGATTAT CTTACTATCT TTGCACTGCA AAAGGGGAGT      6273

TTCCTAAGGT TTTCCCCGGA GTAGTACGGT AATAACGGTG TGGTAGTTCA GCTGGTTAGA      6333

ATACCTGCCT GTCACGCAGG GGGTCGCGGG TTCGAGTCCC GTCCATACCG CTAAATAGCT      6393

GAAAGATAGG CTATAGGTCA TCTGAAGCAA TTTTAGAAAC GAATCCAAAA GCGTCTTAAT      6453

TCCAACGAAT TAAGGCGCTT TTTCTTTGTC GCCACCCCAC ACGTCGGATG AGGTTCGGAA      6513

TAGGCGTATA TTCCGTAAAT ATGCCTCCGG TGGTTCCATT TTGGTTACAA AAAACAAAGG      6573

GGCTGAAAAT TGTAACCACA GACGACGTTA AGACGATGTT TAGACGATTG ACAAATTACT      6633

CTGTTTCAAA ATCATATGTC GAACTTTGTA GCCGTATGGT TACACTAATT TTGGAGCAAA      6693

ATGAAGAGTC AATTTCGTTC AGTTTTTTAC TTGCGCAGCA ATTACATCAA CAAAGAAGGT      6753

AAAACTCCTG TCCTTATTCG TATTTATCTG AATAAGGAAC GCCTGTCGTT GGGTTCGACA      6813

GGGCTGGCTG TTAATCCCAT ACAATGGGAT TCAGAAAAAG AGAAAGTCAA AGGACATAGT      6873

GCAGAAGCAC TTGAAGTCAA TCGAAAGATC GAAGAAATCA GGGCTGATAT TCTGACCATT      6933

TACAAACGTT TGGAAGTAAC AGTAGATGAT TTGACGCCGG AGAGGATCAA ATCGGAATAC      6993

TGCGGACAGA CGGATACATT AAACAGTATA GTGGAACTTT TCGATAAACA TAACGAGGAT      7053

GTCCGGGCCC AGGTGGGAAT CAATAAAACG GCTGCCACTT TACAAAAATA CGAAAACAGC      7113

AAACGGCATT TTACCCGATT CCTCAAAGCG AAGTACAACA GAACGGATCT CAAATTCTCA      7173

GAGCTTACCC CGTTGGTCAT TCATAACTTT GAGATATATC TGCTGACTGT AGCCCATTGT      7233

TGCCCGAATA CGGCAACCAA AATCTTGAAG CTT                                   7266
```

(2) INFORMATION FOR SEQ ID NO:6:

(i) SEQUENCE CHARACTERISTICS:
        (A) LENGTH: 1704 amino acids
        (B) TYPE: amino acid
        (D) TOPOLOGY: linear (ii) MOLECULE TYPE: protein (xi) SEQUENCE DESCRIPTION: SEQ ID NO:6:

-continued

```
Met Lys Asn Leu Asn Lys Phe Val Ser Ile Ala Leu Cys Ser Ser Leu
 1               5                  10                 15

Leu Gly Gly Met Ala Phe Ala Gln Gln Thr Glu Leu Gly Arg Asn Pro
            20                  25                 30

Asn Val Arg Leu Leu Glu Ser Thr Gln Gln Ser Val Thr Lys Val Gln
        35                  40                  45

Phe Arg Met Asp Asn Leu Lys Phe Thr Glu Val Gln Thr Pro Lys Gly
    50                  55                  60

Ile Gly Gln Val Pro Thr Tyr Thr Glu Gly Val Asn Leu Ser Glu Lys
 65                 70                  75                  80

Gly Met Pro Thr Leu Pro Ile Leu Ser Arg Ser Leu Ala Val Ser Asp
                85                  90                  95

Thr Arg Glu Met Lys Val Glu Val Val Ser Ser Lys Phe Ile Glu Lys
                100                 105                 110

Lys Asn Val Leu Ile Ala Pro Ser Lys Gly Met Ile Met Arg Asn Glu
            115                 120                 125

Asp Pro Lys Lys Ile Pro Tyr Val Tyr Gly Lys Ser Tyr Ser Gln Asn
130                 135                 140

Lys Phe Phe Pro Gly Glu Ile Ala Thr Leu Asp Asp Pro Phe Ile Leu
145                 150                 155                 160

Arg Asp Val Arg Gly Gln Val Val Asn Phe Ala Pro Leu Gln Tyr Asn
                165                 170                 175

Pro Val Thr Lys Thr Leu Arg Ile Tyr Thr Glu Ile Thr Val Ala Val
                180                 185                 190

Ser Glu Thr Ser Glu Gln Gly Lys Asn Ile Leu Asn Lys Lys Gly Thr
            195                 200                 205

Phe Ala Gly Phe Glu Asp Thr Tyr Lys Arg Met Phe Met Asn Tyr Glu
            210                 215                 220

Pro Gly Arg Tyr Thr Pro Val Glu Glu Lys Gln Asn Gly Arg Met Ile
225                 230                 235                 240

Val Ile Val Ala Lys Lys Tyr Glu Gly Asp Ile Lys Asp Phe Val Asp
                245                 250                 255

Trp Lys Asn Gln Arg Gly Leu Arg Thr Glu Val Lys Val Ala Glu Asp
            260                 265                 270

Ile Ala Ser Pro Val Thr Ala Asn Ala Ile Gln Gln Phe Val Lys Gln
        275                 280                 285

Glu Tyr Glu Lys Glu Gly Asn Asp Leu Thr Tyr Val Leu Leu Val Gly
290                 295                 300

Asp His Lys Asp Ile Pro Ala Lys Ile Thr Pro Gly Ile Lys Ser Asp
305                 310                 315                 320

Gln Val Tyr Gly Gln Ile Val Gly Asn Asp His Tyr Asn Glu Val Phe
                325                 330                 335

Ile Gly Arg Phe Ser Cys Glu Ser Lys Glu Asp Leu Lys Thr Gln Ile
            340                 345                 350

Asp Arg Thr Ile His Tyr Glu Arg Asn Ile Thr Thr Glu Asp Lys Trp
        355                 360                 365

Leu Gly Gln Ala Leu Cys Ile Ala Ser Ala Glu Gly Pro Ser Ala
370                 375                 380

Asp Asn Gly Glu Ser Asp Ile Gln His Glu Asn Val Ile Ala Asn Leu
385                 390                 395                 400

Leu Thr Gln Tyr Gly Tyr Thr Lys Ile Ile Lys Cys Tyr Asp Pro Gly
            405                 410                 415

Val Thr Pro Lys Asn Ile Ile Asp Ala Phe Asn Gly Gly Ile Ser Leu
```

-continued

```
                420                 425                 430
Val Asn Tyr Thr Gly His Gly Ser Glu Thr Ala Trp Gly Thr Ser His
            435                 440                 445

Phe Gly Thr Thr His Val Lys Gln Leu Thr Asn Ser Asn Gln Leu Pro
450                 455                 460

Phe Ile Phe Asp Val Ala Cys Val Asn Gly Asp Phe Leu Phe Ser Met
465                 470                 475                 480

Pro Cys Phe Ala Glu Ala Leu Met Arg Ala Gln Lys Asp Gly Lys Pro
                485                 490                 495

Thr Gly Thr Val Ala Ile Ile Ala Ser Thr Ile Asn Gln Ser Trp Ala
                500                 505                 510

Ser Pro Met Arg Gly Gln Asp Glu Met Asn Glu Ile Leu Cys Glu Lys
                515                 520                 525

His Pro Asn Asn Ile Lys Arg Thr Phe Gly Gly Val Thr Met Asn Gly
                530                 535                 540

Met Phe Ala Met Val Glu Lys Tyr Lys Lys Asp Gly Glu Lys Met Leu
545                 550                 555                 560

Asp Thr Trp Thr Val Phe Gly Asp Pro Ser Leu Leu Val Arg Thr Leu
                565                 570                 575

Val Pro Thr Lys Met Gln Val Thr Ala Pro Ala Gln Ile Asn Leu Thr
                580                 585                 590

Asp Ala Ser Val Asn Val Ser Cys Asp Tyr Asn Gly Ala Ile Ala Thr
                595                 600                 605

Ile Ser Ala Asn Gly Lys Met Phe Gly Ser Ala Val Val Glu Asn Gly
                610                 615                 620

Thr Ala Thr Ile Asn Leu Thr Gly Leu Thr Asn Glu Ser Thr Leu Thr
625                 630                 635                 640

Leu Thr Val Val Gly Tyr Asn Lys Glu Thr Val Ile Lys Thr Ile Asn
                645                 650                 655

Thr Asn Gly Glu Pro Asn Pro Tyr Gln Pro Val Ser Asn Leu Thr Ala
                660                 665                 670

Thr Thr Gln Gly Gln Lys Val Thr Leu Lys Trp Asp Ala Pro Ser Thr
                675                 680                 685

Lys Thr Asn Ala Thr Thr Asn Thr Ala Arg Ser Val Asp Gly Ile Arg
690                 695                 700

Glu Leu Val Leu Leu Ser Val Ser Asp Ala Pro Glu Leu Leu Arg Ser
705                 710                 715                 720

Gly Gln Ala Glu Ile Val Leu Glu Ala His Asp Val Trp Asn Asp Gly
                725                 730                 735

Ser Gly Tyr Gln Ile Leu Leu Asp Ala Asp His Asp Gln Tyr Gly Gln
                740                 745                 750

Val Ile Pro Ser Asp Thr His Thr Leu Trp Pro Asn Cys Ser Val Pro
                755                 760                 765

Ala Asn Leu Phe Ala Pro Phe Glu Tyr Thr Val Pro Glu Asn Ala Asp
                770                 775                 780

Pro Ser Cys Ser Pro Thr Asn Met Ile Met Asp Gly Thr Ala Ser Val
785                 790                 795                 800

Asn Ile Pro Ala Gly Thr Tyr Asp Phe Ala Ile Ala Ala Pro Gln Ala
                805                 810                 815

Asn Ala Lys Ile Trp Ile Ala Gly Gln Gly Pro Thr Lys Glu Asp Asp
                820                 825                 830

Tyr Val Phe Glu Ala Gly Lys Lys Tyr His Phe Leu Met Lys Lys Met
                835                 840                 845
```

-continued

```
Gly Ser Gly Asp Gly Thr Glu Leu Thr Ile Ser Glu Gly Gly Ser
            850                 855                 860
Asp Tyr Thr Tyr Thr Val Tyr Arg Asp Gly Thr Lys Ile Lys Glu Gly
865                 870                 875                 880
Leu Thr Ala Thr Thr Phe Glu Glu Asp Gly Val Ala Thr Gly Asn His
                    885                 890                 895
Glu Tyr Cys Val Glu Val Lys Tyr Thr Ala Gly Val Ser Pro Lys Val
                900                 905                 910
Cys Lys Asp Val Thr Val Glu Gly Ser Asn Glu Phe Ala Pro Val Gln
            915                 920                 925
Asn Leu Thr Gly Ser Ala Val Gly Gln Lys Val Thr Leu Lys Trp Asp
            930                 935                 940
Ala Pro Asn Gly Thr Pro Asn Pro Asn Pro Asn Pro Asn Pro Asn Pro
945                 950                 955                 960
Gly Thr Thr Thr Leu Ser Glu Ser Phe Glu Asn Gly Ile Pro Ala Ser
                    965                 970                 975
Trp Lys Thr Ile Asp Ala Asp Gly Asp Gly His Gly Trp Lys Pro Gly
                980                 985                 990
Asn Ala Pro Gly Ile Ala Gly Tyr Asn Ser Asn Gly Cys Val Tyr Ser
            995                 1000                1005
Glu Ser Phe Gly Leu Gly Gly Ile Gly Val Leu Thr Pro Asp Asn Tyr
        1010                1015                1020
Leu Ile Thr Pro Ala Leu Asp Leu Pro Asn Gly Gly Lys Leu Thr Phe
1025                1030                1035                1040
Trp Val Cys Ala Gln Asp Ala Asn Tyr Ala Ser Glu His Tyr Ala Val
                1045                1050                1055
Tyr Ala Ser Ser Thr Gly Asn Asp Ala Ser Asn Phe Thr Asn Ala Leu
            1060                1065                1070
Leu Glu Glu Thr Ile Thr Ala Lys Gly Val Arg Ser Pro Glu Ala Ile
        1075                1080                1085
Arg Gly Arg Ile Gln Gly Thr Trp Arg Gln Lys Thr Val Asp Leu Pro
    1090                1095                1100
Ala Gly Thr Lys Tyr Val Ala Phe Arg His Phe Gln Ser Thr Asp Met
1105                1110                1115                1120
Phe Tyr Ile Asp Leu Asp Glu Val Glu Ile Lys Ala Asn Gly Lys Arg
                1125                1130                1135
Ala Asp Phe Thr Glu Thr Phe Glu Ser Ser Thr His Gly Glu Ala Pro
            1140                1145                1150
Ala Glu Trp Thr Thr Ile Asp Ala Asp Gly Asp Gly Gln Gly Trp Leu
        1155                1160                1165
Cys Leu Ser Ser Gly Gln Leu Asp Trp Leu Thr Ala His Gly Gly Thr
    1170                1175                1180
Asn Val Val Ala Ser Phe Ser Trp Asn Gly Met Ala Leu Asn Pro Asp
1185                1190                1195                1200
Asn Tyr Leu Ile Ser Lys Asp Val Thr Gly Ala Thr Lys Val Lys Tyr
                1205                1210                1215
Tyr Tyr Ala Val Asn Asp Gly Phe Pro Gly Asp His Tyr Ala Val Met
            1220                1225                1230
Ile Ser Lys Thr Gly Thr Asn Ala Gly Asp Phe Thr Val Val Phe Glu
        1235                1240                1245
Glu Thr Pro Asn Gly Ile Asn Lys Gly Gly Ala Arg Phe Gly Leu Ser
    1250                1255                1260
```

-continued

```
Thr Glu Ala Asn Gly Ala Lys Pro Gln Ser Val Trp Ile Glu Arg Thr
1265                1270                1275                1280

Val Asp Leu Pro Ala Gly Thr Lys Tyr Val Ala Phe Arg His Tyr Asn
            1285                1290                1295

Cys Ser Asp Leu Asn Tyr Ile Leu Leu Asp Asp Ile Gln Phe Thr Met
            1300                1305                1310

Gly Gly Ser Pro Thr Pro Thr Asp Tyr Thr Tyr Thr Val Tyr Arg Asp
        1315                1320                1325

Gly Thr Lys Ile Lys Glu Gly Leu Thr Glu Thr Thr Phe Glu Glu Asp
        1330                1335                1340

Gly Val Ala Thr Gly Asn His Glu Tyr Cys Val Glu Val Lys Tyr Thr
1345                1350                1355                1360

Ala Gly Val Ser Pro Lys Glu Cys Val Asn Val Thr Ile Asn Pro Thr
            1365                1370                1375

Gln Phe Asn Pro Val Lys Asn Leu Lys Ala Gln Pro Asp Gly Gly Asp
            1380                1385                1390

Val Val Leu Lys Trp Glu Ala Pro Ser Ala Lys Lys Thr Glu Gly Ser
        1395                1400                1405

Arg Glu Val Lys Arg Ile Gly Asp Gly Leu Phe Val Thr Ile Glu Pro
        1410                1415                1420

Ala Asn Asp Val Arg Ala Asn Glu Ala Lys Val Val Leu Ala Ala Asp
1425                1430                1435                1440

Asn Val Trp Gly Asp Asn Thr Gly Tyr Gln Phe Leu Leu Asp Ala Asp
            1445                1450                1455

His Asn Thr Phe Gly Ser Val Ile Pro Ala Thr Gly Pro Leu Phe Thr
            1460                1465                1470

Gly Thr Ala Ser Ser Asn Leu Tyr Ser Ala Asn Phe Glu Tyr Leu Ile
        1475                1480                1485

Pro Ala Asn Ala Asp Pro Val Val Thr Thr Gln Asn Ile Ile Val Thr
        1490                1495                1500

Gly Gln Gly Glu Val Val Ile Pro Gly Gly Val Tyr Asp Tyr Cys Ile
1505                1510                1515                1520

Thr Asn Pro Glu Pro Ala Ser Gly Lys Met Trp Ile Ala Gly Asp Gly
            1525                1530                1535

Gly Asn Gln Pro Ala Arg Tyr Asp Asp Phe Thr Phe Glu Ala Gly Lys
            1540                1545                1550

Lys Tyr Thr Phe Thr Met Arg Arg Ala Gly Met Gly Asp Gly Thr Asp
        1555                1560                1565

Met Glu Val Glu Asp Asp Ser Pro Ala Ser Tyr Thr Tyr Thr Val Tyr
        1570                1575                1580

Arg Asp Gly Thr Lys Ile Lys Glu Gly Leu Thr Glu Thr Thr Tyr Arg
1585                1590                1595                1600

Asp Ala Gly Met Ser Ala Gln Ser His Glu Tyr Cys Val Glu Val Lys
            1605                1610                1615

Tyr Ala Ala Gly Val Ser Pro Lys Val Cys Val Asp Tyr Ile Pro Asp
            1620                1625                1630

Gly Val Ala Asp Val Thr Ala Gln Lys Pro Tyr Thr Leu Thr Val Val
        1635                1640                1645

Gly Lys Thr Ile Thr Val Thr Cys Gln Gly Glu Ala Met Ile Tyr Asp
        1650                1655                1660

Met Asn Gly Arg Arg Leu Ala Ala Gly Arg Asn Thr Val Val Tyr Thr
1665                1670                1675                1680

Ala Gln Gly Gly Tyr Tyr Ala Val Met Val Val Val Asp Gly Lys Ser
```

```
                      1685                 1690                 1695
Tyr Val Glu Lys Leu Ala Val Lys
                1700                 1705

(2) INFORMATION FOR SEQ ID NO:7:

(i) SEQUENCE CHARACTERISTICS:
         (A) LENGTH: 3561 base pairs
         (B) TYPE: nucleic acid
         (C) STRANDEDNESS: double
         (D) TOPOLOGY: Not Relevant (ii) MOLECULE TYPE: DNA (genomic)

(iii) HYPOTHETICAL: NO (ix) FEATURE:
         (A) NAME/KEY: CDS
         (B) LOCATION: 1336..2862

(xi) SEQUENCE DESCRIPTION: SEQ ID NO:7:
```

| | |
|---|---|
| CTGCAGAAGT TCACTCTTTC GCATATAGTG ACCCTCTTTT CTCTCAGCAT AATGGCACCT | 60 |
| ATCATATCAG TAAGGGGCGT ATTGTCTTTT CGAACAATGT ACAGCCCGAG AACTCTTTAC | 120 |
| TTCCACATCA CACCCCCGAC TCCTTAGTCA AGGATCTTTT TTCCGCTTTC CCCTCCGCTC | 180 |
| TCTTCCTCAT GCTGGACTGA CTTAACCTTG GTCTGCTCTA CTTTTCGGTT GTAAATACAT | 240 |
| GCAACACAAT AACTTTTTTA AGTGTTGTTA GACAACACTT TTACAAGACT CTGACTTTTA | 300 |
| ATGAGGTGGA GCATGAACCT TTTCCTCTTT CATCTTCTCC TTCAGATTAC AGTCAATATT | 360 |
| TTGGCAAAAG GCTAATTGAC AGCCTTTTAT AAGGGTTAAT CCCTTGTCGC TTATATTGAA | 420 |
| AACATGTTCT TTACGATCCG ATACTCTTCT TAAATCGAAA TTTTTCTCTA AATTGCGCCG | 480 |
| CAACAAAACT CCTTGAGAAA AGTACCAATA GAAATAGAAG GTAGCATTTT GCCTTTAAAT | 540 |
| TCCTTTTCTT TTCTTGGATT GTTCTTGAAA TGAATCTTAT TTGTGGATCT TTTTTGTTTT | 600 |
| TTTTAACCCG GCCGTGGTTC TCTGAATCAC GACCATAAAT TGTTTTAAAG TATGAGGAAA | 660 |
| TTATTATTGC TGATCGCGGC GTCCCTTTTG GGAGTTGGTC TTTACGCCCA AAACGCCAAG | 720 |
| ATTAAGCTTG ATGCTCCGAC TACTCGAACG ACATGCACGA ACAATAGCTT CAAGCAGTTC | 780 |
| GATGCAAGCT TTTCGTTCAA TGAAGTCGAG CTGAGAAAGG TGGAGACCAA AGGTGGTACT | 840 |
| TTCGCCTCAG TGTCAATTCC GGGTGCATTC CCGACCGGTG AGGTTGGTTC TCCCGAAGTG | 900 |
| CCAGCAGTTA GGAAGTTGAT TGCTGTGCCT GTCAAGCCA GACCTGTTGT TCGCGTGAAA | 960 |
| AGTTTTACCG AGCAAGTTTA CTGTCTGAAC CAATACGGTT CCGAAAAGCT CATGCCACAT | 1020 |
| CAACCCTCTA TGAGCAAGAG TGATGATCCC GAAAAGCTTC CCTTCGCTTA CAATGCTGCT | 1080 |
| GCTTATGCAC GCAAAGGTTT TGTCGGACAA GAACTGACCC AAGTAGAAAT GTTGGGGACA | 1140 |
| ATGCGTGGTG TTCGCATTGC AGCTCTTACC ATTAATCCTG TTCAGTATGA TGTAGTTGCA | 1200 |
| AACCAATTGA AGGTTAGAAA CAACATCGAA ATTGAAGTAA GCTTTCAGGG AGCTGATGAA | 1260 |
| GTAGCTACAC AACGTTTGTA TGATGCTTCT TTTAGCCCTT ATTTCGAAAC AGCTTATAAA | 1320 |

```
CAGCTCTTCA ATAGA GAT GTT TAT ACA GAT CAT GGC GAC TTG TAT AAT ACG    1371
               Asp Val Tyr Thr Asp His Gly Asp Leu Tyr Asn Thr
                 1               5                  10

CCG GTT CGT ATG CTT GTT GTT GCA GGT GCA AAA TTC AAA GAA GCT CTC    1419
Pro Val Arg Met Leu Val Val Ala Gly Ala Lys Phe Lys Glu Ala Leu
          15                  20                  25

AAG CCT TGG CTC ACT TGG AAG GCT CAA AAG GGC TTC TAT CTG GAT GTG    1467
Lys Pro Trp Leu Thr Trp Lys Ala Gln Lys Gly Phe Tyr Leu Asp Val
     30                  35                  40
```

```
CAT TAC ACA GAC GAA GCT GAA GTA GGA ACG ACA AAC GCC TCT ATC AAG         1515
His Tyr Thr Asp Glu Ala Glu Val Gly Thr Thr Asn Ala Ser Ile Lys
 45              50                  55                  60

GCA TTT ATT CAC AAG AAA TAC AAT GAT GGA TTG GCA GCT ACT GCT GCT         1563
Ala Phe Ile His Lys Lys Tyr Asn Asp Gly Leu Ala Ala Thr Ala Ala
                 65                  70                  75

CCG GTC TTC TTG GCT TTG GTT GGT GAC ACT GAC GTT ATT AGC GGA GAA         1611
Pro Val Phe Leu Ala Leu Val Gly Asp Thr Asp Val Ile Ser Gly Glu
             80                  85                  90

AAA GGA AAG AAA ACA AAA AAA GTT ACC GAC TTG TAT TAC ACT GCA GTC         1659
Lys Gly Lys Lys Thr Lys Lys Val Thr Asp Leu Tyr Tyr Thr Ala Val
             95                  100                 105

GAT GGC GAC TAT TTC CCT GAA ATG TAT ACT TTC CGT ATG TCT GCT TCT         1707
Asp Gly Asp Tyr Phe Pro Glu Met Tyr Thr Phe Arg Met Ser Ala Ser
        110                 115                 120

TCC CCA GAA GAA CTG ACG AAC ATC ATT GAT AAG GTA TTG ATG TAT GAA         1755
Ser Pro Glu Glu Leu Thr Asn Ile Ile Asp Lys Val Leu Met Tyr Glu
125                 130                 135                 140

AAG GCT ACT ATG CCG GAT AAG AGC TAT TTG GAA AAG GCC CTC TTG ATT         1803
Lys Ala Thr Met Pro Asp Lys Ser Tyr Leu Glu Lys Ala Leu Leu Ile
                145                 150                 155

GCC GGT GCT GAC TCC TAC TGG AAT CCT AAG ATA GGC CAG CAA ACC ATC         1851
Ala Gly Ala Asp Ser Tyr Trp Asn Pro Lys Ile Gly Gln Gln Thr Ile
            160                 165                 170

AAA TAT GCT GTA CAG TAT TAC TAC AAT CAA GAT CAT GGC TAT ACA GAT         1899
Lys Tyr Ala Val Gln Tyr Tyr Tyr Asn Gln Asp His Gly Tyr Thr Asp
            175                 180                 185

GTG TAC ACT TAC CCT AAA GCT CCT TAT ACA GGC TGC TAT AGT CAC TTG         1947
Val Tyr Thr Tyr Pro Lys Ala Pro Tyr Thr Gly Cys Tyr Ser His Leu
        190                 195                 200

AAT ACC GGT GTC GGC TTT GCC AAC TAT ACA GTG CAT GGA TCT GAG ACA         1995
Asn Thr Gly Val Gly Phe Ala Asn Tyr Thr Val His Gly Ser Glu Thr
205                 210                 215                 220

TCA TGG GCA GAT CCG TCC GTG ACC GCC ACT CAA GTG AAA GCA CTC ACA         2043
Ser Trp Ala Asp Pro Ser Val Thr Ala Thr Gln Val Lys Ala Leu Thr
                225                 230                 235

AAT AAG AAC AAA TAC TTC TTA GCT ATT GGG AAC TGC TGT GTT ACA GCT         2091
Asn Lys Asn Lys Tyr Phe Leu Ala Ile Gly Asn Cys Cys Val Thr Ala
            240                 245                 250

CAA TTC GAT TAT CCA CAG CCT TGC TTT GGA GAG GTA ATG ACT CGT GTC         2139
Gln Phe Asp Tyr Pro Gln Pro Cys Phe Gly Glu Val Met Thr Arg Val
            255                 260                 265

AAG GAG AAA GGT GCT TAT GCC TAT ATC GGT TCA TCT CCA AAT TCT TAT         2187
Lys Glu Lys Gly Ala Tyr Ala Tyr Ile Gly Ser Ser Pro Asn Ser Tyr
        270                 275                 280

TGG GGC GAG GAC TAC TAT TGG AGT GTG GGT GCT AAT GCA GTA TTT GGT         2235
Trp Gly Glu Asp Tyr Tyr Trp Ser Val Gly Ala Asn Ala Val Phe Gly
285                 290                 295                 300

GTT CAG CCT ACT TTT GAA GGT ACG TCT ATG GGT TCT TAT GAT GCT ACA         2283
Val Gln Pro Thr Phe Glu Gly Thr Ser Met Gly Ser Tyr Asp Ala Thr
                305                 310                 315

TTC TTG GAA GAT TCG TAC AAC ACA GTG AAC TCT ATT ATG TGG GCA GGT         2331
Phe Leu Glu Asp Ser Tyr Asn Thr Val Asn Ser Ile Met Trp Ala Gly
            320                 325                 330

AAT CTT GCT GCT ACT CAT GCC GAA AAT ATC GGC AAT GTT ACC CAT ATC         2379
Asn Leu Ala Ala Thr His Ala Glu Asn Ile Gly Asn Val Thr His Ile
            335                 340                 345

GGT GCT CAT TAC TAT TGG GAA GCT TAT CAT GTC CTT GGC GAT GGT TCG         2427
Gly Ala His Tyr Tyr Trp Glu Ala Tyr His Val Leu Gly Asp Gly Ser
```

```
                350                    355                    360
GTT ATG CCT TAT CGT GCA ATG CCT AAG ACC AAT ACT TAT ACG CTT CCT      2475
Val Met Pro Tyr Arg Ala Met Pro Lys Thr Asn Thr Tyr Thr Leu Pro
365                 370                 375                 380

GCT TCT CTG CCT CAG AAT CAG GCT TCT TAT AGC ATT CAG GCT TCT GCC      2523
Ala Ser Leu Pro Gln Asn Gln Ala Ser Tyr Ser Ile Gln Ala Ser Ala
                385                 390                 395

GGT TCT TAC GTA GCT ATT TCT AAA GAT GGA GTT TTG TAT GGA ACA GGT      2571
Gly Ser Tyr Val Ala Ile Ser Lys Asp Gly Val Leu Tyr Gly Thr Gly
                400                 405                 410

GTT GCT AAT GCC AGC GGT GTT GCG ACT GTG AAT ATG ACT AAG CAG ATT      2619
Val Ala Asn Ala Ser Gly Val Ala Thr Val Asn Met Thr Lys Gln Ile
                415                 420                 425

ACG GAA AAT GGT AAT TAT GAT GTA GTT ATC ACT CGC TCT AAT TAT CTT      2667
Thr Glu Asn Gly Asn Tyr Asp Val Val Ile Thr Arg Ser Asn Tyr Leu
430                 435                 440

CCT GTG ATC AAG GAA ATT CAG GCA GGA GAG CCT AGC CCC TAC CAG CCT      2715
Pro Val Ile Lys Glu Ile Gln Ala Gly Glu Pro Ser Pro Tyr Gln Pro
445                 450                 455                 460

GTT TCC AAC TTG ACT GCT ACA ACG CAG GGT CAG AAA GTA ACG CTC AAG      2763
Val Ser Asn Leu Thr Ala Thr Thr Gln Gly Gln Lys Val Thr Leu Lys
                465                 470                 475

TGG GAT GCC CCG AGC GCA AAG AAG GCA GAA GGT TCC CGT GAA GTA AAA      2811
Trp Asp Ala Pro Ser Ala Lys Lys Ala Glu Gly Ser Arg Glu Val Lys
                480                 485                 490

CGG ATC GGA GAC GGT CTT TTC GTT ACG ATC GAA CCT GCA AAC GAT GTA      2859
Arg Ile Gly Asp Gly Leu Phe Val Thr Ile Glu Pro Ala Asn Asp Val
                495                 500                 505

CGT GCCAACGAAG CCAAGGTTGT GCTCGCAGCA GACAACGTAT GGGGAGACAA           2912
Arg

TACGGGTTAC CAGTTCTTGT TGGATGCCGA TCACAATACA TTCGGAAGTG TCATTCCGGC    2972

AACCGGTCCT CTCTTTACCG GAAGAGCTTC TTCCAATCTT TACAGTGCGA ACTTCGAGTA   3032

TTTGATCCCG GCCAATGCCG ATCCTGTTGT TACTACACAC AATATTATCG TTACAGGACA   3092

GGGTGAAGTT GTAATCCCCG GTGGTGTTTA CGACTATTGC ATTACGAAGC CGGAACCTGC   3152

ATCCGGAAAG ATGTGGATCG CAGGAGATGG AGGCAACCAG CCTGCACGTT ATGACGATTT   3212

CACATTCGAA GCAGGCAAGA AGTACACCTT CACGATGCGT CGCGCCGGAA TGGGAGATGG   3272

AACTGATATG GAAGTCGAAG ACGATTCACC TGCAAGCTAT ACCTACACGG TGTATCGTGA   3332

CGGCACGAAG ATCAAGGAAG GTCTGACGGC TACGACATTC GAAGAAGACG GTGTAGCTGC   3392

AGGCAATCAT GAGTATTGCG TGGAAGTTAA GTACACAGCC GGCGTATCTC GAAGGTATG    3452

TAAAGACGTT ACGGTAGAAG GATCCAATGA ATTTGCTCCT GTACAGAACC TGACCGGTAG   3512

TGCAGTAGGT CAGAAAGTAA CGCTTAAGTG GGATGCACCT AATGGTACC               3561

(2) INFORMATION FOR SEQ ID NO:8:

(i) SEQUENCE CHARACTERISTICS:
        (A) LENGTH: 509 amino acids
        (B) TYPE: amino acid
        (D) TOPOLOGY: linear (ii) MOLECULE TYPE: protein (xi) SEQUENCE DESCRIPTION: SEQ ID NO:8:

Asp Val Tyr Thr Asp His Gly Asp Leu Tyr Asn Thr Pro Val Arg Met
1               5                   10                  15

Leu Val Val Ala Gly Ala Lys Phe Lys Glu Ala Leu Lys Pro Trp Leu
```

-continued

```
                20                  25                  30
Thr Trp Lys Ala Gln Lys Gly Phe Tyr Leu Asp Val His Tyr Thr Asp
             35                  40                  45
Glu Ala Glu Val Gly Thr Thr Asn Ala Ser Ile Lys Ala Phe Ile His
     50                  55                  60
Lys Lys Tyr Asn Asp Gly Leu Ala Ala Thr Ala Ala Pro Val Phe Leu
 65                  70                  75                  80
Ala Leu Val Gly Asp Thr Asp Val Ile Ser Gly Glu Lys Gly Lys Lys
                 85                  90                  95
Thr Lys Lys Val Thr Asp Leu Tyr Tyr Thr Ala Val Asp Gly Asp Tyr
             100                 105                 110
Phe Pro Glu Met Tyr Thr Phe Arg Met Ser Ala Ser Pro Glu Glu
         115                 120                 125
Leu Thr Asn Ile Ile Asp Lys Val Leu Met Tyr Glu Lys Ala Thr Met
     130                 135                 140
Pro Asp Lys Ser Tyr Leu Glu Lys Ala Leu Leu Ile Ala Gly Ala Asp
145                 150                 155                 160
Ser Tyr Trp Asn Pro Lys Ile Gly Gln Gln Thr Ile Lys Tyr Ala Val
                 165                 170                 175
Gln Tyr Tyr Tyr Asn Gln Asp His Gly Tyr Thr Asp Val Tyr Thr Tyr
             180                 185                 190
Pro Lys Ala Pro Tyr Thr Gly Cys Tyr Ser His Leu Asn Thr Gly Val
         195                 200                 205
Gly Phe Ala Asn Tyr Thr Val His Gly Ser Glu Thr Ser Trp Ala Asp
     210                 215                 220
Pro Ser Val Thr Ala Thr Gln Val Lys Ala Leu Thr Asn Lys Asn Lys
225                 230                 235                 240
Tyr Phe Leu Ala Ile Gly Asn Cys Cys Val Thr Ala Gln Phe Asp Tyr
                 245                 250                 255
Pro Gln Pro Cys Phe Gly Glu Val Met Thr Arg Val Lys Glu Lys Gly
             260                 265                 270
Ala Tyr Ala Tyr Ile Gly Ser Ser Pro Asn Ser Tyr Trp Gly Glu Asp
         275                 280                 285
Tyr Tyr Trp Ser Val Gly Ala Asn Ala Val Phe Gly Val Gln Pro Thr
     290                 295                 300
Phe Glu Gly Thr Ser Met Gly Ser Tyr Asp Ala Thr Phe Leu Glu Asp
305                 310                 315                 320
Ser Tyr Asn Thr Val Asn Ser Ile Met Trp Ala Gly Asn Leu Ala Ala
                 325                 330                 335
Thr His Ala Glu Asn Ile Gly Asn Val Thr His Ile Gly Ala His Tyr
             340                 345                 350
Tyr Trp Glu Ala Tyr His Val Leu Gly Asp Gly Ser Val Met Pro Tyr
         355                 360                 365
Arg Ala Met Pro Lys Thr Asn Thr Tyr Thr Leu Pro Ala Ser Leu Pro
     370                 375                 380
Gln Asn Gln Ala Ser Tyr Ser Ile Gln Ala Ser Ala Gly Ser Tyr Val
385                 390                 395                 400
Ala Ile Ser Lys Asp Gly Val Leu Tyr Gly Thr Gly Val Ala Asn Ala
                 405                 410                 415
Ser Gly Val Ala Thr Val Asn Met Thr Lys Gln Ile Thr Glu Asn Gly
             420                 425                 430
Asn Tyr Asp Val Val Ile Thr Arg Ser Asn Tyr Leu Pro Val Ile Lys
         435                 440                 445
```

```
Glu Ile Gln Ala Gly Glu Pro Ser Pro Tyr Gln Pro Val Ser Asn Leu
        450                 455                 460

Thr Ala Thr Thr Gln Gly Gln Lys Val Thr Leu Lys Trp Asp Ala Pro
465                 470                 475                 480

Ser Ala Lys Lys Ala Glu Gly Ser Arg Glu Val Lys Arg Ile Gly Asp
                485                 490                 495

Gly Leu Phe Val Thr Ile Glu Pro Ala Asn Asp Val Arg
                500                 505

(2) INFORMATION FOR SEQ ID NO:9:

(i) SEQUENCE CHARACTERISTICS:
        (A) LENGTH: 46 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (xi) SEQUENCE DESCRIPTION: SEQ ID NO:9:

Tyr Thr Tyr Thr Val Tyr Arg Asp Gly Lys Ile Lys Glu Gly Leu Thr
1               5                   10                  15

Ala Thr Thr Glu Asp Asp Gly Val Ala Thr Gly Asn His Glu Tyr Cys
                20                  25                  30

Val Glu Lys Tyr Thr Ala Gly Ser Val Ser Pro Lys Val Cys
                35                  40                  45

(2) INFORMATION FOR SEQ ID NO:10:

(i) SEQUENCE CHARACTERISTICS:
        (A) LENGTH: 20 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (v) FRAGMENT TYPE: N-terminal (xi) SEQUENCE DESCRIPTION: SEQ ID NO:10:

Tyr Thr Pro Val Glu Glu Lys Gln Asn Gly Arg Met Ile Val Ile Val
1               5                   10                  15

Ala Lys Lys Tyr
                20

(2) INFORMATION FOR SEQ ID NO:11:

(i) SEQUENCE CHARACTERISTICS:
        (A) LENGTH: 30 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (xi) SEQUENCE DESCRIPTION: SEQ ID NO:11:

Gln Leu Pro Phe Ile Phe Asp Val Ala Cys Val Asn Gly Asp Phe Leu
1               5                   10                  15

Phe Ser Met Pro Cys Phe Ala Glu Ala Leu Met Arg Ala Gln
```

```
            20                  25                  30
```

(2) INFORMATION FOR SEQ ID NO:12:

(i) SEQUENCE CHARACTERISTICS:
        (A) LENGTH: 31 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (xi) SEQUENCE DESCRIPTION: SEQ ID NO:12:

```
Gly Glu Pro Asn Pro Tyr Gln Pro Val Ser Asn Leu Thr Ala Thr Thr
1               5                   10                  15
Gln Gly Gln Lys Val Thr Leu Lys Trp Asp Ala Pro Ser Thr Lys
                20                  25                  30
```

(2) INFORMATION FOR SEQ ID NO:13:

(i) SEQUENCE CHARACTERISTICS:
        (A) LENGTH: 30 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (xi) SEQUENCE DESCRIPTION: SEQ ID NO:13:

```
Asp Gln Ala Asn Phe Leu Gln Cys Val Gly Ser Leu Met Cys Arg Leu
1               5                   10                  15
Asp Phe Phe Phe Glu Ala Val Met Pro Ile Phe Pro Ala Ala
                20                  25                  30
```

(2) INFORMATION FOR SEQ ID NO:14:

(i) SEQUENCE CHARACTERISTICS:
        (A) LENGTH: 25 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (xi) SEQUENCE DESCRIPTION: SEQ ID NO:14:

```
Gly Asn His Glu Tyr Cys Val Glu Val Lys Tyr Thr Ala Gly Val Ser
1               5                   10                  15
Pro Lys Val Cys Lys Asp Val Thr Val
                20                  25
```

(2) INFORMATION FOR SEQ ID NO:15:

(i) SEQUENCE CHARACTERISTICS:
        (A) LENGTH: 25 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (xi) SEQUENCE DESCRIPTION: SEQ ID NO:15:

```
Ala His Glu Lys Thr Tyr Pro Val Glu Asp Val Asn Cys Ser Tyr Val
 1               5                  10                  15

Lys Thr Val Cys Val Gly Gly Lys Val
            20                  25

(2) INFORMATION FOR SEQ ID NO:16:

(i) SEQUENCE CHARACTERISTICS:
        (A) LENGTH: 20 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (xi) SEQUENCE DESCRIPTION: SEQ ID NO:16:

Arg Met Phe Met Asn Tyr Glu Pro Gly Arg Tyr Thr Pro Val Glu Glu
 1               5                  10                  15

Lys Gln Asn Gly
            20

(2) INFORMATION FOR SEQ ID NO:17:

(i) SEQUENCE CHARACTERISTICS:
        (A) LENGTH: 20 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (xi) SEQUENCE DESCRIPTION: SEQ ID NO:17:

Thr Phe Ala Gly Phe Glu Asp Thr Tyr Lys Arg Met Phe Met Asn Tyr
 1               5                  10                  15

Glu Pro Gly Arg
            20

(2) INFORMATION FOR SEQ ID NO:18:

(i) SEQUENCE CHARACTERISTICS:
        (A) LENGTH: 49 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (xi) SEQUENCE DESCRIPTION: SEQ ID NO:18:

Asp Tyr Thr Tyr Thr Val Tyr Arg Asp Gly Thr Lys Ile Lys Glu Gly
 1               5                  10                  15

Leu Thr Ala Thr Thr Phe Glu Glu Asp Gly Val Ala Thr Gly Asn Met
            20                  25                  30

Glu Tyr Cys Val Cys Val Lys Tyr Thr Ala Gly Val Ser Pro Lys Val
                35                  40                  45

Cys (2) INFORMATION FOR SEQ ID NO:19:

(i) SEQUENCE CHARACTERISTICS:
```

(A) LENGTH: 25 amino acids
         (B) TYPE: amino acid
         (C) STRANDEDNESS: single
         (D) TOPOLOGY: Not Relevant (ii) MOLECULE TYPE: peptide (iii) HYPOTHETICAL: NO (xi) SEQUENCE DESCRIPTION: SEQ ID NO:19:

Tyr Thr Tyr Thr Val Tyr Arg Asp Gly Thr Lys Ile Lys Glu Gly Leu
1               5                  10                  15

Thr Ala Thr Thr Phe Glu Glu Asp Gly
            20                  25

(2) INFORMATION FOR SEQ ID NO:20:

(i) SEQUENCE CHARACTERISTICS:
         (A) LENGTH: 24 amino acids
         (B) TYPE: amino acid
         (C) STRANDEDNESS: single
         (D) TOPOLOGY: Not Relevant (ii) MOLECULE TYPE: peptide (iii) HYPOTHETICAL: NO (xi) SEQUENCE DESCRIPTION: SEQ ID NO:20:

Arg Asp Gly Thr Lys Ile Lys Glu Gly Leu Thr Ala Thr Thr Phe Glu
1               5                  10                  15

Glu Asp Gly Val Ala Thr Gly Asn
            20

(2) INFORMATION FOR SEQ ID NO:21:

(i) SEQUENCE CHARACTERISTICS:
         (A) LENGTH: 23 amino acids
         (B) TYPE: amino acid
         (C) STRANDEDNESS: single
         (D) TOPOLOGY: Not Relevant (ii) MOLECULE TYPE: peptide (iii) HYPOTHETICAL: NO (xi) SEQUENCE DESCRIPTION: SEQ ID NO:21:

Lys Ile Lys Glu Gly Leu Thr Ala Thr Thr Phe Glu Glu Asp Gly Val
1               5                  10                  15

Ala Thr Gly Asn His Glu Tyr
            20

(2) INFORMATION FOR SEQ ID NO:22:

(i) SEQUENCE CHARACTERISTICS:
         (A) LENGTH: 4 amino acids
         (B) TYPE: amino acid
         (C) STRANDEDNESS: single
         (D) TOPOLOGY: Not Relevant (ii) MOLECULE TYPE: peptide (iii) HYPOTHETICAL: NO (xi) SEQUENCE DESCRIPTION: SEQ ID NO:22:

Phe Glu Glu Asp
1

(2) INFORMATION FOR SEQ ID NO:23:

```
    (i) SEQUENCE CHARACTERISTICS:
        (A) LENGTH: 28 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (xi) SEQUENCE DESCRIPTION: SEQ ID NO:23:

Lys Trp Asp Ala Pro Asn Gly Thr Pro Asn Pro Asn Pro Asn Pro Asn
1               5                   10                  15

Pro Asn Pro Asn Pro Gly Thr Thr Thr Leu Ser Glu
            20                  25

(2) INFORMATION FOR SEQ ID NO:24:

(i) SEQUENCE CHARACTERISTICS:
        (A) LENGTH: 20 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (xi) SEQUENCE DESCRIPTION: SEQ ID NO:24:

Tyr Thr Pro Val Glu Glu Lys Glu Asn Gly Arg Met Ile Val Ile Val
1               5                   10                  15

Ala Lys Lys Tyr
            20
```

IMMUNOGENIC COMPOSITIONS COMPRISING PORPHYROMONAS GINGIVALIS PROTEINS AND/OR PEPTIDES AND METHODS

CROSS REFERENCE TO RELATED APPLICATIONS

This application claims priority from U.S. Provisional Application No. 60/013,945, filed Mar. 22, 1996.

STATEMENT RE FEDERALLY SPONSORED RESEARCH AND DEVELOPMENT

This invention was made, at least in part, with funding from the National Institutes of Health (Grant Nos. DE 09761, DE 09161, RR 03034, HL 26148 and HL 37090). Accordingly, the United States Government may have certain rights in this invention.

BACKGROUND OF THE INVENTION

The field of this invention is immunogenic compositions comprising bacterial proteases and/or peptides derived therefrom, more particularly those of *Porphyromonas gingivalis*, most particularly the arginine-specific proteases and immunogenic compositions containing Arg-gingipains and/or peptides derived therefrom, and the lysine-specific proteases termed Lys-gingipains herein and immunogenic compositions containing Lys-gingipain(s) and/or peptides derived therefrom. Those immunogenic compositions are useful in the protection of a mammal, including a human, from infection and pathology caused by *P. gingivalis*.

*Porphyromonas gingivalis* (formerly *Bacteroides gingivalis*) is an obligately anaerobic bacterium which is implicated in periodontal disease. *P. gingivalis* produces several distinct proteolytic enzymes; its proteinases are recognized as important virulence factors, together with other factors such as lipopolysaccharide and a polysaccharide capsule, fimbriae, lectin-like adhesins, hyaluronidase, keratinase, superoxide dismutase and hemagglutinating and hemolyzing activities. A number of physiologically significant proteins, including collagen, fibronectin, immunoglobulins, complement factors C3, C4, C5, and B, lysozyme, iron-binding proteins, plasma proteinase inhibitors, fibrin and fibrinogen, and factors of the plasma coagulation cascade system, are hydrolyzed by *P. gingivalis* proteases. Broad proteolytic activity plays a role in the evasion of host defense mechanisms and the destruction of gingival connective tissue in progressive periodontitis [Saglie et al. (1988) *J. Periodontal.* 59:259–265].

Progressive periodontitis is characterized by acute tissue degradation promoted by collagen digestion and a vigorous inflammatory response characterized by excessive neutrophil infiltration [White and Maynard (1981) *J. Periodontal Res.* 16:259–265]. Gingival crevicular fluid accumulates in periodontitis as periodontal tissue erosion progresses at the foci of the infection, and numerous plasma proteins are exposed to proteinases expressed by the bacteria at the injury site. Neutrophils are recruited to the gingiva, in part, by the humoral chemotactic factor C5a. The complement components C3 and C5 are activated by complex plasma proteases with "trypsin-like" specificities called convertases [Muller-Eberhard (1988) *Ann. Rev. Biochem.* 57:321–347]. The human plasma convertases cleave the α-chains of C3 and C5 at a specific site generating biologically active factors known as anaphylatoxins (i.e. C3a and C5a). The anaphylatoxins are potent proinflammatory factors exhibiting chemotactic and/or spasmogenic activities as well as promoting increased vascular permeability. The larger products from C3 and C5 cleavage (i.e. C3b and C5b) participate in functions including complement cascade activation, opsonization, and lytic complex formation.

There are conflicting data as to the number and types of proteinases produced by *P. gingivalis*. In the past, proteolytic activities of *P. gingivalis* were classified into two groups; those enzymes which specifically degraded collagen and the general "trypsin-like" proteinases which appeared to be responsible for other proteolytic activity. Chen et al. (1992) *J. Biol. Chem.* 267, 18896–18901 reported the first rigorous purification and biochemical characterization of an arginine-specific *P. gingivalis* protease; the purification of a lysine-specific proteinase of *P. gingivalis* is described by Pike et al. (1994) *J. Biol. Chem.* 269:406–411 [see also Potempa et al. (1995) *Perspectives in Drug Discovery and Design* 2:445–458].

SUMMARY OF THE INVENTION

An object of the present invention is to provide immunogenic compositions comprising at least one peptide corresponding in sequence to the N-terminus of at least one arginine-specific proteinase derived from *P. gingivalis*, preferably from Arg-gingipain, termed Arg-gingipain-1 (or RGP-1), having an apparent molecular mass of 50 kDa as estimated by sodium dodecyl sulfate polyacrylamide gel electrophoresis and an apparent molecular mass of 44 kDa as estimated by gel filtration chromatography, and enzymological properties as described hereinbelow. In a specifically exemplified RGP protein, the protein is characterized by an N-terminal amino acid sequence as given in SEQ ID NO:1 (YTPVEEKQNGRMIVIVAKKYEGDIKDFVDWKNQR) and by a C-terminal amino acid sequence as given in SEQ ID NO:2 (ELLR). A second Arg-specific gingipain has an N-terminal sequence as given in SEQ ID NO:24 (YTPVEEKENGRMIVIVAKKY), it differs from the sequence as given in SEQ ID NO:10 in that position 7 is Glu rather than Gln.

Within the scope of the present invention are methods for protecting a mammal, including a human, from periodontitis and/or other pathology caused at least in part by *P. gingivalis*, said method comprising the step of administering to said mammal an immunogenic composition comprising at least one peptide corresponding in sequence to the amino-terminus of at least one of RGP-1, RGP-2, HMW RGP, or one or more peptides derived from one or more of the foregoing proteins or having amino acid sequence(s) taken from the amino acid sequence(s) of one or more of the foregoing proteins, wherein said peptide or protein, when used in an immunogenic composition in an animal, especially a mammal or human, confers protection against infection by and/or periodontitis caused at least in part by *P. gingivitis*. Preferred immunogenic compositions for protecting mammals (e.g., man) from *P. gingivalis* infection do not include a hemagglutinin protein or peptide.

A further object of this invention are immunogenic compositions comprising an N-terminal peptide derived from the catalytic subunit of a high molecular weight Arg-gingipain (HMW RGP), which comprises a proteolytic component essentially as described hereinabove and at least one hemagglutinin component. A nucleotide sequence encoding the HMW RGP complex polyprotein is given in SEQ ID NO:5, nucleotides 949–6063 and the deduced amino acid sequence is given in SEQ ID NO:6. As specifically exemplified, the mature HMW RGP has a 50 kDa protease component (same as RGP-1) having a complete deduced amino acid sequence as given in SEQ ID NO:6 from amino acid 228 through amino acid 719 or in SEQ ID NO:4, amino acids 228–719. HMW RGP further comprises at least one hemagglutinin component. The encoded RGP-hemagglutinin complex is transcribed as a prepolyprotein, with the amino acid sequence of at least one hemagglutinin protein as given in SEQ ID NO:6 from amino acid 720–1091, from 1092–1492 and/or from 1430–1704.

Compositions and immunogenic preparations including but not limited to vaccines, comprising at least one peptide antigen derived from the N-terminus of an Arg-gingipain from *P. gingivalis* and/or a peptide derived from an Arg-gingipain, and/or a Lys-gingipain and a suitable carrier therefor are provided. Such immunogenic compositions and vaccines are useful, for example, in immunizing an animal, including a human, against infection by and/or the inflammatory response and tissue damage caused by *P. gingivalis* in periodontal disease. The vaccine preparations comprise an immunogenic amount of an Arg-specific proteinase, Lys-gingipain, or an immunogenic peptide fragment or subunit of either one or both of said Arg-gingipains and Lys-gingipains or other *P. gingivalis* protease. Such vaccines may comprise one or more N-terminal peptides from Arg-gingipains and/or one or more Lys-gingipains and/or an Arg-gingipain or Lys-gingipain in combination with another protein or other immunogen. By "immunogenic amount" is meant an amount capable of eliciting the production of antibodies directed against one or more Arg-gingipain and/or Lys-gingipain catalytic subunit (or one or more peptides whose amino acid sequence is derived from the foregoing proteins) in an individual or animal to which the vaccine has been administered.

Oligopeptides of the present invention include those of about 30 amino acids or less, and include those comprising sequences as given in SEQ ID NO:9, SEQ ID NO:10, SEQ ID NO:11, SEQ ID NO:12, SEQ ID NO:14, SEQ ID NO:16, SEQ ID NO:17, SEQ ID NO:18, SEQ ID NO:19, SEQ ID NO:20, SEQ ID NO:21, SEQ ID NO:23 and SEQ ID NO:24. These oligopeptides can be formulated into vaccine compositions which are effective in protecting an animal, including a human, from infection by *P. gingivalis* and from periodontitis caused by *P. gingivalis*.

BRIEF DESCRIPTION OF THE FIGURES

FIG. 3 provides a sequence comparison of enzymatically active components of HMW KGP and HMW RGP polyproteins, with dashes inserted to optimize alignment of the two sequences.

FIG. 5 graphically illustrates the results of competitive ELISA. Chamber fluid from mice immunized with heat-killed *P. gingivalis* was preincubated with increasing concentration of RGP-1 (light bars) and KGP (dark bars) as competing antigens before the mixture was added to a microtitration plate coated with whole *P. gingivalis* cells. The amount of antibody specifically bound to bacterial surface antigens was determined by subsequent binding of peroxidase-labeled goat anti-mouse IgG antibodies.

FIGS. 6A–6D illustrate Western-blot analyses of chamber fluid samples. Purified gingipains (RGP-1, RGP-2, and KGP) and samples of *P. gingivalis* vesicles and membranes were boiled, resolved by SDS-PAGE and transferred to nitrocellulose. The nitrocellulose was transiently stained with Ponceau S, the position of molecular weight markers (Pharmacia), RGP-2, and polypeptide chains constituting RGP-1 complex were marked (dots to the right of an appropriate lane), and incubated in chamber fluid obtained from mice immunized with either: FIG. 6A, the N-terminal peptide of the catalytic domain of RGPs (Peptide A) (1,000 fold dilution); FIG. 6B, RGP-1; FIG. 6C, (1,000 fold dilution), the peptide derived from the adhesin/hemagglutinin domain of RGP-1 (Peptide D) 100 fold dilution); FIG. 6D, heat killed *P. gingivalis* (1,000 fold dilution) or FIG. 6E, RGP-2 (1,000 fold dilution). Alkaline phosphatase-labeled goat anti-mouse IgG was then added and blots were developed.

DETAILED DESCRIPTION OF THE INVENTION

Abbreviations used herein for amino acids are standard in the art: X or Xaa represents an amino acid residue that has not yet been identified but may be any amino acid residue including but not limited to phosphorylated tyrosine, threonine or serine, as well as cysteine or a glycosylated amino acid residue. The abbreviations for amino acid residues as used herein are as follows: A, Ala, alanine; V, Val, valine; L, Leu, leucine; I, Ile, isoleucine; P, Pro, proline; F, Phe, phenylalanine; W, Trp, tryptophan; M, Met, methionine; G, Gly, glycine; S, Ser, serine; T, Thr, threonine; C, Cys, cysteine; Y, Tyr, tyrosine; N, Asn, asparagine; Q, Gln, glutamine; D, Asp, aspartic acid; E, Glu, glutamic acid; K, Lys, lysine; R, Arg, arginine; and H, His, histidine. Other abbreviations used herein include Bz, benzoyl; Cbz, carboxybenzoyl; pNA, p-nitroanilide; MeO, methoxy; Suc, succinyl; OR, ornithyl; Pip, pipecolyl; SDS, sodium dodecyl sulfate; TLCK, tosyl-L-lysine chloromethyl ketone; TPCK, tosyl-L-phenylalanine chloromethyl ketone; S-2238, D-Phe-Pip-Arg-pNA, S-2222, Bz-Ile-Glu-(γ-OR)-Gly-pNA; S-2288, D-Ile-Pro-Arg-pNA; S-2251, D-Val-Leu-Lys-pNA; Bis-Tris, 2-[bis(2-hydroxyethyl)amino]-2-(hydroxymethyl)-propane-1,3-diol; FPLC, fast protein liquid chromatography; HPLC, high performance liquid chromatography; Tricine, N-[2-hydroxy-1,1-bis(hydroxymethyl)ethyl] glycine; EGTA, [ethylene-bis(oxyethylene-nitrile) tetraacetic acid; EDTA, ethylenediamine-tetraacetic acid; Z-L-Lys-pNa, Z-L-Lysine-p-Nitroanilide; HMW, high molecular weight.

Arg-gingipain (RGP) is the term given to a *P. gingivalis* enzyme with specificity for proteolytic and/or amidolytic activity for cleavage of a peptide and/or an amide bond, in which L-arginine contributes the carboxyl group. The Arg-gingipains described herein have identifying characteristics of cysteine dependence, inhibition response, $Ca^{2+}$-stabilization and glycine stimulation. Particular forms of Arg-gingipain are distinguished by the apparent molecular masses of the mature proteins (as measured without boiling before SDS-PAGE). See also Chen et al (1992) supra. Arg-gingipains of the present invention have no amidolytic or proteolytic activity for peptide and/or amide bonds in which L-lysine contributes the —COOH moiety.

Figure 1:
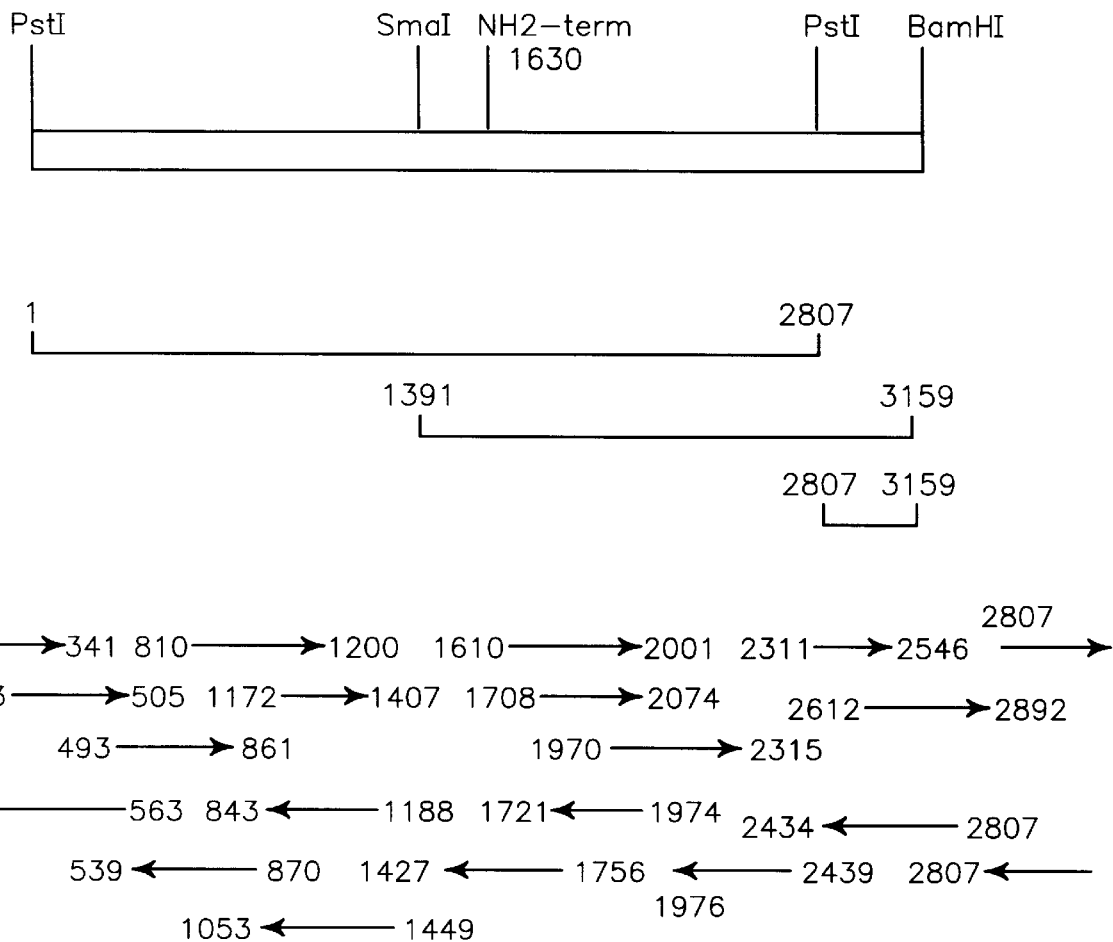
FIG. 1 illustrates the composite physical map of HMW RGP Arg-gingipain-2 DNA clones. The first codon of the mature gingipain is indicated. Clones PstI(1) /PstI(2807), SmaI(1391)/BamHI(3159), and PstI(2807)/BamHI(3159) are represented. The arrows indicate the extent and direction of sequencing. M13 primers and internal primers were used to sequence both strands of the putative HMW RGP gene, initially as double strand sequencing on clone PstI(1)/PstI (2807) and then as single strand sequencing on PstI(1)/PstI (2807) clone and on PstI(2807)/BamHI(3159) clone in both directions. The junction PstI(2807) was sequenced on double stranded clone SmaI(1391)/BamHI(3159). Only restriction sites employed in cloning are indicated.
Figure 2:
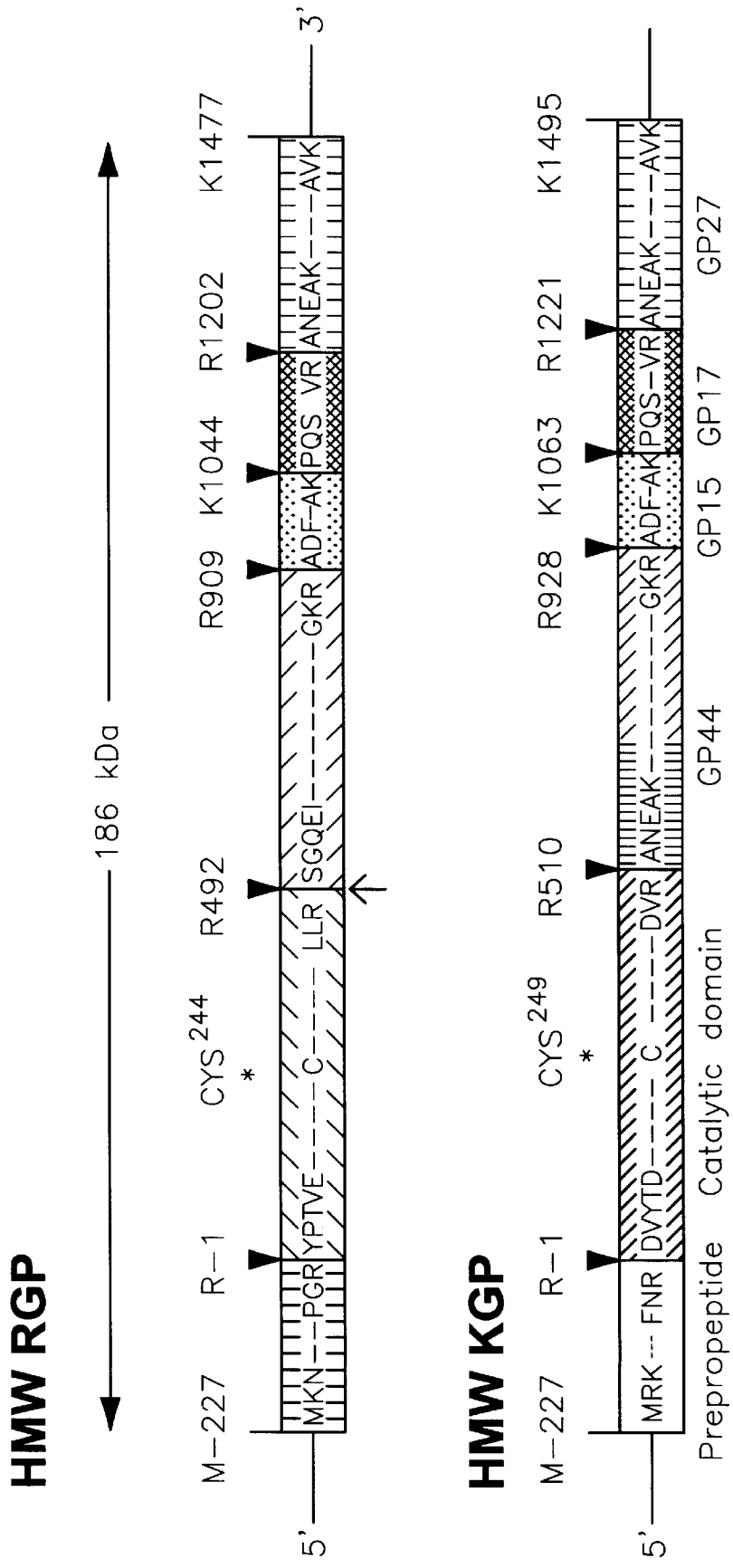
FIG. 2 presents a comparison of the polyprotein structures of HMW RGP and HMW KGP. Identical shading in the two diagrams indicates regions of amino acid sequence identity.

Antibodies specific for RGPs are produced in adult periodontitis patients, with the majority being reactive with antigenic determinants in the hemagglutinin/adhesin domain of RGP-1, [Curtiss et al. (1996) *Infect. Immun.* 64:2532]. Although patients with a history of destructive disease frequently demonstrate an elevated IgG response to *P. gingivalis*, these antibodies are apparently ineffective at limiting continued disease progression [Turner et al. (1989) *Microbios* 60:133; Yoshimura et al. (1987) *Microbiol. Immunol.* 31:935; Gunsolley et al. (1990) *J. Periodontol.* 61:412; Naito et al. (1987) *Infect. Immun.* 55:832]. In several animal studies, induction of an immune response to certain components of *P. gingivalis* exacerbates disease [McArthur and Clark (1993) *J. Periodontol.* 64:807]. Animal experiments described herein have demonstrated the protective effect of *P. gingivalis*-specific antibodies produced against peptides derived from N-terminus of RGP-1 (FIG. 1).

Arg-gingipain (RGP-1) is the name given herein to a protein characterized as having a molecular mass of 50 kDa as measured by SDS-PAGE and 44 kDa as measured by gel filtration over Sephadex G-150, having amidolytic and/or proteolytic activity for substrates having L-Arg in the $P_1$ position, i.e. on the N-terminal side of the peptide bond to be hydrolyzed, dependent on cysteine (or other thiol groups for full activity), having sensitivity to cysteine protease group-specific inhibitors including E64, iodoacetamide, iodoacetic acid, and N-methylmaleimide, leupeptin, antipain, trans-epoxysuccinyl-L-leucylamido-(4-guanidino)butane, TLCK, TPCK, p-aminobenzamidine, N-chlorosuccinamide, and chelating agents including EDTA and EGTA, but being resistant to inhibition by human cystatin C, α2-macroglobulin, α1-proteinase inhibitor, antithrombin III, α2-antiplasmin, serine protease group-specific inhibitors including diisopropylfluorophosphate, phenylmethyl sulfonylfluoride and 3,4-diisochlorocoumarin. The amidolytic and/or proteolytic activities are stabilized by $Ca^{2+}$ and stimulated by glycine-containing peptides and glycine analogs. Arg-gingipain-1 (RGP-1) is the 50 kDa protein whose purification and characterization was disclosed in Chen et al. (1992) supra and Wingrove et al. (1992) supra.

Arg-gingipain-2 (RGP-2) is a 50 kDa arginine-specific proteinase whose purification is first described hereinbelow. RGP-1 is distinguished from RGP-2 in that RGP-1 is not retained during chromatography over DE-52; RGP-2 is eluted from Whatman DE-52 with salt. A comparison of the primary structures of RGP-1 and RGP-2 is presented in Table 2.

An exemplified Arg-gingipain termed HMW RGP herein has an apparent molecular mass of 95 kDa as determined by SDS-PAGE without boiling of samples. When boiled, it dissociates into components of 50 kDa, 43 kDa, 27 kDa and 17 kDa. Arg-gingipain-1 (RGP-1) is the name given to the 50 kDa, enzymatically active component of the high molecular weight complex.

The complete amino acid sequence of the exemplified mature RGP-1 is given in SEQ ID NO:6, from amino acids 228–719. A second exemplary amino acid sequence is given in SEQ ID NO:4, amino acids 1 through 510. The complete coding sequence for the HMW RGP precursor polyprotein is given in SEQ ID NO:5, nucleotides 949–6063. In nature these proteins are produced by *Porphyromonas gingivalis*; they can be purified from cells or from culture supernatant using the methods provided herein. These proteins can also be produced recombinantly in suitable host cells genetically engineered to contain and express the exemplified (or synonymous) coding sequences.

As used herein with respect to RGP-1 or RGP-2, a substantially pure Arg-gingipain preparation means that there is only one protein band visible after silver-staining an SDS polyacrylamide gel run with the preparation, and the only amidolytic and/or proteolytic activities are those with specificity for L-arginine in the $P_1$ position relative to the bond cleaved. A substantially pure high molecular weight Arg-gingipain preparation has only one band (95 kDa) on SDS-PAGE (sample not boiled) or four bands (50 kDa, 43 kDa, 27 kDa, 17 kDa; sample boiled). Using a higher resolution tricine SDS-PAGE system, an additional component of 19 kDa has been detected in HMW RGP [Pavloff et al. (1995) supra]. No amidolytic or proteolytic activity for substrates with lysine in the $P_1$ position is evident in a substantially pure HMW RGP. Substantially pure Arg-gingipain is substantially free of naturally associated components when separated from the native contaminants which accompany them in their natural state. Thus, Arg-gingipain that is chemically synthesized or recombinantly synthesized in a cellular system different from the cell from which it naturally originates will be substantially free from its naturally associated components.

Techniques for chemical synthesis of polypeptides are described, for example, in Merrifield (1963) *J. Amer. Chem. Soc.* 85:2149–2154. A chemically synthesized Arg-gingipain protein or peptide derived therefrom is considered an "isolated" polypeptide or peptide.

Recombinantly produced RGP-1 and HMW RGP can be obtained by culturing host cells genetically engineered to contain and express the non-naturally occurring (recombinant) polynucleotides comprising nucleotide sequences encoding an Arg-gingipain as described herein under conditions suitable to attain expression of the proteinase-encoding sequence. See, e.g., U.S. Pat. No. 5,523,390, incorporated by reference herein.

Example 1 below and U.S. Pat. No. 5,523,390 describe the purification of a 50 kDa RGP-1 and HMW RGP from *P. gingivalis* culture supernatant, i.e., from a natural source. Various methods for the isolation of an Arg-gingipain from other biological material, such as from nonexemplified strains of *P. gingivalis* or from cells transformed with recombinant polynucleotides encoding such proteins, may be accomplished by methods known in the art. Various methods of protein purification are known in the art, including those described, e.g., in *Guide to Protein Purification*, ed. Deutscher, Vol. 182 of *Methods in Enzymology* (Academic Press, Inc., San Diego, 1990) and Scopes, *Protein Purification: Principles and Practice* (Springer-Verlag, New York, 1982).

Further analysis of the high molecular weight fractions containing Arg-specific amidolytic and proteolytic activity revealed that HMW RGP contained proteins of 44 kDa, subsequently identified as a hemagglutinin, and 27 kDa and 17 kDa, which are also postulated to have hemagglutinating activity. The empirically determined N-terminal amino acid sequence of the complexed 44 kDa protein corresponds to amino acids 720–736 of SEQ ID NO:6.

Purified RGP-1 exhibits an apparent molecular mass of about 50 kDa as determined by SDS-polyacrylamide gel electrophoresis. The size estimate obtained by gel filtration on high resolution agarose (Superose 12, Pharmacia, Piscataway, N.J.) is 44 kDa. N-terminal sequence analysis through 43 residues gave a unique structure which showed no homology with any other proteins, based on a comparison in the protein NBRS data base, release 39.0. The sequence obtained is as follows: YTPVEEKQNGRMIVI-VAKKYEGDIKDFVDWKNQR (SEQ ID NO:1). The C-terminal amino acid sequence of the gingipain-1 (major form recognized in zymography SDS-PAGE, 0.1% gelatin in gel), was found to be ELLR (SEQ ID NO:2). This corresponds to the amino acids encoded at nucleotides 3094–3105 in SEQ ID NO:3 and nucleotides 3094–3105 in SEQ ID NO:5, consistent with autoproteolytic processing of the precursor polyprotein to produce the mature 50 kDa RGP-1 protein. Without wishing to be bound by theory, it is proposed that SEQ ID NO:3 comprises the coding sequence for RGP-1, the enzymatically active component of the high molecular weight form of Arg-gingipain. This is consistent with the observation that there are at least two genes with substantial nucleic acid homology to the Arg-gingipain-specific probe.

Because progressive periodontitis is characterized by tissue degradation, collagen destruction and a strong inflammatory response, and because *P. gingivalis* exhibits complement-hydrolyzing activity, purified RGP-1 was tested for proteinase activity using purified human complement C3 and C5 as substrates [see Wingrove et al. (1992) *J. Biol. Chem.* 269:18902–18907]. RGP-1 selectively cleaved the C3 α-chain. C3a biological activity in the C3 digestion mixture was not observed, and the C3a-like fragment released from the α-chain was extensively degraded by RGP-1. When human C5 is subjected to prolonged digestion by RGP-1, functional C5a accumulates in the digestion mixture. RGP-1 injected into guinea pig skin enhances vascular permeability at concentrations greater than $10^{-8}$ M and causes neutrophil accumulation at the site of injection. This activity was dependent on proteolytic activity of the RGP-1 protein. The results demonstrate the ability of RGP-1 to elicit an inflammatory response.

The N-terminal amino acid sequence of the 50 kDa component of the HMW RGP is identical to the first 22 amino acids of the 50 kDa RGP-1. Characterization of the HMW RGP activity showed the same dependence on cysteine (or other thiols) and the same spectrum of response to potential inhibitors. Although the HMW RGP and RGP-1 amidolytic activity was stimulated by Gly-Gly, the response for RGP-2 was only about half that observed for RGP-1 and HMW RGP.

The cloning and coding sequences for Arg-gingipain are described in U.S. Pat. No. 5,523,390. SEQ ID NO:3 herein is the DNA sequence of the 3159 bp PstI/BamHI fragment from *P. gingivalis* strain HG66 (W83). An exemplified sequence encoding mature RGP-1 extends from 1630–3105. The first nucleotide belongs to the PstI cloning site. The first ATG appears at nucleotide 949 and is followed by a long open reading frame (ORF) of 2210 nucleotides. The first ATG is following by 8 others in frame (at nucleotides 1006, 1099, 1192, 1246, 1315, 1321, 1603, and 1609). Which of these initiation codons are used in translation of the Arg-gingipain-2 precursor can be determined by expression of the polyprotein in bacteria and subsequent N-terminal sequence analysis of preprotein intermediates. The primary structure of the mature Arg-gingipain is derived from the empirical N-terminal and C-terminal sequences and molecular mass. Thus, a mature RGP has an amino terminus starting at nucleotide residue 1630 in SEQ ID NO:3 and at amino acid 228 in SEQ ID NO:4; both mature proteins are cleaved after an Arg. The 50 kDa and the 44 kDa bands from Ez-L-Arg-pNa activity peaks are identical in sequence to the deduced amino acid sequence of gingipain, encoded respectively at nucleotides 1630–1695 and at nucleotides 3106–3156. The carboxyl terminus is most likely derived from autoproteolytic processing after the Arg residue encoded at 3103–3105 where the coding sequence of hemagglutinin starts (nucleotide 3106). The deduced 492 amino acids of RGP-1 give rise to a protease molecule with a calculated molecular weight of 54 kDa, which correlates well with the molecular mass of 50 kDa determined by SDS-PAGE analysis.

The skilled artisan recognizes that other *P. gingivalis* strains can have coding sequences for a protein with the distinguishing characteristics of an Arg-gingipain; those coding sequences may be identical to or synonymous with the exemplified coding sequence, or there may be some variation(s) in the encoded amino acid sequence. An Arg-gingipain coding sequence from a *P. gingivalis* strain other than H66 can be identified by, e.g. hybridization to a polynucleotide or an oligonucleotide having the whole or a portion of the exemplified coding sequence for mature gingipain, under stringency conditions appropriate to detect a sequence of at least 70% homology.

SEQ ID NO:5 presents the nucleotide sequence encoding the complete prepolyprotein sequence, including both the protease component and the hemagglutinin component(s) of HMW RGP. The coding sequence extends from an ATG at nucleotide 949 through a TAG stop codon ending at nucleotide 6063 in SEQ ID NO:5. The deduced amino acid sequence is given in SEQ ID NO:6. Cleavage of the precursor protein after the Arg residue at 227 amino acid residues into the precursor protein removes the N-terminal precursor portion and after the Arg residue at amino acid 719 releases a low molecular weight Arg-gingipain catalytic component and at least one hemagglutinin component.

The cloning and sequencing of the lysine-specific gingipain (KGP) is described in U.S. Pat. No. 5,475,077, which is incorporated by reference herein. The coding sequence of the 60 kDa active component of the Lys-gingipain complex extends through nucleotide 2863 in SEQ ID NO:7. The amino acid sequence identical to the amino-terminal sequence of the 44, 27 and 17 kDa Lys-gingipain complex components, at least one of which is believed to function as a hemagglutinin, is encoded at nucleotides 2864–2938 in SEQ ID NO:7. Without wishing to be bound by any particular theory, it is believed that an Arg-specific protease processes the polyprotein which is (in part) encoded within the nucleotide sequence of SEQ ID NO:7. The predicted molecular mass of 55.9 kDa for a 509 amino acid protein encoded from nucleotides 1336–2863 is consistent with the empirically determined estimate of 60 kDa (SDS-PAGE).

Both HMW KGP (see U.S. Pat. No. 5,475,077), and HMW RGP can to erythrocytes, laminin and fibrinogen even if the catalytic domains are inactivated. However, TLCK-inactivated 50 kDa RGP cannot bind although the active form can degrade fibrinogen, fibronectin and laminin. Without wishing to be bound by theory, it is postulated that three nearly identical repeated sequences of HMW KGP and HMW RGP mediate this adhesion. Polyclonal antibodies have been made in response to a chemically synthesized peptide encompassing the repeated sequence (YTYTVYRDGKIKEGLTATTEDDGVATG-NHEYCVEKYTAGSVSPKVC) (SEQ ID NO:9), which is close to a consensus sequence for the three repeating domains of HMW RGP and HMW KGP. These antibodies do not affect the catalytic activities of these proteases.

An Arg-gingipain coding sequence was also isolated from P. gingivalis W50. A 3.5 kb BamHI fragment was sequenced; it exhibited 99% nucleotide sequence identity with the 3159 bp fragment of P. gingivalis W83 (HG66) DNA containing Arg-gingipain coding sequence. A comparison of the deduced amino acid sequences of the encoded Arg-gingipains revealed 99.9% identity.

Regardless of the affinity for Arg-Sepharose and the differences in specific activities, the purified form of RGP-2 gave in SDS-PAGE a single band with molecular mass of 48.5 kDa, slightly lower than for the catalytic domain of HMW RGP (50.0 kDa). It is also slightly lower than for RGP-1, where the molecular mass was refined using laser densitometry scanning of the gel to 49.0 kDa from the previously reported 50 kDa.

In contrast to the uniform molecular mass, analysis of the purified forms of RGP-2 by means of zymography on gelatin SDS-PAGE revealed reciprocal heterogeneity in active band patterns and substantial differences in an electrophoretic mobility in comparison to RGP-1. The major activity zone of the latter gingipain was located in the 68–70 kDa area of the gel and did not have equivalent neither in starting material nor in the activity peaks separated by gel filtration chromatography. This indicates that the contribution of RGP-1 to the total proteolytic activity of P. gingivalis H66 is relatively minor, a conclusion which is in keeping with the low activity against Bz-L-Arg-pNA recovered in Vo of the DE-52 (300 activity units) as compared to the activity eluted from the column with NaCl (5,819 activity units).

Partial primary structure analyses of the 48.5–50 kDa forms of Arg-specific gingipain show that the amino-termini of three forms of RGP-2, which have been sequenced up to 50 amino acid residues and with one exception, Glu9 instead Gln9, have identical primary structures (RGP-1 and the catalytic domain of HMW RGP). To further characterize possible structural differences between the Arg-Sepharose affinity variants of RGP-2 and RGP-1, a sample of each enzyme was S-ethylpyridylated and subjected to autodigestion or trypsin digestion. Due to the RGPs' strict specificity for Arg-X peptide bonds, autodigestion resulted in a discrete peptide band pattern with relatively high molecular masses within the range from 3 kDa to 27 kDa. The pattern was identical for the affinity variants of RGP-2, but it showed some differences in comparison to RGP-1, despite striking similarities of the overall peptide maps.

The structures of RGP-2 variants was further investigated by reverse phase HPLC (C18 column) after tryptic digestion of the S-pyridylethylated proteins. Exactly the same peptide maps were again obtained, indicating that at the primary structure level, the Arg-Sepharose affinity variants of RGP-2 are indistinguishable. In contrast, the peptide map of RGP-1 differs slightly from that of RGP-2. Several HPLC-purified tryptic peptides derived from RGP-1 and RGP-2 have been subjected to amino-terminal sequence analyses and in both cases, the same sequence overlapping with the following fragments of the catalytic domain of HMW RGP as inferred from DNA structure: 61-Gln-80-Lys, 92-Ser-112-Arg, 142-Trp-184-Lys, 194-Asn-230-Lys. In one case, however, the peptide of RGP-2 which did not have an equivalent in the reverse phase HPLC peptide map of RGP-1 gave unique, though related, sequence, that differed from the latter one in 13 out of 29 compared amino acid residues (Table 2). Although RGP-1 and RGP-2 are closely related proteins, they differ in primary structure and therefore must be the products of different genes.

SEQ ID NO:3 and SEQ ID NO:5 both represent sequences from P. gingivalis. However, it is understood that there will be some variations in the amino acid sequences and encoding nucleic acid sequences for Arg-gingipains from different P. gingivalis strains. The ordinary skilled artisan can readily identify and isolate Arg-gingipain-encoding sequences from other strains where there is at least 70% homology to the specifically exemplified sequences herein using the sequences provided herein taken with what is well known to the art, e.g., polymerase chain reaction and/or nucleic acid hybridization techniques. Also within the scope of the present invention are Arg-gingipain where the protease (or proteolytic component) has at least about 85% amino acid sequence identity with an amino acid sequence exemplified herein.

It is also understood by the skilled artisan that there can be limited numbers of amino acid substitutions in a protein without significantly affecting function, and that nonexemplified gingipain-1 proteins can have some amino acid sequence diversion from the exemplified amino acid sequence. Such naturally occurring variants can be identified, e.g., by hybridization to the exemplified (mature) RGP-1 or HMW RGP coding sequence (or a portion thereof capable of specific hybridization to Arg-gingipain sequences) under conditions appropriate to detect at least about 70% nucleotide sequence homology, preferably about 80%, more preferably about 90% and most preferably 95–100% sequence homology. Preferably the encoded Arg-gingipain protease or proteolytic component has at least about 85% amino acid sequence identity to an exemplified Arg-gingipain amino acid sequence.

It is well known in the biological arts that certain amino acid substitutions can be made in protein sequences without affecting the function of the protein. Generally, conservative amino acids are tolerated without affecting protein function.

Similar amino acids can be those that are similar in size and/or charge properties, for example, aspartate and glutamate and isoleucine and valine are both pairs of similar amino acids. Similarity between amino acid pairs has been assessed in the art in a number of ways. For example, Dayhoff et al. (1978) in *Atlas of Protein Sequence and Structure,* Volume 5, Supplement 3, Chapter 22, pages 345–352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

In another embodiment of the present invention, polyclonal and/or monoclonal antibodies capable of specifically binding to a proteinase or fragments thereof are provided. The term antibody is used to refer both to a homogenous molecular entity, or a mixture such as a serum product made up of a plurality of different molecular entities. Monoclonal or polyclonal antibodies specifically reacting with the Arg-gingipains can be made by methods known in the art. See, e.g., Harlow and Lane (1988) *Antibodies: A Laboratory Manual,* Cold Spring Harbor Laboratories; Goding (1986) *Monoclonal Antibodies: Principles and Practice,* 2ed., Academic Press, New York; and Ausubel et al. (1987) vide infra. Also, recombinant immunoglobulins may be produced by methods known in the art, including but not limited to, the methods described in U.S. Pat. No. 4,816,567. Monoclonal antibodies with affinities of $10^8$ $M^{-1}$, preferably $10^9$ to $10^{10}$ or more are preferred.

Antibodies specific for Arg-gingipains are useful, for example, as probes for screening DNA expression libraries or for detecting the presence of Arg-gingipains in a test sample. Frequently, the polypeptides and antibodies will be labeled by joining, either covalently or noncovalently, a substance which provides a detectable signal. Suitable labels include but are not limited to radionuclides, enzymes, substrates, cofactors, inhibitors, fluorescent agents, chemiluminescent agents, magnetic particles and the like. U.S. patents describing the use of such labels include, but are not limited to, U.S. Pat. Nos. 3,817,837; 3,850,752; 3,939,350; 3,996,345; 4,277,437; 4,275,149; and 4,366,241.

Antibodies specific for Arg-gingipain(s) and capable of inhibiting its proteinase activity are useful in treating animals, including man, suffering from periodontal disease. Such antibodies can be obtained by the methods described above and subsequently screening the Arg-gingipain-specific antibodies for their ability to inhibit proteinase activity.

Compositions and immunogenic preparations, including vaccine compositions, comprising substantially purified recombinant Arg-gingipain(s) or an immunogenic peptide of an Arg-gingipain capable of inducing protective immunity in a suitably treated mammal and a suitable carrier therefor are provided. Alternatively, hydrophilic regions of the proteolytic component or hemagglutinin component(s) of Arg-gingipain can be identified by the skilled artisan, and peptide antigens can be synthesized and conjugated to a suitable carrier protein (e.g., bovine serum albumin or keyhole limpet hemocyanin) if needed for use in vaccines or in raising antibody specific for Arg-gingipains. Immunogenic compositions are those which result in specific antibody production when injected into a human or an animal. Such immunogenic compositions or vaccines are useful, for example, in immunizing an animal, including humans, against infection and/or inflammatory response and tissue damage caused by *P. gingivalis* in periodontal disease. The vaccine preparations comprise an immunogenic amount of one or more Arg-gingipains or an immunogenic fragment(s) or subunit(s) thereof. Such vaccines can comprise one or more Arg-gingipains or in combination with another protein or other immunogen, or an epitopic peptide derived therefrom. A preferred peptide has an amino acid sequence identical to the N-terminal sequence of RGP-1. An "immunogenic amount" means an amount capable of eliciting the production of antibodies directed against Arg-gingipain(s) in an individual to which the vaccine has been administered.

Immunogenic carriers can be used to enhance the immunogenicity of the proteinases, proteolytic components, hemagglutinins or peptides derived in sequence from any of the foregoing. Such carriers include but are not limited to proteins and polysaccharides, liposomes, and bacterial cells and membranes. Protein carriers may be joined to the proteinases or peptides derived therefrom to form fusion proteins by recombinant or synthetic means or by chemical coupling. Useful carriers and means of coupling such carriers to polypeptide antigens are known in the art.

The immunogenic compositions and/or vaccines may be formulated by any of the means known in the art. They are typically prepared as injectables, either as liquid solutions or suspensions. Solid forms suitable for solution in, or suspension in, liquid prior to injection may also be prepared. The preparation may also, for example, be emulsified, or the protein(s)/peptide(s) encapsulated in liposomes. Where mucosal immunity is desired, the immunogenic compositions advantageously contain an adjuvant such as the non-toxic cholera toxin B subunit (see, e.g., U.S. Pat. No. 5,462,734). Cholera toxin B subunit is commerically available, for example, from Sigma Chemical Company, St. Louis, Mo. Other suitable adjuvants are available and may be substituted therefor. It is preferred that an adjuvant for an aerosol immunogenic (or vaccine) formulation is able to bind to epithelial cells and stimulate mucosal immunity.

Among the adjuvants suitable for mucosal administration and for stimulating mucosal immunity are organometallopolymers including linear, branched or cross-linked silicones which are bonded at the ends or along the length of the polymers to the particle or its core. Such polysiloxanes can vary in molecular weight from about 400 up to about 1,000,000 daltons; the preferred length range is from about 700 to about 60,000 daltons. Suitable functionalized silicones include (trialkoxysilyl) alkyl-terminated polydialkylsiloxanes and trialkoxysilyl-terminated polydialkylsiloxanes, or example, 3-(triethyoxysilyl) propyl-terminated polydimethylsiloxane. See U.S. Pat. No. 5,571,531, incorporated by reference herein. Phosphazene polyelectrolytes can also be incorporated into immunogenic compositions for transmucosal administration (intranasal, vaginal, rectal, respiratory system by aerosol administration) (See U.S. Pat. No. 5,562,909).

Alternatively, mucosal immunity can be triggered by the administration to mucosal surfaces, for example, orally, of recombinant avirulent bacterial cells which express a protective epitope derived from a *P. gingivalis* protease, for example, RGP-1, HMW RGP or RGP-2, of particular interest is the expression of at least about 15 amino acids from the N-terminus of the RGP-2 or the N-terminus of a catalytic subunit of HMW RGP or HMW KGP. Avirulent *Salmonella typhi* and avirulent *Salmonella typhimurium* strains, suitable vectors and suitable promoters for driving expression are known to the art. The protective epitopes are advantageously expressed as fusions with other proteins, such as *Salmonella flagellin,* tetanus toxin fragment C, and *E. coli* LamB or MalE.

The active immunogenic ingredients are often mixed with excipients or carriers which are pharmaceutically acceptable and compatible with the active ingredient. Suitable excipients include but are not limited to water, saline, dextrose, glycerol, ethanol, or the like and combinations thereof. The concentration of the immunogenic polypeptide in injectable formulations is usually in the range of 0.2 to 5 mg/ml.

In addition, if desired, the vaccines may contain minor amounts of auxiliary substances such as wetting or emulsifying agents, pH buffering agents, and/or adjuvants which enhance the effectiveness of the vaccine. Examples of adjuvants which are effective include, but are not limited to, aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3hydroxyphosphoryloxy)-ethylamine (CGP 19835A, referred to as MTP-PE); and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogen resulting from administration of the immunogen in vaccines which are also comprised of the various adjuvants. Such additional formulations and modes of administration as are known in the art may also be used.

RGP-1 and/or RGP-2 or HMW RGP and/or epitopic fragments or peptides of sequences derived therefrom or from other P. gingivalis proteins having primary structure similar (more than 90% identity) to HMW RGP or HMW KGP may be formulated into vaccines as neutral or salt forms. Pharmaceutically acceptable salts include, but are not limited to, the acid addition salts (formed with free amino groups of the peptide) which are formed with inorganic acids, e.g., hydrochloric acid or phosphoric acids; and organic acids, e.g., acetic, oxalic, tartaric, or maleic acid. Salts formed with the free carboxyl groups may also be derived from inorganic bases, e.g., sodium, potassium, ammonium, calcium, or ferric hydroxides, and organic bases, e.g., isopropylamine, trimethylamine, 2-ethylamino-ethanol, histidine, and procaine.

The immunogenic compositions or vaccines are administered in a manner compatible with the dosage formulation, and in such amount as prophylactically and/or therapeutically effective. The quantity to be administered, generally in the range of about 100 to 1,000 μg of protein per dose, more generally in the range of about 5 to 500 μg of protein per dose, depends on the subject to be treated, the capacity of the individual's immune system to synthesize antibodies, and the degree of protection desired. Precise amounts of the immunogen may depend on the judgment of the physician or dentist and may be peculiar to each individual, but such a determination is within the skill of such a practitioner.

The vaccine or other immunogenic composition can be given in a single dose or multiple dose schedule. A multiple dose schedule is one in which a primary course of vaccination may include 1 to 10 or more separate doses, followed by other doses administered at subsequent time intervals as required to maintain and or reinforce the immune response, e.g., at 1 to 4 months for a second dose, and if needed, a subsequent dose(s) after several months.

When mice were immunized (see Example 8) and subsequently challenged with live P. gingivalis in the subcutaneous (SC) chamber model for growth and invasion of P. gingivalis, there was significant protection against infection where the experimental animals were immunized with heat-killed whole cells of P. gingivalis, RGP-2, HMW RGP, and peptides derived from the catalytic domain or N-terminus of a 50 kDa Arg-gingipain or an adhesin domain of HMW RGP, with infection being measured by recovery of viable P. gingivalis from the SC chambers (See Example 8, Table 4).

All control (unimmunized) mice yielded viable bacteria during the course of infection. When mice were immunized with heat-killed P. gingivalis A7436 whole cells, HMW RGP, RGP-2 or Peptide A (N-terminal sequence of catalytic subunit of HMW RGP, SEQ ID NO:10), no viable bacteria were recovered at day 7. Partial protection was afforded by Peptide B, the catalytic domain peptide (SEQ ID NO:11) and by Peptide C, the hemagglutinin domain of HMW RGP (SEQ ID NO:12).

When protection was assessed by the survival or absence of lesions in the SC chamber model, Peptide B gave partial protection while the remaining treatments gave full protection (see Table 5 in Example 8).

Humans (or other mammals) immunized with Arg-gingipains or Lys-gingipains and/or peptides having amino acid sequences derived from a low molecular weight Arg-gingipain or a HMW RGP, are protected from infection and invasion by P. gingivalis as assessed in this animal model. Preferably the hemagglutinin domain is not contained in the immunogenic composition.

Figure 4:
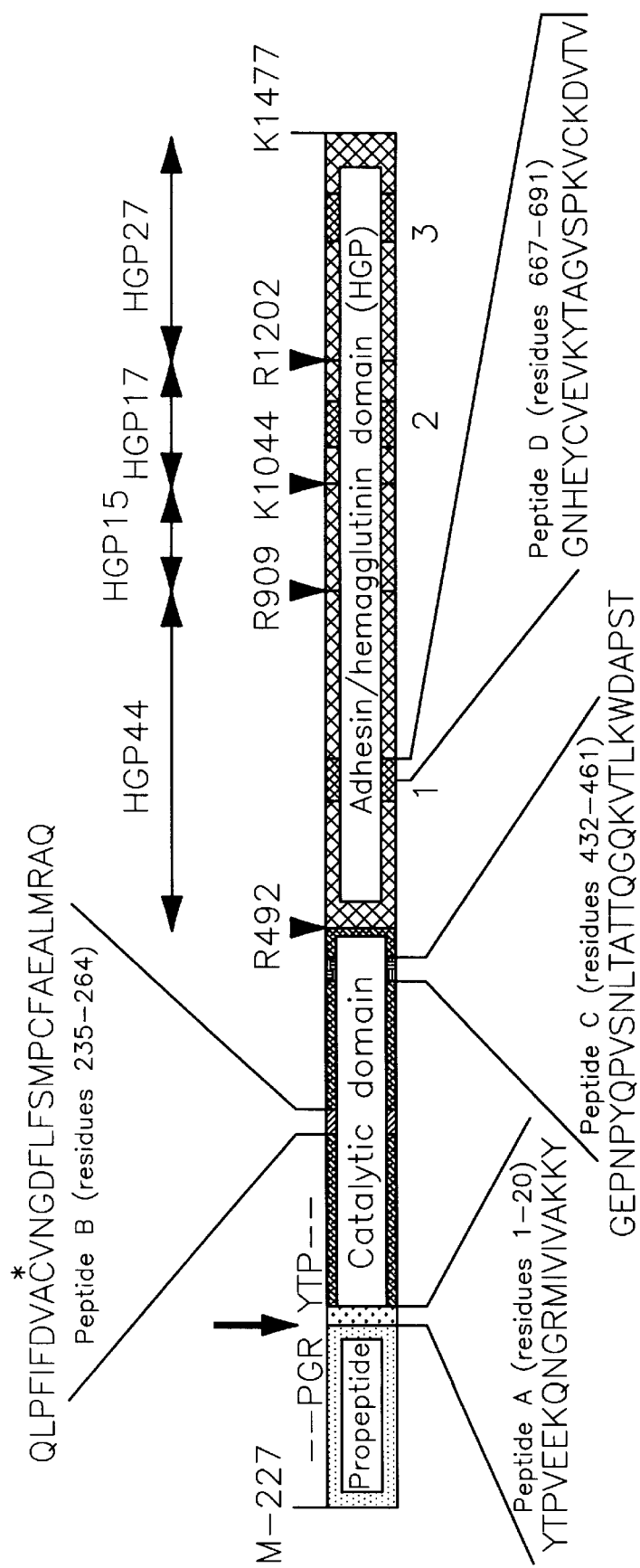
FIG. 4 diagrammatically illustrates the structure of pro-gingipain R1 (RGP-1), with indicated locations of peptides used for animal immunizations. The initial transcript of the rgp1 gene consists of propeptide, catalytic, and adhesin/hemagglutinin domains [Pavloff et al. (1995) *J. Biol. Chem.* 270:1007]. During translocation onto the *P. gingivalis* surface, the polyprotein undergoes proteolytic processing, resulting in the formation of mature RGP-1, either in membrane bound or soluble forms consisting of a non-covalent complex of a catalytic polypeptide and fragments of the adhesin/hemagglutinin domain [Pike et al. (1994) *J. Biol. Chem.* 269:406]. The adhesin/hemagglutinin domain is divided into subdomains (HGPs) of 44, 15, 17, and 27 kDa, according to proteolytic processing after one Lys and 3 Arg residues (arrowheads). The hemagglutination active site (Peptide D) is a part of a triplicate amino acid sequence repeat present in the HGP44, HGP17, and HGP27 subdomains. The triplicate repeats of 50 amino acid sequence within the adhesin/hemagglutinin domain are represented by hatched boxes numbered beneath the structure. RGP-2 is also translated as a proenzyme, nearly identical in sequence to the catalytic domain of RFP-1 but missing the entire adhesin/hemagglutinin domain. The structure of the Lys-gingipain polyprotein is similar to RGP-1, with the adhesin/hemagglutinin domain being virtually identical. The initial Lys-gingipain translation product is subject to posttranslational processing by Arg-gingipain(s) [Okamoto et al. (1996) *J. Biochem.* 120:398]. The catalytic domains of both gingipains share only limited identity (27%) scattered throughout the polypeptide chain, except for an identical 30 amino acid residue fragment (Peptide C). The cleavage of the propeptide which releases active RGPs is shown by an arrow. Arrowheads indicate putative proteolytic processing sites leading to assembly of the soluble or membrane-bound enzyme (95 kDa) in the form of a noncovalent complex of the catalytic domain with indicated, active fragments of the adhesin/hemagglutinin domain (HGP).

Female Balb/c mice were immunized with either RGP-1, RGP-2, or MAP-conjugated RGP-derived peptides by direct injection into stainless steel chambers implanted subcutaneously (Example 8), and subsequently challenged by injection of live P. gingivalis into chambers. Non-immunized animals or animals immunized with a scrambled peptide control and challenged with P. gingivalis developed ulcerated necrotic lesions on their abdomens, exhibited severe cachexia with ruffled hair, hunched bodies, and weight loss, with 14/22 and 5/8 deaths (Table 7). In contrast, animals immunized with MAP-conjugated Peptide A, corresponding to the N-terminus of the catalytic domain of RGPs (FIG. 4), followed by challenge with P. gingivalis were completely protected from abscess formation and death (Table 7). Similar results were obtained in animals that had been immunized with either whole P. gingivalis cells, RGP-1, or RGP-2. However, immunization with peptides corresponding to either a sequence encompassing the catalytic cysteine residue of RGPs (Peptide B) or an homologous sequence within the catalytic domains of RGPs and KGP (Peptide C), followed by challenge with P. gingivalis, did not protect animals, nor did a peptide corresponding to the binding site within the adhesin/hemagglutinin domain of RGP-1 (Peptide D) FIG. 4, Table 1, SEQ ID NO:14) which has been shown to be directly involved in the hemagglutinin activity of this gingipain [Curtiss et al. (1966) Infect. Immun. 64:2532]. Immunization with either peptide A, RGP-1, RGP-2, or P. gingivalis whole cells, followed by challenge with live bacteria resulted in a decrease in the number of mice from which this organism could be cultured (Table 8). In contrast, P. gingivalis was readily cultured from chamber fluid obtained from 20/22 non-immunized mice up to the time of death (Table 8) and from animals challenged after immunization with Peptides B, C, and D. In non-immunized animals P. gingivalis levels increased relative to the initial inoculum ($10^8$ to $10^{12}$ CFU) throughout the course of the experiments (Table 3), while in animals immunized with Peptide A, RGP-1, RGP-2, or whole cells, P. gingivalis decreased in numbers (from $10^8$ to $<10^6$). Taken together, these results indicate that immunization with a peptide corresponding to the N-terminal catalytic domain of RGPs can limit the ability of *P. gingivalis* to colonize and invade with the same efficiency as immunization with active proteinases or whole bacteria.

Immunization with the N-terminal peptide of Arg-gingipain induced a moderate IgG response to RGP-1 and RGP-2 (Table 9). The absence of a response to whole cells may be due to the lack of exposure of this epitope on cell surfaces so that the N-terminus of the membrane-associated RGP-1 catalytic domain is not available for antibody binding. The IgG response obtained following immunization with Peptide D, representing a portion of the adhesin/hemagglutinin domain of RGP-1, was comparable to that induced by the N-terminal peptide; however, protection against *P. gingivalis* challenge was not observed when this peptide was used as an immunogen (Tables 1 and 2). Immunization with RGP-1 induced a high IgG titer to all antigens examined except for RGP-2 (Table 9). The low titer to RGP-2 may be due to the absence of the highly immunogenic adhesin/hemagglutinin domain in this enzyme [Okamoto et al. (1996) *J. Biochem.* 120:398; Barkocy-Gallagher et al. (1996) *J. Bacteriol.* 178:2734]. Immunization with whole cells induced a good response to RGP-1 and KGP with essentially no binding to RGP-2. Postchallenge serum IgG titers were higher for all immunization groups when compared to the chamber fluid IgG titer 3 weeks postimmunization, reflecting the effect of challenge with *P. gingivalis*.

Figure 5:
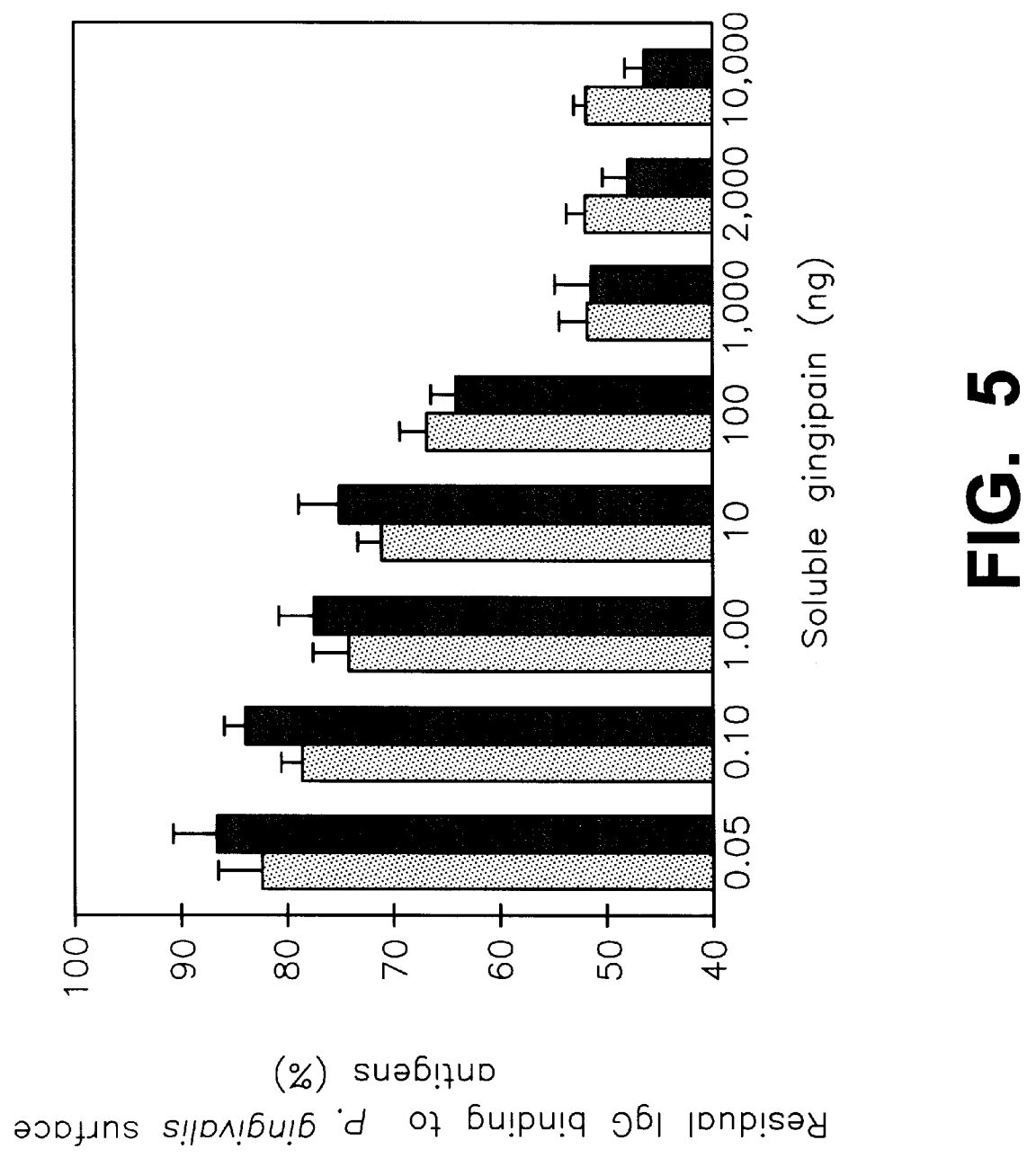

Competitive ELISA assays, using either RGP-1 or KGP as competing soluble antigens, indicated that 42% and 53% of the antibodies induced by immunization with heat-killed bacteria recognize RGP-1 and KGP, respectively (FIG. 5). However, even at very high concentrations, RGP-2 did not hinder IgG binding to *P. gingivalis*. These observations were also confirmed by Western blot analysis (FIG. 6D) and indicate that the non-catalytic hemagglutinin domains of RGP-1 and KGP are responsible for approximately 50% of the induced IgG response, and as such, constitute major antigens of *P. gingivalis*. Chamber fluid from mice immunized with the N-terminal peptide of the catalytic domain of RGPs reacted with the 50 kDa RGP-1, the catalytic domain of HMW RGP, with HMW RGP, with RGPs present in vesicles and bacterial membrane fractions, and with RGP-2 (FIG. 6A). A similar pattern was observed when chamber fluid from animals immunized with whole RGP-2 was utilized (FIG. 6E). The lack of reactivity with KGP is in agreement with antibody-specificity results (Table 2). Although the adhesin domain-derived peptide induced a poor IgG response as detected by ELISA, we found reactivity to several proteins by Western blot analysis (FIG. 6C). RGP-2 was not recognized by this antibody due to the lack of an adhesin domain. However, reactivity could be detected with the 27 kDa domains of RGP-1 and KGP and proteins migrating in the range of 60–70 kDa in vesicle and membrane preparations. Significantly, the adhesin domains present in the 44 kDa and 17 kDa subunits (FIG. 4) did not bind antibody.

Immunization with RGP-1 resulted in antibodies with specificity predominantly directed against the 44 kDa adhesin/hemagglutinin domain of RGP-1 and the 43 kDa domain of KGP (FIG. 6B). These domains were also recognized in vesicle and membrane preparations. Additional protein bands recognized by this antiserum included the 32 and 17 kDa proteins in KGP, as well as the equivalents in vesicles and membranes. However, the RGP-1 catalytic domain was only weakly recognized, and RGP-2 not at all. These results are in agreement with previous studies in which the catalytic domains of RGPs were poorly recognized in antisera obtained from rabbits or chickens immunized with the entire RGP-1 molecule. Immunization with heat-killed bacteria results in antibodies (FIG. 6D) with specificities astonishingly similar to those induced by immunization with RGP-1. In addition to polypeptides composing the RGP-1 complex, high molecular weight proteins were also detected in vesicles and membranes. No reactivity was detected (Western blot analysis) for the catalytic domain of RGP-1 or RGP-2, results in agreement with those obtained with mice immunized with RGP-1 (FIG. 6B) and consistent with data obtained by ELISA in which antibodies generated following immunization with heat-killed *P. gingivalis* exhibited a very low titer against RGP-2.

This study indicates that in mice the major IgG response is targeted to the adhesin/hemagglutinin domain of RGP-1. This is consistent with analysis of sera from patients with severe, untreated periodontitis. Such a specific response to the adhesin/hemagglutinin domain of gingipains mounted in human periodontitis patients appears to divert the immune response away from other protective antigens. In the mouse model, antibodies with this specificity can limit colonization and invasion of *P. gingivalis*. However, in human subjects where the local inflammatory response leads to bone loss and destruction of the periodontal ligament, such antibodies can aggravate local tissue damage within the periodontal ligament. In this study, immunization of mice with a peptide corresponding to the N-terminus of RGPs generated a protective antibody response, but those antibodies did not recognize either RGP-1 or RGP-2 in cell preparations, indicating that this epitope (FIG. 4) is not exposed in whole cells. Rabbit antisera generated to the N-terminal portion of the catalytic domain of RGP-1 and RGP-2 also did not recognize RGP-1 in membranes or vesicle preparations unless samples were denatured by boiling, again suggesting that this epitope is not exposed in whole cells or vesicles. Inhibition of the maturation and/or catalytic activity of RGPs can inhibit invasion and colonization of *P. gingivalis* in mice and man. Such enzymes contribute to virulence in a multifactorial manner by influencing adherence to host tissues, activating cascade systems, degrading host proteins, and disturbing host defenses. RGPs can act as processing proteinases responsible for self maturation and the maturation of KGP, fimbrillin, and a 75 kDa major cell surface protein. These latter proteins are required for full virulence of *P. gingivalis* [Malek et al. (1994) *J. Bacteriol.* 176:1052; Goulbourne and Ellen (1991) *J. Bacteriol.* 173:5266; Lamont et al. (1994) *Oral Microbiol. Immunol.* 8:272; Lamont et al. (1992) *Oral Microbiol. Immunol.* 7:1993; Hamada et al. (1994) *Infect. Immun.* 62:1696; Tokuda et al. (1996) *Infect. Immun.* 64:4067].

Except as noted hereafter, standard techniques for peptide synthesis, cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Ausubel et al. (1994) *Current Protocols in Molecular Biology*, Green Publishing, Inc., Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) Meth. Enzymol. 218, Part I; Wu (ed.) (1979) Meth Enzymol. 68; Wu et al. (eds.) (1983) *Meth. Enzymol.* 100 and 101; Grossman and Moldave (eds.) 1980 *Meth. Enzymol.* 65; Miller (ed.) (1972) *Experiments in Molecular Genetics*, Cold spring Harbor Laboratory, Cold Spring Harbor, N.Y., Old Primrose (1981) *Principles of Gene Manipulation,* University of California Press, Berkeley; Schleif and Wensink (1981) *Practical Methods in Molecular Biology;* Glover (ed.) (1985) *DNA Cloning* Vol. I and II, IRL Press, Oxford, UK; Hames and Higgins (eds.) (1985) *Nucleic Acid Hybridisation,* IRL Press, Oxford, UK; Setlow and Hollaender (1979) *Genetic Engineering: Principles and Methods,* Vols. 1–4, Plenum Press, New York. Abbreviations and nomenclature, where employed, are deemed standard in the field and commonly used in professional journals such as those cited herein. All references cited in this application are incorporated by reference in their entirety.

The foregoing discussion and the following examples illustrate but are not intended to limit the invention. The skilled artisan will understand that alternative methods can be used to implement the invention.

EXAMPLE 1

Purification of Arg-Gingipains and Lys-Gingipains
Bacterial Cultivation

*P. gingivalis* strains HG66 (W83) and W50 (virulent) were used in these studies. Cells were grown in 500 ml of broth containing 15.0 g Trypticase Soy Broth (Difco, Detroit, Mich.), 2.5 g yeast extract, 2.5 mg hemin, 0.25 g cysteine, 0.05 g dithiothreitol, 0.5 mg menadione (all from Sigma Chemical Company, St. Louis, Mo.) anaerobically at 37° C. for 48 hr in an atmosphere of 85% $N_2$, 10% $CO_2$, 5% $H_2$. The entire 500 ml culture was used to inoculate 20 liters of the same medium, and the latter was incubated in a fermentation tank at 37° C. for 48 hr (to a final optical density of 1.8 at 650 nm). RGP-1 can also be purified as described for RGP-2.
Proteinase Purification (RGP-1)

1200 ml cell-free supernatant was obtained from the 48 hr culture by centrifugation at 18,000×g for 30 min. at 4° C. Proteins in the supernatant were precipitated out by 90% saturation with ammonium sulfate. After 2 hr at 4° C., the suspension was centrifuged at 18,000×g for 30 min. The resulting pellet was dissolved in 0.05 M sodium acetate buffer, pH 4.5, 0.15 NaCl, 5 mM $CaCl_2$; the solution was dialyzed against the same buffer overnight at 4° C., with three changes with a buffer:protein solution larger than 150:1. The dialysate was then centrifuged at 25,000×g for 30 min and the dark brown supernatant (26 ml) was then chromatographed over an agarose gel filtration column (5.0×150 cm; Sephadex G-150, Pharmacia, Piscataway, N.J.) which had been pre-equilibrated with the same buffer. The column was developed with said buffer at a flow rate of 36 ml/hr. 6 ml fractions were collected and assayed for both amidolytic and proteolytic activities, using Bz-L-Arg-pNA and azocasein as substrates. Four peaks containing amidolytic activity were identified. The fractions corresponding to peak 4 were combined, concentrated by ultrafiltration (Amicon PM-10 membrane; Amicon, Beverly, Mass.) and then dialyzed overnight against 0.05 Bis-Tris, 5 mM $CaCl_2$, pH 6.0. The volume of the dialysate was 14 ml.

The 14 ml dialysate from the previous step was then applied to a DEAE-cellulose (Whatman, Maidstone, England) column (1×10 cm) equilibrated with 0.05 mM Bis-Tris, 5 mM $CaCl_2$, pH 6.0. The column was then washed with an additional 100 ml of the same buffer. About 75% of the amidolytic activity, but only about 50% of the protein, passed through the column. The column wash fluid was dialyzed against 0.05 M sodium acetate buffer containing 5 mM $CaCl_2$ (pH 4.5). This 19 ml dialysate was applied to a Mono S FPLC column (Pharmacia LKB Biotechnology Inc., Piscataway, N.J.) equilibrated with the same buffer. The column was washed with the starting buffer at a flow rate of 1.0 ml/min for 20 min. Bound proteins were eluted first with a linear NaCl gradient (0 to 0.1 M) followed by a second linear NaCl gradient (0.1 to 0.25 M), each gradient applied over a 25 min time period. Fractions were assayed for amidolytic activity using Bz-L-Arg-pNA. Fractions with activity were pooled and re-chromatographed using the same conditions. Although not detectable by gel electrophoresis, trace contamination by a proteinase capable of cleaving after lysyl residues was sometimes observed. This contaminating activity was readily removed by applying the sample to an arginine-agarose affinity column (L-Arginine-SEPHAROSE 4B) equilibrated with 0.025 M Tris-HCl, 5 mM $CaCl_2$, 0.15 M NaCl, pH 7.5. After washing with the same buffer, purified enzyme was eluted with 0.05 M sodium acetate buffer, 5 mM $CaCl_2$, pH 4.5. Yields of gingipain-1 were markedly reduced by this step (about 60%).

RGP-1 can also be purified as described for RGP-2 with such appropriate modifications as are readily apparent to one of ordinary skill in the art.
Proteinase Purification (HMW RGP)

The culture supernatant (2,900 ml) was obtained by centrifugation of the whole culture (6,000×g, 30 min, 4° C.). Chilled acetone (4,350 ml) was added to this fraction over a period of 15 min, with the temperature of the solution maintained below 0° C. at all times, using an ice/salt bath and this mixture was centrifuged (6,000×g, 30 min, −15° C.). The precipitate was dissolved in 290 ml of 20 mM Bis-Tris-HCl, 150 mM NaCl, 5 mM $CaCl_2$, 0.02% (w/v) $NaN_3$, pH 6.8 (Buffer A), and dialyzed against Buffer A containing 1.5 mM 4,4'-Dithiodipyridine disulfide for 4 h, followed by 2 changes of buffer A overnight. The dialyzed fraction was centrifuged (27,000×g, 30 min, 4° C.), following which it was concentrated to 40 ml by ultrafiltration using an Amicon PM-10 membrane. This concentrated fraction was applied to a Sephadex G-150 column (5×115 cm=2260 ml; Pharmacia, Piscataway, N.J.) which had previously been equilibrated with Buffer A, and the fractionation was carried out at 30 ml/h (1.5 cm/h). Fractions (9 ml) were assayed for activity against Bz-L-Arg-pNa and Z-L-Lys-pNa (Novabiochem; 0.5 mM). Amidolytic activities for Bz-L-Arg-pNa (0.5 mM) or Z-L-Lys-pNa were measured in 0.2 M Tris.Hcl, 1 mM $CaCl_2$, 0.02% (w/v) $NaN_3$, 10 mM L-cysteine, pH 7.6. General proteolytic activity was measured with azocasein (2% w/v) as described by Barrett and Kirschke (1981) *Meth. Enzymol.* 80:535–561 for cathepsin L. Three peaks with activity against the two substrates were found. The first (highest molecular weight) peak of activity was pooled, concentrated to 60 ml using ultrafiltration and dialyzed overnight against two changes of 50 mM Tris-HCl, 1 mM $CaCl_2$, 0.02% $NaN_3$, pH 7.4 (Buffer B).

This high MW fraction was applied to an L-Arginine-Sepharose column (1.5×30 cm=50 ml), which had previously been equilibrated with Buffer B at a flow rate of 20 ml/hr (11.3 cm/h), following which the column was washed with two column volumes of Buffer B. Following this, a step gradient of 500 mM NaCl was applied in Buffer B and the column was washed with this concentration of NaCl until the $A_{280}$ baseline fell to zero. After re-equilibration of the column in Buffer B, a gradient from 0–750 mM L-Lysine was applied in a total volume of 300 ml, followed by 100 ml of 750 mM L-Lysine. The column was once again re-equilibrated with Buffer B and a further gradient to 100 mM L-arginine in 300 ml was applied in the same way. Fractions (6 ml) from the Arg wash were assayed for activity against the two substrates as described previously. The arginine gradient eluted a major peak for an enzyme degrading Bz-L-Arg-pNa. The active fractions were pooled and dialyzed against two changes of 20 mM Bis-Tris-HCl, 1 mM CaCl$_2$, 0.02% (v/w) NaN$_3$, pH 6.4 (Buffer C) and concentrated down to 10 ml using an Amicon PM-10 membrane.

The concentrate with activity for cleaving Bz-L-Arg-pNa was applied to a Mono Q FPLC column (Pharmacia LKB Biotechnology Inc, Piscataway, N.J.) equilibrated in Buffer C, the column was washed with 5 column volumes of Buffer C at 1.0 ml/min, following which bound protein was eluted with a 3 step gradient [0–200 mM NaCl (10 min), followed by 200–250 mM NaCl (15 min) and 250–500 mM NaCl (5 min)]. The active fractions from Mono Q were pooled and used for further analyses.

RGP-2 Purification

Cells of *P. gingivalis* (H66) were grown in 200 ml of broth containing 6.0 g of Trypticase Soy broth (Difco), 2.0 g of yeast extract, 1 mg of hemin, 200 mg of cysteine, 20 mg dithiothreitol and 0.5 mg of menadione (all from Sigma Chemical Co., St. Louis, Mo.) anaerobically, at 37° C. for 48 h in an atmosphere of 85% N2, 10% CO2, 5% H2. The culture was used to inoculate 5 liters of the same broth, and incubated anaerobically, at 37° C. for about 48–60 h until the late stationary phase of bacteria growth (final optical density>2.0).

For purification of RGP-2, the initial steps of purification were performed according to the method design for 94 kDa HMW RGP and high molecular weight lysine-specific gingipain (KGP) purification [Pike et al. (1994) *J. Biol. Chem.* 269:406–411]. Briefly, the cell-free culture fluid was obtained by centrifugation of the whole culture and chilled to −20° C. Acetone was slowly added to the chilled culture supernatant, with the temperature being maintained below 0° C. The precipitated protein was collected by centrifugation, and the pellet was dissolved in 20 mM Bis-Tris, 150 mM NaCl, 0.02% NaN3 buffer (pH 6.8) containing 1.5 mM 4,4'-dithiodipyridine disulfide (in a total volume equal to ½0 of original culture supernatant subjected precipitation) and dialyzed first against the above buffer (one change) followed by two changes of the Bis-Tris/NaCl buffer supplemented with 5 mM CaCl2 but lacking 4,4'-dithiodipyridine disulfide. The dialyzed protein solution was clarified by high speed centrifugation (40,000×g, 2 h), concentrated by ultrafiltration using an Amicon PM-10 membrane (Amicon, Danvers, Mass.), and the clarified solution was then applied to a gel filtration column (Sephadex G-150, Pharmacia, Piscataway N.J.) equilibrated with Bis-Tris buffer. The column was developed at a flow rate of 30 ml/h, and three peaks with activity against Bz-L-Arg-pNA and Z-L-Lys-pNA were found. The highest molecular mass peak of activity against Bz-L-Arg-pNA/Z-L-Lys-pNA was used for the purification of 95 kDa HMW RGP exactly as described by Pike et al. (1994) supra, while the lowest molecular mass peak having the majority of the activity against Bz-L-Arg-pNA was pooled, concentrated by ultrafiltration, and extensively dialyzed against several changes of 50 mM Bis-Tris, 1 mM CaCl2, pH 6.5 and loaded at a flow rate 20 ml/h on anion exchange resin DE-52 Cellulose (Whatman) column (1.5×20 cm) equilibrated with Bis-Tris/CaCl2 buffer. This column was washed until the A$_{280nm}$ base line fell to zero; then a gradient of 0–200 mM NaCl was applied in a total volume of 250 ml. Fractions (4 ml each) were assayed for activity against Bz-L-Arg-pNA. Some of this activity was found in the void volume (Vo) of the column, but the major peak was eluted at 100 mM NaCl concentration. Fractions from both peaks of activity were pooled, concentrated and dialyzed extensively either versus 50 mM sodium acetate buffer, 5 mM CaCl2, pH 4.5 (Vo) or against 50 mM Tris, 1 mM CaCl2, pH 7.4 with 0.02% NaN3 (NaCl elute).

From the Vo (run-through) of the DE-52 column, RGP-1 was purified by means of HPLC on a Mono S column, followed by affinity chromatography over arginine-Sepharose 4B as described previously [Chen et al. (1991) supra]. The major activity peak eluted from DE-52 cellulose column with NaCl was applied to the arginine-Sepharose column (1.5×30 cm, 50 ml) equilibrated with Tris/CaCl$_2$ buffer pH 7.4 at the flow rate of 20 ml/h, following which the column was washed with buffer until activity against Bz-L-Arg-pNA fell below 20 mOD/min/ml, then a gradient to 100 mM L-arginine was applied in a volume of 300 ml. Three distinct peaks of activity obtained in this step, nonadsorbed, retarded and eluted with L-arginine, were concentrated, dialyzed against 3 changes of 50 mM sodium acetate buffer, 1 mM CaCl$_2$, pH 4.5 and applied to a Mono S FPLC column equilibrated with the same buffer at a flow rate of 1 ml/min. The column was washed with starting buffer and bound protein eluted using a linear NaCl gradient (0–0.15 M NaCl over 30 min time period). Fractions in peaks containing activity were combined, dialyzed against 20 mM Bis-Tris, 150 mM NaCl, 5 mM CaCl$_2$, pH 6.8 with NaN$_3$ and used for further analysis.

Purification of Lys-Gingipain

*P. gingivalis* strain HG66 (W83) was obtained from Roland Arnold (Emory University, Atlanta, Ga.). Cells were grown in 500 ml of broth containing 15.0 g Trypticase Soy Broth (Difco, Detroit, Mich.), 2.5 g yeast extract, 2.5 mg hemin, 0.25 g cysteine, 0.05 g dithiothreitol, 0.5 mg menadione (all from Sigma Chemical Company, St. Louis, Mo.) anaerobically at 37° C. for 48 hr in an atmosphere of 85% N$_2$, 10% CO$_2$, 5% H$_2$. The entire 500 ml culture was used to inoculate 20 liters of the same medium, and the latter was incubated in a fermentation tank at 37° C. for 48 hr (to a final optical density of 1.8 at 650 nm).

The culture supernatant (2,900 ml) was obtained by centrifugation of the whole culture (6,000×g, 30 min, 4° C.). Chilled acetone (4,350 ml) was added to this fraction over a period of 15 min, with the temperature of the solution maintained below 0° C. at all times, using an ice/salt bath to precipitate proteins. This mixture was centrifuged (6,000×g, 30 min, −15° C.). The precipitate was dissolved in 290 ml of 20 mM Bis-Tris-HCl, 150 mM NaCl, 5 mM CaCl$_2$, 0.02% (w/v) NaN$_3$, pH 6.8 (Buffer A), and dialyzed against Buffer A containing 1.5 mM 4,4'-Dithiodipyridine disulfide for 4 h, followed by 2 changes of Buffer A overnight. The dialyzed fraction was centrifuged (27,000×g, 30 min, 4° C.), following which the supernatant was concentrated to 40 ml by ultrafiltration using an Amicon PM-10 membrane. This concentrated fraction was applied to a Sephadex G-150 column (5×115 cm=2260 ml; Pharmacia, Piscataway, N.J.) which had previously been equilibrated with Buffer A, and the fractionation was carried out at 30 ml/h (1.5 cm/h). Fractions (9 ml) were assayed for activity against Bz-L-Arg-pNa and Z-L-Lys-pNa (Novabiochem; 0.5 mM). Amidolytic activities for Bz-L-Arg-pNa (0.5 mM) or Z-L-Lys-pNa were measured in 0.2 M Tris-HCl, 1 mM CaCl$_2$, 0.02% (w/v) NaN$_3$, 10 mM L-cysteine, pH 7.6. Three peaks with activity against both pNA substrates were found. The highest molecular weight peak of activity contained most of the Z-L-Lys-pNA amidolytic activity. The fractions of the highest molecular weight peak of activity were pooled, concentrated to 60 ml using ultrafiltration and dialyzed overnight against two changes of 50 mM Tris-HCl, 1 mM CaCl$_2$, 0.02% NaN$_3$, pH 7.4 (Buffer B).

This high MW fraction concentrate was applied to an L-Arginine-Sepharose column (1.5×30 cm=50 ml), which had previously been equilibrated with Buffer B at a flow rate of 20 ml/hr (11.3 cm/h), following which the column was washed with two column volumes of Buffer B. Following this, a step gradient of 500 mM NaCl was applied in Buffer B and the column was washed with this concentration of NaCl until the $A_{280}$ baseline fell to zero. After re-equilibration of the column with Buffer B, a linear gradient from 0–750 mM L-Lysine in Buffer B was applied in a total volume of 300 ml, followed by 100 ml of Buffer B containing 750 mM L-Lysine. The column was once again re-equilibrated with Buffer B and a further gradient to 100 mM L-arginine in 300 ml was applied in the same way. Fractions (6 ml) from the Lys wash and from the Arg wash were assayed for activity against the two pNA substrates as described previously. The lysine gradient eluted a major peak of activity against Z-L-Lys-pNa only and the arginine gradient did the same for an enzyme degrading Bz-L-Arg-pNa. The active (for Z-L-Lys-pNA) fractions were pooled and dialyzed against two changes of 20 mM Bis-Tris-HCl, 1 mM $CaCl_2$, 0.02% (w/v) $NaN_3$, pH 6.4 (Buffer C) and the dialyzate was concentrated to 10 ml using Amicon PM-10 membranes.

The dialyzate was applied to an anion exchange FPLC column (Mono Q FPLC column, Pharmacia LKB Biotechnology Inc., Piscataway, N.J.) equilibrated in Buffer C, the column was washed with 5 column volumes of Buffer C at a flow rate of 1.0 ml/min, following which bound protein was eluted with a 3 step gradient [0–200 mM NaCl (10 min), followed by 200–275 mM NaCl (15 min) and 275–500 mM NaCl (5 min), each in Buffer C. The active fractions from Mono Q chromatography were pooled.

EXAMPLE 2

Molecular Weight Determination

The molecular weights of the purified Arg-gingipains and Lys-gingipains were estimated by gel filtration on a Superose 12 column (Pharmacia, Piscataway, N.J.) and by Tricine-SDS polyacrylamide gel electrophoresis. In the latter case, 1 mM TLCK was used to inactivate the protease prior to boiling, thus preventing autoproteolytic digestion.

EXAMPLE 3

Enzyme Assays

Amidolytic activities of *P. gingivalis* proteinases were measured with the substrates MeO-Suc-Ala-Ala-Pro-Val-pNA at a concentration of 0.5 mM, Suc-Ala-Ala-Ala-pNA (0.5 mM), Suc-Ala-Ala-Pro-Phe-pNA (0.5 mM), Bz-Arg-pNA (1.0 mM), Cbz-Phe-Leu-Glu-pNA) (0.2 mM); S-2238, S-2222, S-2288 and S-2251 each at a concentration of 0.05 mM; in 1.0 ml of 0.2 M Tris-HCl, 5 mM $CaCl_2$, pH 7.5. In some cases either 5 mM cysteine and/or 50 mM glycylglycine (Gly-Gly) was also added to the reaction mixture. Z-L-Lys-pNa (0.5 mM) in 0.2 M Tris-HCl, 0.02% (w/v) $NaN_3$, 10 mM L-cysteine, was used for assay oaf Lys-gingipain.

General proteolytic activity was assayed using the same buffer system as described for detecting amidolytic activity, but using azocoll or azocasein (2% w/v) as substrate as described for Cathepsin L by Barrett and Kirschke (1981), *Meth. Enzymol.* 80, 535–561.

For routine assays, pH optimum determination and measurement of the effect of stimulating agents and inhibitors on Arg-gingipains, only Bz-L-Arg-pNA was used as substrate. Potential inhibitory or stimulatory compounds were preincubated with enzyme for up to 20 min at room temperature at pH 7.5, in the presence of 5 mM $CaCl_2$ (except when testing the effects of chelating agents) prior to the assay for enzyme activity.

General proteolytic activity was assayed using the same buffer system as described for detecting amidolytic activity, but using azocoll or azocasein (1% w/v) as substrate.

A unit of RGP enzymatic activity is based on the spectroscopic assay using benzoyl-Arg-p-nitroanilide as substrate and recording $\Delta$ absorbance units at 405 nm/min/absorbance unit at 280 nm according to the method of Chen et al. (1992) supra.

EXAMPLE 4

Amino Acid Sequence Analysis

Amino-terminal amino acid sequence analyses were carried out using an Applied Biosystems 4760A gas-phase sequenator, using the program designed by the manufacturer. Alternatively, amino acid sequences were deduced from the coding sequences of the corresponding coding sequences (see SEQ ID NO:1 and SEQ ID NO:3). The amino acid sequences of the COOH terminus of SDS-denatured RGP-1 and of the 50 kDa subunit of HMW RGP were determined. 10 nmol aliquots of gingipain-1 were digested in 0.2 M N-ethylmorpholine acetate buffer, pH 8.0, with carboxypeptidase A and B at room temperature, using 1:100 and 1:50 molar ratios, respectively. Samples were removed at intervals spanning 0 to 12 hours, boiled to inactivate the carboxypeptidase, and protein was precipitated with 20% trichloracetic acid. Amino acid analyses were performed on the supernatants.

EXAMPLE 5

Materials

MeO-Suc-Ala-Ala-Pro-Val-pNA, Suc-Ala-Ala-Pro-Phe-pNA, Gly-Pro-pNA, Suc-Ala-Ala-Ala-pNA, Bz-Arg-pNA, diisopropylfluorophosphate, phenylmethylsulfonyl fluoride, tosyl-L-lysine chloromethyl ketone (TLCK), tosyl-L-phenylalanine chloromethyl ketone (TPCK), trans-epoxysuccinyl-L-leucylamide-(4-guanidino)butane), an inhibitor of cysteine proteinases, leupeptin, antipain and azocasein were obtained from Sigma Chemical Co., St. Louis, Mo. 3,4-Dichloroisocoumarin was obtained from Boehringer, Indianapolis, Ind. and CBz-Phe-Leu-Glu-pNA and azocoll were obtained from Calbiochem, La Jolla, Calif. S-2238 (D-Phe-Pip-Arg-pNA), S-2222 (Bz-Ile-Glu-($\gamma$-OR)-Gly-Arg-pNA), S-2288 (D-Ile-Pro-Arg-pNA), and S-2251 (D-Val-Leu-Lys-pNA) were from Kabi-Vitrum, (Beaumont, Tex.).

EXAMPLE 6

Electrophoresis

SDS-PAGE was performed as in Laemmli (1970) *Nature* 227:680–685. Prior to electrophoresis the samples were boiled in a buffer containing 20% glycerol, 4% SDS, and 0.1% bromophenol blue. The samples were run under reducing conditions by adding 2% $\beta$-mercaptoethanol unless otherwise noted. Samples were heated for 5 min at 100° C. prior to loading onto gels. A 5–15% gradient gel was used for the initial digests of C3 and C5, and the gels were subsequently stained with Coomassie Brilliant Blue R. The C5 digest used to visualize breakdown products before and after reduction of the disulfide bonds were electrophoresed in a 8% gel. Attempts to visualize C5a in the C5 digest were carried out using 13% gels that were developed with silver stain according to the method of Merril et al. (1979) *Proc. Natl. Acad. Sci USA* 76:4335–4339. In some experiments (with HMW RGP) SDS-PAGE using Tris-HCl/Tricine buffer was carried out per Shagger and Van Jagow (1987) *Analyt. Biochem.* 166:368–379.

EXAMPLE 7

Coding Sequences for Arg-gingipains and Lys-gingipains

λDASH DNA libraries were constructed according to the protocols of Stratagene, using the lambda DASH™ II/BamHI cloning kit and DNA preparations from *P. gingivalis* strains HG66 (W83) and W50. A library of $3 \times 10^5$ independent recombinant clones was obtained using *P. gingivalis* H66 DNA, and $1.5 \times 10^5$ independent recombinant clones were obtained from virulent *P. gingivalis* W50 DNA. The coding and amino acid sequences of the polyprotein precursor of the HMW RGP is given in SEQ ID NO:5. SEQ ID NO:7 provides the Lys-gingipain coding sequence and SEQ ID NO:8 the amino acid sequence.

EXAMPLE 8

Animal Model Studies

A mouse animal model [described in Genco et al. (1991) *Infect. Immun.* 59:1255–1263] was used to study the protective effects of immunogenic compositions comprising *P. gingivalis* proteinases and/or peptides derived therefrom.

Peptides for use as immunogens were synthesized using an Applied Biosystems automated solid state process and the multi-lysine base according to the method of Tam, J. P. (1988) *Proc. Natl. Acad. Sci. USA* 85:5409–5413 and Posnett et al. (1988) *J. Biol. Chem.* 263:1719–1725. After purification, the peptides were suspended as described below. The multiple lysine base provides a framework for the simultaneous synthesis of multiple identical peptides and results in an "octopus"-like molecule which is antigenic without the need for conjugation to a carrier peptide. The multiple lysine base is not itself antigenic. Thus, this technique offers some advantages over the previous peptide immunizations which required conjugation to carrier proteins such as keyhole limpet hemocyanin and bovine serum albumin. RGP-related peptide sequences used in these experiments are provided below.

Whole cell antigens for immunization were prepared by centrifugation of *P. gingivalis* cultures for 10 min at 10,000×g at room temperature and resuspension in ⅒ the original volume of anaerobic broth. Bacterial cells were heated to 95° C. for 10 min, and heat-treated preparations were plated on anaerobic blood agar and incubated for 7 days under anaerobic conditions to confirm effective killing. RGPs were purified from strain HG66 as described hereinabove.

Mice were immunized by injection of each immunogen (50 µg/mouse in Freund's complete adjuvant) in subcutaneous chambers implanted in mice [Genco et al. (1992) *Infect. Immun.* 60:1447]. Animals immunized with heat-killed *P. gingivalis* received an initial immunization corresponding to $10^8$ CFU. Control mice were immunized with Freund's adjuvant only.

Female BALB/c mice about 8 weeks old are obtained from Sasco (Omaha, Nebr.) or Charles River Laboratory (Wilmington, Mass.). Coil-shaped subcutaneous (SC) chambers were prepared from 0.5 mm stainless steel wire and surgically implanted in the SC tissue of the dorsolumbar region of each mouse, with anaesthesia. A recovery period of at least 10 days is allowed before further treatment. During the 10 day period, the outer incision heals completely and the chambers become encapsulated by a thin vascularized layer of fibrous connective tissue and gradually filled with approximately 0.5 ml of light-colored transudate.

After the 10 day recovery period, the mice are immunized according to the scheme in Table 1:

TABLE 1

| Group | Immunogen | Number of Mice |
|-------|-----------|----------------|
| A | None | 6 |
| B | 50 kDa RGP-2 | 6 |
| C | Peptide B | 8 |
| D | Peptide C | 8 |
| E | Peptide A | 8 |
| F | 95 kDa HMW RGP | 8 |
| G | Heat-killed *P. gingivalis* A7436 whole cells | 8 |

Stock solutions of immunogens were as follows: RGP-2, 1.65 mg/ml in 20 mM Bis-Tris, 150 mM NaCl, 5 mM $CaCl_2$, 0.02% $NaN_3$, pH 6.8 and diluted to 1 mg/ml for use in immunizations; Peptide B (SEQ ID NO:11, QLPFIFDVACVNGDFLFSMPCFAEALMRAQ, catalytic domain of HMW RGP), 1 mg/ml in cold $NH_4HCO_3$ made fresh; Peptide C (SEQ ID NO:12, GEPNPYQPVSNLTATTQGQKVTLKWDAPSTK, hemagglutinin domain of HMW RGP) 1 mg/ml in 10 mM acetic acid; Peptide A (SEQ ID NO:10, YTPVEEKQNGRMIVIVAKKY, N-terminus of the HMW RGP catalytic subunit, 1 mg/ml in 10 mM acetic acid; RGP-2, 0.96 mg/ml in 20 mM Bis-Tris, 150 mM NaCl, 5 mM $CaCl_2$, 0.02% $NaN_3$, pH 6.8; and heat-killed whole *P. gingivalis* A7436 bacterial cells, $10^9$/ml. Group A mice (unimmunized controls) were inoculated with only Freund's complete adjuvant. Groups B–F were immunized with 50 µg of MAP-peptides or protein in Freund's complete adjuvant per mouse in the primary immunizations injected into the chambers or SC. Groups B–F mice were given booster immunizations of 50 µg MAP-peptide twice a week for 5 weeks in Freund's incomplete adjuvant. Group G mice were immunized by injecting the heat-killed whole bacterial cells into the chambers (without adjuvant). $10^8$ cells were injected into the chambers directly in the primary immunization; $10^2$ cells were injected in all booster immunizations.

Mice are challenged with live *P. gingivalis* A7436 ($2 \times 10^{10}$ colony forming units) five weeks after the initial immunization. The mice are observed daily for general appearance, primary and/or secondary abscess formation and health status. Chamber fluid is removed daily with a hypodermic needle and syringe for bacteriologic culture and microscopic examination. Fluid is also examined for the presence and activity of antibodies to the respective peptides. All surviving animals are sacrificed 30 days after inoculation, and the sera are separated from blood obtained by cardiac puncture.

During the 10 day period the outer incision heals completely and the chambers become encapsulated by a thin vascularized layer of fibrous connective tissue and gradually filled with approximately 0.5 ml of light-colored transudate. Ten days after implantation, chambers are inoculated with 0.1 ml of a suspension of *P. gingivalis* cells in prereduced Anaerobic Broth MIC (Difco Laboratories, Detroit, Mich.). Control SC chambers were injected with Schaedler broth lacking bacterial cells. Mice were examined daily for size and consistency of primary or secondary lesions and for general appearance, primary and/or secondary abscess formation and health status. Severe cachexia is characterized by ruffled hair, hunched bodies and weight loss. Chamber fluid is aseptically removed from each implanted chamber with a 25 gauge hypodermic needle and syringe at 1 to 7, and 14 days after inoculation for bacteriological culture and microscopic examination. All surviving animals are sacrificed at 30 days postinoculation and serum is separated from blood obtained by cardiac puncture.

Aliquots of chamber fluid are streaked after live bacterial challenge for isolated microbial colonies on anaerobic blood agar plates (Remel, Lenexa, Kans.) and incubated for 7 days at 37° C. under anaerobic conditions. *P. gingivalis* is then identified by standard techniques as described in Holdeman et al. (1984) "Anaerobic gram-negative straight, curved and helical rods. Family 1. Bacteroidaceae, Pribram," In N. R. Krieg and J. G. Holt (ed.) *Bergey's Manual of Determinative Bacteriology*, The Williams & Wilkins Co., Baltimore, Md., p. 602–631. Cultivable bacterial counts are obtained by serially diluting chamber fluid in Schaedler broth and spin plating onto anaerobic blood agar plates.

Table 2 provides the results for recovery of *P. gingivalis* from the SC chambers at various times after challenges.

TABLE 2

*P. gingivalis* cultured from chamber fluid

% of mouse SC chambers from which *P. gingivalis* was cultured on given day postinoculation and CFU obtained from chambers

| Group | 1 | 2 | 4 | 7 |
|---|---|---|---|---|
| A | 83% | 66% | 83% | 100% |
|   | $(1.8 \times 10^{12})$ | $(1.6 \times 10^{12})$ | $(1.1 \times 10^{12})$ | $(7.2 \times 10^{12})$ |
| B | 33% | 16% | 16% | 0% |
|   | $(7.6 \times 10^{11})$ | $(4.7 \times 10^{11})$ | $(1.5 \times 10^{10})$ |   |
| C | 38% | 38% | 25% | 29% |
|   | $(8.4 \times 10^{11})$ | $(1.4 \times 10^{12})$ | $(1.1 \times 10^{10})$ | $(1.9 \times 10^{11})$ |
| D | 63% | 75% | 50% | 63% |
|   | $(7.3 \times 10^{11})$ | $(1.7 \times 10^{11})$ | $(6.8 \times 10^{10})$ | $(2.2 \times 10^{11})$ |
| E | 38% | 50% | 25% | 0 |
|   | $(1.4 \times 10^{10})$ | $(4.7 \times 10^{9})$ | $(4.0 \times 10^{8})$ | (ND) |
| F | 38% | 25% | 13% | 0 |
|   | (ND) | (ND) | (ND) | (ND) |
| G | 13% | 0 | 0 | 0 |
|   | (ND) | (ND) | (ND) | (ND) |

* ND means not detectable

Table 3 summarizes the results of the analysis of the pathological course of the *P. gingivalis* challenge in control and immunized animals.

TABLE 3

Pathological course of *P. gingivalis* infection.

| Group | % abdominal lesion | % death |
|---|---|---|
| A | 50% | 50% |
| B | 0 | 0 |
| C | 13% | 13% |
| D | 0 | 0 |
| E | 0 | 0 |
| F | 0 | 0 |
| G | 0 | 0 |

Specific immunoglobulin G (IgG) to *P. gingivalis* whole cells is quantitated from both chamber fluids and sera for each group of mice. IgG specific for *P. gingivalis* whole cells is assayed by a modification of an enzyme-linked immunosorbent assay (ELISA) described by Ebersole et al. (1989) *J. Dent. Res.* 68:286, abstract 837. The results are read with a $V_{max}$ kinetic photometer (Molecular Devices Corp., Menlo Park, Calif.) at 450 nm. An aliquot of serum from each group of mice (inoculated with different strains of *P. gingivalis*) is pooled and used as a positive standard and run on each plate.

Further protection experiments are performed to test the following peptides: RGP Catalytic domain Peptide B, QLPFIFDVACVNGDFLFSMPCFAEALMRAQ, SEQ ID NO:11, MAP form; Scrambled catalytic domain, in both MAP and acid forms, DQANFLQCVGSLMCRLDFFFEAVMPIFPAA, SEQ ID NO:13; N-terminal sequence of catalytic subunit of HMW RGP, Peptide A, MAP form, YTPVEEKQNGRMIVIAKKY, MAP form, SEQ ID NO:10; Adhesin domain peptide (Peptide D) from adhesin/hemagglutinin domain of HMW RGP, in MAP and acid forms, GNHEYCVEVKYTAGVSPKVCKDVTV, SEQ ID NO:14; "Scrambled" adhesin domain peptide from HMW RGP, in MAP and acid forms, AHEKTYPVEDVNCSYVKTVCVGGKV, SEQ ID NO:15.

Peptides equivalent in amino acid sequence to portions of Arg-gingipains, including adhesin/hemagglutinin domains and/or catalytic proteins, have protective effects when used to immunize mice in the animal model described herein. "Scrambled" peptides do not confer protective immunity to subsequent challenge by live, infectious *P. gingivalis*.

Additional peptides within the scope of the present invention include RMFMNYEPGRYTPVEEKQNG (SEQ ID NO:16) which overlaps the activation site, TFAGFED-TYKRMFMNYEPGR (SEQ ID NO:17) which is located some twenty amino acids upstream of the activation site, DYTYTVYRDGTKIKEGLTATTFEEDG-VATGNMEYCVCVKYTAGVSPKVC (SEQ ID NO:18), YTYTVYRDGTKIKEGLTATTFEEDG (SEQ ID NO:19), RDGTKIKEGLTATTFEEDGVATGN (SEQ ID NO:20) and KIKEGLTATTFEEDGVATGNHEY (SEQ ID NO:21), all of which contain the FEED (SEQ ID NO:22) sequence which participates in fibronectin binding. Peptide KWDAPNGTP-NPNPNPNPNPNPGTTTLSE (SEQ ID NO:23) also can result in protective immunity after vaccination of a human or animal.

A second immunization/challenge was carried out using Balb/C mice in the subcutaneous chamber model described above. Groups of eight mice per group were immunized by injection into the implanted subcutaneous chambers as set forth in Table 4:

TABLE 4

| Group | Immunogen | Number of Mice |
|---|---|---|
| A | None | 8 |
| B | 50 kDa RGP-2 | 8 |
| E | Peptide D | 8 |
| F | "Scrambled" Peptide D | 8 |
| G | Peptide A | 8 |
| H | Peptide A | 8 |
| I | 95 kDa RGP-1 | 8 |
| J | heat-killed *P. gingivalis* A7436 whole cells | 8 |

Group A mice (negative controls) were injected with Freund's complete adjuvant only. Mice in groups E–H were each first injected with 50 µg MAP-peptide in Freund's complete adjuvant; eight boosts each contained 50 µg MAP-peptide in Freund's incomplete adjuvant. For groups E and F, boosts #3 and #6 were with free peptide. Groups B and F were treated as in the first experiment with eight boosts. Group J mice received heat-killed *P. gingivalis* A7436 cells without adjuvant ($10^8$ cells in primary injection, $10^2$ cells per boost)

Each mouse was challenged by injection of $3.9 \times 10^{10}$ *P. gingivalis* A7436 into the subcutaneous chambers on the 32nd day after primary immunization.

Table 5 presents the results for recovery of viable *P. gingivalis* cells from the subcutaneous chambers at days 1, 2, 3, 5 and 7 after challenge.

TABLE 5

Recovery of *P. gingivalis* from chambers following challenge
% of mice from which *P. gingivalis* was cultured and (CFU) Day Following Challenge

| Group | 1 | 2 | 3 | 5 | 7 |
|---|---|---|---|---|---|
| A | 100% $(2.1 \times 10^{12})$ | 100% $(1.6 \times 10^{12})$ | 88% $(1.1 \times 10^{12})$ | 88% $(6 \times 10^{12})$ | 88% $(2.6 \times 10^{12})$ |
| B | 88% $(1.0 \times 10^{12})$ | 75% $(2.1 \times 10^{10})$ | 63% $(2.8 \times 10^{10})$ | 75% $(2 \times 10^{10})$ | 75% $(2 \times 10^{10})$ |
| C | 75% $(1.6 \times 10^{12})$ | 50% $(1.2 \times 10^{10})$ | 50% $(6 \times 10^9)$ | 50% $(1.2 \times 0\ 10^9)$ | 50% $(1.6 \times 10^8)$ |
| D | 75% $(2.1 \times 10^{10})$ | 75% (NF*) | 75% (NF) | 75% (NF) | 75% (NF) |
| E | 75% $(2.4 \times 10^{10})$ | 63% $(1 \times 10^{10})$ | 63% $(4.5 \times 10^8)$ | 63% $(2 \times 10^8)$ | 63% (NF) |
| F | 63% (NF) | 63% (NF) | 50% (NF) | 50% (NF) | 50% (NF) |
| G | 75% $(6 \times 10^{11})$ | 63% $(1.5 \times 10^{10})$ | 63% $(8 \times 10^9)$ | 63% $(5 \times 10^8)$ | 63% $(5 \times 10^8)$ |
| H | 75% $(1.4 \times 10^{10})$ | 75% (NF) | 75% (NF) | 50% (NF) | 63% (NF) |
| I | 88% $(6 \times 10^{12})$ | 63% (NF) | 38% (NF) | 38% (NF) | 38% (NF) |
| J | 100% $(1.4 \times 10^{12})$ | 88% $(1.7 \times 10^{12})$ | 100% (NF) | 88% (NF) | 88% (NF) |

Table 6 summarizes the observations for pathological effects at 7 days after challenge.

TABLE 6

Pathology observed following challenge with *P. gingivalis*

| Group | % Lesions | % Deaths | Cachexia |
|---|---|---|---|
| A | 38% | 38% | +++++ |
| B | 0 | 0 | + |
| C | 0 | 0 | ++ |
| D | 0 | 0 | ++++ |
| E | 0 | 13% | ++ |
| F | 25% | 0 | ++++ |
| G | 0 | 0 | + |
| H | 0 | 0 | + |
| I | 0 | 0 | − |
| J | 0 | 0 | ++ |

Cachexia scored on a scale from +++++ to −, with +++++ as severe and − as no cachexia.

In further animal experiments, seven days post primary immunization mice were boosted (10×) at 3 day intervals with RGP-1, RGP-2, or MAP-conjugated peptides (50 μg/mouse in Freund's incomplete adjuvant). Animals immunized with heat-killed *P. gingivalis* were boosted (10×) at 3 day intervals with heat-killed *P. gingivalis* corresponding to $10^2$ CFU. At 14, 21, and 28 days postimmunization, chamber fluid was removed with a hypodermic needle and syringe, and IgG specific for RGP-1, RGP-2, KGP, and whole cells quantitated by an immunosorbent assay [Ebersole et al. (1984) *J. Clin. Microbiol.* 19:639]. Mice were challenged by inoculation of $10^9$ CFU of *P. gingivalis* A7436 directly into chambers 49 days postimmunization and examined daily for size and consistency of lesions and health status. Severe cachexia was defined as ruffled hair, hunched bodies, and weight loss. Chamber fluid was removed from each implanted chamber at 1 to 7 days postchallenge for bacteriological culturing and immunological analysis. All surviving animals were sacrificed 30 days postchallenge, and sera were separated from blood obtained by cardiac puncture.

TABLE 7

Recovery of *P. gingivalis* from chamber fluid following challenge

| | | Number of mice from which *P. gingivalis* was cultured and/total number of mice sampled on the following day postinoculation[a] | | | |
|---|---|---|---|---|---|
| Group | Total Mice | 1 | 2 | 5 | 7 |
| Non-immunized | 22 | 21/22 $(1.4 \times 10^{12})^c$ | 20/22 $(1.1 \times 10^{12})$ | 20/22 $(2.4 \times 10^{12})$ | D[b] |
| Peptide A | 32 | 23/32 $(7.2 \times 10^{11})$ | 21/21 $(1.9 \times 10^{10})$ | 19/32 $(9.8 \times 10^8)$ | 19/32 $(<10^6)$ |
| Scrambled peptide | 8 | 8/8 $(6.7 \times 10^{10})$ | 8/8 $(4.8 \times 10^{10})$ | 7/8 $(2.0 \times 10^{10})$ | 7/8 $(5.6 \times 10^8)$ |
| Whole cells | 24 | 17/24 $(7.4 \times 10^{11})$ | 11/27 $(8.8 \times 10^{11})$ | 9/24 $(4.6 \times 10^8)$ | 6/24 $(<10^6)$ |
| RGP-1 | 24 | 12/24 $(2 \times 10^{12})$ | 9/24 $(8 \times 10^9)$ | 4/24 $(<10^6)$ | 3/24 $(<10^6)$ |
| RGP-2 | 22 | 15/22 $(6.1 \times 10^{11})$ | 9/22 $(1.8 \times 10^{11})$ | 7/22 $(1.2 \times 10^{10})$ | 6/22 $(<10^6)$ |

[a]Aliquots of fluid from each chamber were streaked for isolation onto anaerobic blood agar plates and cultured at 37° C. for 7 days under anerobic conditions.
[b]All animals in this group had died by day 7.
[c]Colony forming units obtained from chamber fluid.

TABLE 8

Pathological course of *P. gingivalis* infection in immunized mice

| Group | Total Mice | Lesions[a] | Deaths | Cachexia[c] |
|---|---|---|---|---|
| Non-immunized | 22 | 14/22 | 14/22 | +++++ |
| Peptide A | 32 | 1/32 | 0/32 | + |
| Scrambled peptide | 8 | 5/8 | 5/8 | ++++ |
| Whole cells | 24 | 0/24 | 0/24 | + |
| RGP-1 | 22 | 0/22 | 0/22 | ++ |
| RGP-2 | 24 | 0/24 | 0/22 | + |

[a]Number of mice with secondary lesion on the ventral abdomen/total of mice tested as detected on day 7.
[b]Number of dead mice/total number of mice tested by day 7.
[c]Cachexia scored on a scale from +++++ to −, with +++++ as severe cachexia and "−" as no cachexia.

Additional animal experiments are carried out in a mouse periodontitis model. Oral infection is with *P. gingivalis* cells in carboxymethylcellulose by gavage. Where there is infection and resulting periodontal disease, there is measurable bone loss by the end of 6 weeks, *P. gingivalis* can be cultured from infected sites, and damage within the periodontal ligament can be assessed.

TABLE 9

Enzyme linked immonosorbent assay (ELISA) analysis of chamber fluid and serum from mice immunized with gingipains Rs, peptide fragment of gingipains, and whole bacteria

| | Antibodies titer[a] against | | | | | | | |
|---|---|---|---|---|---|---|---|---|
| | RGP-1 | | RGP-2 | | KGP | | whole *P. gingivalis* | |
| Antitgen used for immunization | chamber fluid | serum | chamber fluid | serum | chamber fluid | serum | chamber fluid | serum |
| RGP-1 | 200,000 ± 28,000 | 724,000 ± 38,200 | 6,600 ± 1,440 | 55,000 ± 3,600 | 105,000 ± 13,500 | 676,000 ± 41,250 | 13,000 ± 1,100 | 282,000 ± 27,000 |
| RGP-2 | 3,600 ± 510 | 426,000 ± 32,500 | 2,800 ± 415 | 100,000 ± 15,200 | —[b] | 100,000 ± 16,000 | 400 ± 28 | 126,000 ± 20,800 |
| The N-terminal peptide of RGPs | 710 ± 52 | 100,000 ± 17,800 | 145 ± 8 | 3,600 ± 620 | — | 123,000 ± 12,100 | — | 190,000 ± 21,300 |
| Scrambled N-terminal peptide | n.r.[c] | 120,000 ± 19,400 | n.r. | 8,700 ± 722 | n.r. | 93,000 ± 10,000 | n.r. | 195,000 ± 20,300 |
| Adhesive domain peptide | 210 ± 21 | 120,000 ± 21,000 | n.r. | 7,600 ± 690 | 290 ± 17 | 83,000 ± 8,200 | 50 ± 4 | 100,000 ± 18,000 |
| Scrambled adhesive domain peptide | n.r. | 145,000 ± 23,600 | n.r. | 4,100 ± 650 | n.r. | 109,000 ± 10,500 | n.r. | 155,000 ± 20,300 |
| Heat killed *P. gingivolis* | 22,000 ± 2,500 | 331,000 ± 29,400 | 760 ± 48 | 49,000 ± 7,800 | 20,000 ± 2,600 | 234,000 ± 24,000 | 12,000 ± 980 | 178,000 ± 21,000 |

Microplates were coated with purified gingipains (1 µg/ml) or whole *P. gingivalis* cells (13), non-specific binding sites blocked with bovine serum albumin, then incubated with serial dilutions of chamber fluid or serum. Quantity of antibodies bound to immobilized antigen was determined with peroxidase-labeled goat anti-mouse IgG.
[a]Expressed as a dilution factor of chamber fluid or serum at which there was 50% of maximal $O.D._{540}$ reading calculated from sigmoidal curve obtained in ELISA assay.
[b]Detectable IgG binding but too low to be quantitated
[c]No IgG binding at the lowest (5 fold) chamber fluid or serum dilution.

We claim:

1. An isolated oligopeptide of 49 or fewer amino acids, said oligopeptide comprising an amino acid sequence selected from the group consisting of amino acid sequences as given in SEQ ID NO:9, SEQ ID NO:11, SEQ ID NO:12, SEQ ID NO:14, SEQ ID NO:16, SEQ ID NO:17, SEQ ID NO:18, SEQ ID NO:19, SEQ ID NO:20, SEQ ID NO:21, and SEQ ID NO:23 wherein the isolated oligopeptide has immunogenic properties.

2. An immunogenic composition comprising at least one isolated oligopeptide of 49 or fewer amino acids, said oligopeptide comprising an amino acid sequence selected from the group consisting of amino acid sequences as given in SEQ ID NO:9, SEQ ID NO:11, SEQ ID NO:12, SEQ ID NO:14, SEQ ID NO:16, SEQ ID NO:17, SEQ ID NO:18, SEQ ID NO:19, SEQ ID NO:20, SEQ ID NO:21, SEQ ID NO:23, and SEQ ID NO:24 and an immunological adjuvant.

3. The immunogenic composition of claim 2 comprising an oligopeptide, said oligopeptide comprising an amino acid sequence as given in SEQ ID:11 and an immunological adjuvant.

4. A method for protecting an animal from *Porphyromonas gingivalis* infection, said method comprising the step of administering the immunogenic composition of claim 2.

5. A method for protecting an animal, including a human, from gingivitis or periodontal disease, said method comprising the step of administering to said animal or human the immunogenic composition of claim 2.

6. The method of claim 5 wherein said immunogenic composition comprises an oligopeptide, which oligopeptide comprises an amino acid sequence as given in SEQ ID NO:11.

7. The method of claim 5 wherein said immunogenic composition is administered via a route selected from the group consisting of subcutaneous injection, intraperitoneal administration, oral administration, and administration to a mucosal surface of the animal or human for which protection is sought.

* * * * *

UNITED STATES PATENT AND TRADEMARK OFFICE
CERTIFICATE OF CORRECTION

PATENT NO. : 6,129,917
DATED : October 10, 2000
INVENTOR(S) : Potempa et al.

It is certified that error appears in the above-identified patent and that said Letters Patent is hereby corrected as shown below:

<u>Title page,</u>
Item [56], References Cited, U.S. PATENT DOCUMENTS,
Between "4,816,567 3/1989 Cabilly et al." and "5,462,734 10/1995 Letchworth, III et al." insert -- 5,447,914 9/1995 Travis et al. --;
Between "5,571,531 11/1996 McDermott et al." and "5,824,791 10/1998 Progulske-Fox et al." insert -- 5,707,620 1/1998 Travis et al. --;
OTHER PUBLICATIONS,
"Chen et al." citation, after "Inf. & Imm" insert -- . --;
"Agawa" citation, delete "Agawa" and insert therefor -- Ogawa --;
"Potempa, J. et al." citation entitled "The Multiple Forms of Trypsin-like Activity Present in Various Strains of *Porphyromonas gingivalis* are due to the Presence of Either Arg-Gingipain or Lys-Ginigpain", delete "Lys-Ginigpain" and insert therefor -- Lys-Gingipain --;
"Marsh et al.," citation, delete "*gingivalie*" and insert therefor -- *gingivalis* --.
"Ono et al.," citation, delete "(187)" and insert therefor -- (1987) --;
"Pavloff et al.," citation, delete "Characteriation" and insert therefor -- Characterization --;
"Roberts et al.," citation, delete "Purfification" and insert therefor -- Purification --;
"Sorsa et al.," citation, delete "Purfication" and insert therefor -- Purification --;
"Suido et al.," citation, delete "N-CBz-glycyl-glycy-l-arginyl" and insert therefor -- N-CBz-glycyl-glycyl-arginyl --;

UNITED STATES PATENT AND TRADEMARK OFFICE
CERTIFICATE OF CORRECTION

PATENT NO.     : 6,129,917
DATED          : October 10, 2000
INVENTOR(S)    : Potempa et al.

It is certified that error appears in the above-identified patent and that said Letters Patent is hereby corrected as shown below:

Column 16,
Line 65, delete "1980" and insert therefor -- (1980) --;

Column 27,
Line 6, after "per boost)" insert --- . --.

Signed and Sealed this

Tenth Day of June, 2003

JAMES E. ROGAN
*Director of the United States Patent and Trademark Office*